US008298565B2

(12) United States Patent
Taylor et al.

(10) Patent No.: US 8,298,565 B2
(45) Date of Patent: Oct. 30, 2012

(54) POLYMER COATINGS CONTAINING DRUG POWDER OF CONTROLLED MORPHOLOGY

(75) Inventors: Doug Taylor, Franklinton, NC (US); Jim McClain, Raleigh, NC (US); Clint Smoke, Raleigh, NC (US); Mike Cole, Raleigh, NC (US); James DeYoung, Dallas, TX (US)

(73) Assignee: Micell Technologies, Inc., Durham, NC (US)

( * ) Notice: Subject to any disclaimer, the term of this patent is extended or adjusted under 35 U.S.C. 154(b) by 918 days.

(21) Appl. No.: 11/995,687

(22) PCT Filed: Jul. 14, 2006

(86) PCT No.: PCT/US2006/027321
§ 371 (c)(1),
(2), (4) Date: Jun. 16, 2008

(87) PCT Pub. No.: WO2007/011707
PCT Pub. Date: Jan. 25, 2007

(65) Prior Publication Data
US 2009/0123515 A1    May 14, 2009

Related U.S. Application Data

(60) Provisional application No. 60/699,650, filed on Jul. 15, 2005, provisional application No. 60/752,338, filed on Dec. 20, 2005, provisional application No. 60/771,066, filed on Feb. 7, 2006, provisional application No. 60/771,725, filed on Feb. 8, 2006, provisional application No. 60/745,733, filed on Apr. 26, 2006, provisional application No. 60/745,731, filed on Apr. 26, 2006.

(51) Int. Cl.
*A61F 2/00* (2006.01)
*A61K 31/436* (2006.01)
*B05D 7/02* (2006.01)

(52) U.S. Cl. .................. 424/423; 427/2.31; 514/291

(58) Field of Classification Search .................. None
See application file for complete search history.

(56) References Cited

U.S. PATENT DOCUMENTS

| | | |
|---|---|---|
| 3,087,660 A | 4/1963 | Endicott |
| 3,087,860 A | 4/1963 | Endicott |
| 3,929,992 A | 12/1975 | Sehgal et al. |
| 4,326,532 A | 4/1982 | Hammar |
| 4,733,665 A | 3/1988 | Palmaz |
| 5,158,986 A | 10/1992 | Cha et al. |
| 5,243,023 A | 9/1993 | Dezern |
| 5,340,614 A | 8/1994 | Perman et al. |
| 5,342,621 A | 8/1994 | Eury |
| 5,356,433 A | 10/1994 | Rowland et al. |
| 5,470,603 A | 11/1995 | Staniforth et al. |
| 5,569,463 A | 10/1996 | Helmus et al. |
| 5,811,032 A | 9/1998 | Kawai et al. |
| 5,824,049 A | 10/1998 | Ragheb et al. |
| 5,837,313 A | 11/1998 | Ding et al. |
| 5,873,904 A | 2/1999 | Ragheb et al. |
| 5,948,020 A | 9/1999 | Yoon et al. |
| 5,957,975 A | 9/1999 | Lafont et al. |
| 6,143,037 A | 11/2000 | Goldsten et al. |
| 6,153,252 A | 11/2000 | Hossainy et al. |
| 6,190,699 B1 | 2/2001 | Luzzi et al. |
| 6,273,913 B1 | 8/2001 | Wright et al. |
| 6,319,541 B1 | 11/2001 | Pletcher et al. |
| 6,364,903 B2 | 4/2002 | Tseng et al. |
| 6,368,658 B1 * | 4/2002 | Schwarz et al. .............. 427/2.15 |
| 6,372,246 B1 | 4/2002 | Wei et al. |
| 6,409,716 B1 | 6/2002 | Sahatjian et al. |
| 6,414,050 B1 | 7/2002 | Howdle et al. |
| 6,448,315 B1 | 9/2002 | Lidgren et al. |
| 6,461,644 B1 | 10/2002 | Jackson et al. |
| 6,497,729 B1 | 12/2002 | Moussy et al. |
| 6,506,213 B1 | 1/2003 | Mandel et al. |
| 6,517,860 B1 | 2/2003 | Rosser et al. |
| 6,521,258 B1 | 2/2003 | Mandel et al. |
| 6,524,698 B1 | 2/2003 | Schmoock |
| 6,627,246 B2 | 9/2003 | Mehta et al. |
| 6,649,627 B1 | 11/2003 | Cecchi et al. |
| 6,660,176 B2 | 12/2003 | Tepper et al. |
| 6,669,785 B2 | 12/2003 | DeYoung et al. |
| 6,669,980 B2 | 12/2003 | Hanson et al. |

(Continued)

FOREIGN PATENT DOCUMENTS

JP       2003533492       11/2001

(Continued)

OTHER PUBLICATIONS

Mishima et al ("Microencapsulation of Proteins by Rapid Expansion of Supercritical Solution with a Nonsolvent," AIChE Journal Apr. 2000 vol. 46, No. 4 857-865.*
Jovanovic et al ("Stabilization of Proteins in Dry Powder Formulations Using Supercritical Fluid Technology," Pharmaceutical Research, vol. 21, No. 11, Nov. 2004.*
PCT/US07/10227 Search Report mailed Aug. 8, 2008.
Latella et al., "Nanoindentation hardness. Young's modulus, and creep behavior of organic-inorganic silica-based sol-gel thin films on copper," J Mater Res 23(9): 2357-2365 (2008).
Schmidt et al., "A Comparison of the Mechanical Performance Characteristics of Seven Drug-Eluting Stent Systems," Catheterization and Cardiovascular Interventions 73:350-360 (2009).

(Continued)

*Primary Examiner* — Suzanne Ziska
(74) *Attorney, Agent, or Firm* — Wilson Sonsini Goodrich & Rosati

(57) ABSTRACT

A method for depositing a coating comprising a polymer and pharmaceutical agent on a substrate, comprising the following steps: discharging at least one pharmaceutical agent in a therapeutically desirable morphology in dry powder form through a first orifice; discharging at least one polymer in dry powder form through a second orifice; depositing the polymer and/or pharmaceutical particles onto the substrate, wherein an electrical potential is maintained between the substrate and the pharmaceutical and/or polymer particles, thereby forming the coating; and sintering the coating under conditions that do not substantially modify the morphology of the pharmaceutical agent.

18 Claims, 31 Drawing Sheets

U.S. PATENT DOCUMENTS

| | | | |
|---|---|---|---|
| 6,670,407 B2 | 12/2003 | Howdle et al. | |
| 6,706,283 B1 | 3/2004 | Appel et al. | |
| 6,710,059 B1 | 3/2004 | Labrie et al. | |
| 6,720,003 B2 | 4/2004 | Cheng et al. | |
| 6,736,996 B1 | 5/2004 | Carbonell et al. | |
| 6,749,902 B2 | 6/2004 | Yonker et al. | |
| 6,755,871 B2 | 6/2004 | Damaso et al. | |
| 6,756,084 B2 | 6/2004 | Fulton et al. | |
| 6,767,558 B2 | 7/2004 | Wang et al. | |
| 6,780,475 B2 | 8/2004 | Fulton et al. | |
| 6,837,611 B2 | 1/2005 | Kuo et al. | |
| 6,838,089 B1 | 1/2005 | Carlsson et al. | |
| 6,838,528 B2 | 1/2005 | Zhao | |
| 6,860,123 B1 | 3/2005 | Uhlin et al. | |
| 6,884,377 B1 | 4/2005 | Burnham et al. | |
| 6,884,823 B1 | 4/2005 | Plerick et al. | |
| 6,897,205 B2 | 5/2005 | Beckert et al. | |
| 6,905,555 B2 | 6/2005 | DeYoung et al. | |
| 6,939,569 B1 | 9/2005 | Green et al. | |
| 7,163,715 B1 | 1/2007 | Kramer | |
| 7,201,940 B1 | 4/2007 | Kramer | |
| 7,279,174 B2 | 10/2007 | Pacetti et al. | |
| 7,378,105 B2 | 5/2008 | Burke et al. | |
| 7,455,688 B2 | 11/2008 | Furst et al. | |
| 7,713,538 B2 | 5/2010 | Lewis et al. | |
| 2001/0049551 A1 | 12/2001 | Tseng et al. | |
| 2002/0091433 A1 | 7/2002 | Ding et al. | |
| 2002/0133072 A1 | 9/2002 | Wang et al. | |
| 2003/0031699 A1 | 2/2003 | Van Antwerp | |
| 2003/0088307 A1 | 5/2003 | Shulze et al. | |
| 2003/0125800 A1 | 7/2003 | Shulze et al. | |
| 2003/0143315 A1 | 7/2003 | Pui et al. | |
| 2003/0180376 A1 | 9/2003 | Dalal et al. | |
| 2003/0185964 A1 | 10/2003 | Weber et al. | |
| 2003/0204238 A1 | 10/2003 | Tedeschi | |
| 2003/0222017 A1* | 12/2003 | Fulton et al. | 210/634 |
| 2004/0106982 A1 | 6/2004 | Jalisi | |
| 2004/0126542 A1 | 7/2004 | Fujiwara et al. | |
| 2004/0193177 A1 | 9/2004 | Houghton et al. | |
| 2004/0193262 A1 | 9/2004 | Shadduck | |
| 2004/0236416 A1 | 11/2004 | Falotico | |
| 2005/0003074 A1 | 1/2005 | Brown et al. | |
| 2005/0004661 A1 | 1/2005 | Lewis et al. | |
| 2005/0010275 A1 | 1/2005 | Sahatjian et al. | |
| 2005/0015046 A1 | 1/2005 | Weber et al. | |
| 2005/0019747 A1 | 1/2005 | Anderson et al. | |
| 2005/0049694 A1 | 3/2005 | Neary | |
| 2005/0069630 A1 | 3/2005 | Fox et al. | |
| 2005/0079274 A1 | 4/2005 | Palasis et al. | |
| 2005/0147734 A1 | 7/2005 | Seppala et al. | |
| 2005/0175772 A1 | 8/2005 | Worsham et al. | |
| 2005/0177223 A1 | 8/2005 | Palmaz | |
| 2005/0191491 A1 | 9/2005 | Wang et al. | |
| 2005/0196424 A1 | 9/2005 | Chappa | |
| 2005/0216075 A1 | 9/2005 | Wang et al. | |
| 2005/0238829 A1 | 10/2005 | Motherwell et al. | |
| 2005/0288481 A1 | 12/2005 | Desnoyer et al. | |
| 2006/0020325 A1 | 1/2006 | Burgermeister et al. | |
| 2006/0094744 A1 | 5/2006 | Maryanoff et al. | |
| 2006/0121089 A1 | 6/2006 | Michal et al. | |
| 2006/0134211 A1 | 6/2006 | Lien et al. | |
| 2006/0136041 A1 | 6/2006 | Schmid et al. | |
| 2006/0188547 A1 | 8/2006 | Bezwada | |
| 2006/0193886 A1 | 8/2006 | Owens et al. | |
| 2006/0193890 A1 | 8/2006 | Owens et al. | |
| 2006/0198868 A1 | 9/2006 | DeWitt et al. | |
| 2006/0222756 A1 | 10/2006 | Davila et al. | |
| 2006/0276877 A1 | 12/2006 | Owens et al. | |
| 2007/0009564 A1 | 1/2007 | McClain et al. | |
| 2007/0059350 A1 | 3/2007 | Kennedy et al. | |
| 2007/0123977 A1 | 5/2007 | Cottone et al. | |
| 2007/0196423 A1 | 8/2007 | Ruane et al. | |
| 2007/0203569 A1 | 8/2007 | Burgermeister et al. | |
| 2007/0259017 A1 | 11/2007 | Francis | |
| 2008/0075753 A1 | 3/2008 | Chappa | |
| 2008/0095919 A1 | 4/2008 | McClain et al. | |
| 2008/0118543 A1 | 5/2008 | Pacetti et al. | |
| 2008/0206304 A1 | 8/2008 | Lindquist et al. | |
| 2008/0213464 A1 | 9/2008 | O'Connor | |
| 2008/0255510 A1 | 10/2008 | Wang | |
| 2008/0292776 A1 | 11/2008 | Dias et al. | |
| 2008/0300669 A1 | 12/2008 | Hossainy | |
| 2009/0062909 A1 | 3/2009 | Taylor et al. | |
| 2009/0105809 A1 | 4/2009 | Lee et al. | |
| 2009/0186069 A1 | 7/2009 | DeYoung et al. | |
| 2009/0292351 A1 | 11/2009 | McClain et al. | |

FOREIGN PATENT DOCUMENTS

| | | |
|---|---|---|
| JP | 2003-533493 | 11/2003 |
| JP | 2004-173770 | 6/2004 |
| JP | 2004-529674 | 9/2004 |
| WO | WO-2005-042623 A1 | 5/2005 |
| WO | WO-2005-117942 A2 | 12/2005 |
| WO | WO-2006-083796 A2 | 8/2006 |
| WO | WO-2006-099276 A2 | 9/2006 |
| WO | WO-2007-011707 A2 | 1/2007 |
| WO | WO-2007-011707 A3 | 1/2007 |
| WO | WO-2007-011708 A2 | 1/2007 |
| WO | WO-2007-011708 A3 | 1/2007 |
| WO | WO-2007-127363 A2 | 1/2007 |
| WO | WO-2008-046641 | 4/2008 |
| WO | WO-2008-046642 | 4/2008 |
| WO | WO 2008/086369 | 7/2008 |
| WO | WO-2008-131131 A1 | 10/2008 |
| WO | WO 2010/009335 | 1/2010 |
| WO | WO-2010-111196 A2 | 9/2010 |
| WO | WO-2010-111196 A3 | 9/2010 |
| WO | WO-2010-111232 A3 | 9/2010 |
| WO | WO-2010-111232 A9 | 9/2010 |
| WO | WO-2010-111238 A2 | 9/2010 |
| WO | WO-2010-111238 A3 | 9/2010 |
| WO | WO-2010-120552 A2 | 10/2010 |
| WO | WO-2010-120552 A3 | 10/2010 |
| WO | WO-2010-121187 A2 | 10/2010 |
| WO | WO-2010-121187 A3 | 10/2010 |
| WO | WO-2011-009096 A1 | 1/2011 |

OTHER PUBLICATIONS

Schmidt et al., "Trackability, Crossability, and Pushability of Coronary Stent Systems—An Experimental Approach," Biomed Techn 47 (2002), Erg. 1, S. 124-126.

Schmidt et al., "In vitro measurement of quality parameters of stent-catheter systems," Biomed Techn 50(S1):1505-1506 (2005).

Schmidt et al., "New aspects of in vitro testing of arterial stents based on the new European standard," EN 14299, [online] (2009), [retrieved on Mar. 10, 2001] http://www.lib0ev.de/pl/pdf/EN14299.pdf (2009).

Szabadits et al., "Flexibility and trackability of laser cut coronary stent systems," Acta of Bioengineering and Biomechanics 11(3):11-18 (2009).

PCT/US10/42355 Search Report mailed Sep. 2, 2010.

PCT/US10/28253 Search Report and Written Opinion mailed Dec. 6, 2010.

PCT/US10/28265 Search Report and Written Opinion mailed Dec. 13, 2010.

PCT/US10/28195 Search Report and Written Opinion mailed Jan. 21, 2011.

PCT/US10/31470 Search Report and Written Opinion mailed Jan. 28, 2011.

PCT/US10/29494 Search Report and Written Opinion mailed Feb. 7, 2011.

PCT/US11/22623 Search Report and Written Opinion mailed Mar. 28, 2011.

U.S. Appl. No. 12/426,198 Office Action Mailed Mar. 23, 2011.

U.S. Appl. No. 11/995,685 Office Action Mailed Aug. 20, 2010.

U.S. Appl. No. 11/995,685 Office Action Mailed Nov. 24, 2009.

U.S. Appl. No. 11/158,724 Office Action Mailed Sep. 8, 2008.

U.S. Appl. No. 11/158,724 Office Action Mailed Sep. 17, 2009.

PCT/US09/50883 Search Report dated Nov. 17, 2009.

Domingo, C. et al., "Precipitation of ultrafine organic crystals from the rapid expansion of supercritical solutions over a capillary and a frit nozzle," J. Supercritical Fluids 10:39-55 (1997).

Ong and Serruys, "Technology Insight: an overview of research in drug-eluting stents," Nat. Clin. Parct. Cardiovas. Med. 2(12):647-658 (2005).

PCT/US10/42355 Search Report and Written Opinion dated Sep. 2, 2010.
Mario, C.D. et al., "Drug-Eluting Bioabsorbable Magnesium Stent," J. Interventional Cardiology 16(6):391-395 (2004).
PCT/US09/41045 Search Report dated Aug. 11, 2009.
PCT/US07/80213 Search Report dated Apr. 16, 2008.
PCT/US08/11852 Search Report dated Dec. 19, 2008.
PCT/US08/64732 Search Report dated Sep. 4, 2008.
PCT/US08/60671 Search Report dated Sep. 5, 2008.
PCT/US08/50536 Search Report dated Jun. 2, 2008.
PCT/US07/82275 Search Report mailed Apr. 18, 2008.
PCT/US06/27321 Search Report mailed Oct. 16, 2007.
PCT/US06/27322 Search Report mailed Apr. 25, 2007.
PCT/US06/24221 Search Report mailed Jan. 29, 2007.
McAlpine, J.B. et al., "Revised NMR Assignments for Rapamycine," J. Antibiotics 44:688-690 (1991).
Schreiber, S.L. et al., "Atomic Structure of the Rapamycin Human Immunophilin FKBP-12 Complex," J. Am. Chem. Soc. 113:7433-7435 (1991).
Serruys, Patrick et al., Comparison of Coronary-Artery Bypass Surgery and Stenting for the Treatment of Multivessel Disease, N. Engl. J. Med., 2001, vol. 344, No. 15, pp. 1117-1124.
PCT/US2011/032371, International Search Report dated Jul. 7, 2011.
JP 2008-521633 Office Action dated Jan. 6, 2012.

* cited by examiner

Solution Enhanced Dispersion of Supercritical Solutions (SEDS) Process Equipment Crystalline spray-coated rapamycin

FIGURE 7

Crystalline Rapamycin Spray Apparatus

FIGURE 10

Drug-Polymer coated coronary stent (a) immediately after deposition, (b) after annealing in a dense carbon dioxide environment at 40°C

Optical Microscopy of Rapamycin/PEVA/PBMA Coated Stents (a) Powder coated before sintering (b) Powder coated after sintering

Optical Microscopy of Rapamycin/PEVA/PBMA Coated Stents (b) Powder coated after sintering Outside Surface     Inside Surface (a) Powder coated before sintering Outside Surface     Inside Surface Optical Microscopy of Rapamycin/PEVA/PBMA Coated Stents After Sintering at 100X magnification

Scanning Electron Microscope Images of Rapamycin/PEVA/PBMA Coated Stents (b) x250 magnification (d) x3000 magnification (a) x30 magnification (c) x1000 magnification Scanning Electron Microscope Images of Rapamycin/PEVA/PBMA Coated Stent (FIB Cross-sections)

(a) x7000 magnification
Four cross-sectional thicknesses measured:
(1) 10.355µM; (2) 10.412µM; (3) 10.043µM; (4) 10.157µM (b) x20000 magnification Differential Scanning Calorimetry Analysis of Rapamycin/PEVA/PBMA Coated Stents (a) Control Experiment: PEVA
(b) Control Experiment: PBMA
(c) Control Experiment Rapamycin (Rapamycin crystalline melt indicated)
(d) Coated Rapamycin, PEVA, PBMA Mixture (Rapamycin crystalline melt indicated)

FT-IR and UV-Vis Spectrum & Calibration Curves of Rapamycin and PEVA/PBMA (a) Representative Rapamycin UV-Vis Spectrum (c) Representative PEVA/PBMA FT-IR Spectrum (b) Rapamycin Calibration Curve at 277nm (d) PEVA Calibration Curve at 1050nm (e) PBMA Calibration Curve at 1285nm

Quantification of Paclitaxel After Coating on a 3mm Guidant TriStar® Stent with Paclitaxel-polymer composite (b) Paclitaxel Quantification Using UV-Vis Standard Method (a) Paclitaxel UV-Vis calibration curve Figure 2. Graphical summary of the conditions used for the sintering experiments.

Stents exhibiting mechanically sound coating after inflation

POLYMER COATINGS CONTAINING DRUG POWDER OF CONTROLLED MORPHOLOGY

CROSS-REFERENCE

This application claims the benefit of U.S. Provisional Application Nos. 60/699,650 filed Jul. 15, 2005; 60/752,338 filed Dec. 20, 2005; 60/771,066 filed Feb. 7, 2006; 60/771,725 filed Feb. 8, 2006; 60/745,731 filed Apr. 26, 2006; and 60/745,733 filed Apr. 26, 2006 which are incorporated herein by reference in its entirety.

BACKGROUND OF THE INVENTION

The present invention relates to methods for depositing a coating comprising a polymer and a pharmaceutical or biological agent in powder form onto a substrate.

It is often beneficial to provide coatings onto substrates, such that the surfaces of such substrates have desired properties or effects.

For example, it is useful to coat biomedical implants to provide for the localized delivery of pharmaceutical or biological agents to target specific locations within the body, for therapeutic or prophylactic benefit. One area of particular interest is drug eluting stents (DES) that has recently been reviewed by Ong and Serruys in Nat. Clin. Pract. Cardiovasc. Med., (December 2005), Vol 2, No 12, 647. Typically such pharmaceutical or biological agents are co-deposited with a polymer. Such localized delivery of these agents avoids the problems of systemic administration, which may be accompanied by unwanted effects on other parts of the body, or because administration to the afflicted body part requires a high concentration of pharmaceutical or biological agent that may not be achievable by systemic administration. The coating may provide for controlled release, including long-term or sustained release, of a pharmaceutical or biological agent. Additionally, biomedical implants may be coated with materials to provide beneficial surface properties, such as enhanced biocompatibility or lubriciousness.

Conventionally, coatings have been applied by processes such as dipping, spraying, vapor deposition, plasma polymerization, and electro-deposition. Although these processes have been used to produce satisfactory coatings, there are drawbacks associated therewith. For example it is often difficult to achieve coatings of uniform thicknesses and prevent the occurrence of defects (e.g. bare spots). Also, in many processes, multiple coating steps are frequently necessary, usually requiring drying between or after the coating steps.

Another disadvantage of most conventional methods is that many pharmaceutical or biological agents, once deposited onto a substrate, suffer from poor bioavailability, reduced shelf life, low in vivo stability or uncontrollable elution rates, often attributable to poor control of the morphology and/or secondary structure of the agent. Pharmaceutical agents present significant morphology control challenges using existing spray coating techniques, which conventionally involve a solution containing the pharmaceutical agents being spayed onto a substrate. As the solvent evaporates the agents are typically left in an amorphous state. Lack of or low degree of crystallinity of the spray coated agent can lead to decreased shelf life and too rapid drug elution. Biological agents typically rely, at least in part, on their secondary, tertiary and/or quaternary structures for their activity. While the use of conventional solvent-based spray coating techniques may successfully result in the deposition of a biological agent upon a substrate, it will often result in the loss of at least some of the secondary, tertiary and/or quaternary structure of the agent and therefore a corresponding loss in activity. For example, many proteins lose activity when formulated in carrier matrices as a result of the processing methods.

Conventional solvent-based spray coating processes are also hampered by inefficiencies related to collection of the coating constituents onto the substrate and the consistency of the final coating. As the size of the substrate decreases, and as the mechanical complexity increases, it grows increasingly difficult to uniformly coat all surfaces of a substrate.

What is needed is a cost-effective method for depositing inert polymers and pharmaceutical or biological agents onto a substrate, where the collection process is efficient, the coating produced is conformal, substantially defect-free and uniform, the composition of the coating can be regulated and the morphology and/or secondary structure of the pharmaceutical or biological agents can be controlled. The method would thus permit structural and morphological preservation of the agents deposited during the coating process.

SUMMARY OF THE INVENTION

In one aspect, the invention provides a coated coronary stent, comprising: a stent framework; and a rapamycin-polymer coating wherein at least part of rapamycin is in crystalline form.

In another aspect, the invention provides a coated coronary stent, comprising: a stent framework; and a macrolide immunosuppressive (limus) drug-polymer coating wherein at least part of the drug is in crystalline form. In one embodiment, the macrolide immunosuppressive drug comprises one or more of rapamycin, 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E, 4'S)-40-O-(4',5'-Dihydroxypent-2'-en-1'-yl)-rapamycin 40-O-(2-Hydroxy)ethoxycar-bonylmethyl-rapamycin, 40-O-(3-Hydroxy)propyl-rapamycin, 40-O-(6-Hydroxy)hexyl-rapamycin, 40-O-[2-(2-Hydroxy)ethoxy]ethyl-rapamycin, 40-O-[(3S)-2,2-Dimethyldioxolan-3-yl]methyl-rapamycin, 40-O-[(2S)-2,3-Dihydroxyprop-1-yl]-rapamycin, 40-O-(2-Acetoxy)ethyl-rapamycin, 40-O-(2-Nicotinoyloxy)ethyl-rapamycin, 40-O- [2-(N-Morpholino)acetoxy]ethyl-rapamycin, 40-O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 40-O-(2-Aminoethyl)-rapamycin, 40-O-(2-Acetaminoethyl)-rapamycin 40-O-(2-Nicotinamidoethyl)-rapamycin, 40-O-(2-(N-Methyl-imidazo-2'-ylcarbethoxamido)ethyl)-rapamycin, 40-O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), and 42-[3-hydroxy-2-(hydroxymethyl)-2-methylpropanoate]rapamycin (temsirolimus).

In yet another aspect, the invention provides a method for coating a substrate, said coating comprising
  at least one polymer; and
  at least one pharmaceutical agent in a therapeutically desirable morphology and/or at least one active biological agent;
    said method comprising the following steps:
    discharging the at least one pharmaceutical agent and/or at least one active biological agent in dry powder form through a first orifice;
    discharging the at least one polymer in dry powder form through a second orifice;

depositing the polymer and pharmaceutical agent and/or active biological agent particles onto said substrate, wherein an electrical potential is maintained between the substrate and the polymer and pharmaceutical agent and, or active biological agent particles, thereby forming said coating; and sintering said coating under conditions that do not substantially modify the morphology of said pharmaceutical agent and/or the activity of said biological agent.

In a further aspect, the invention a method for coating a substrate, said coating comprising at least one polymer; and at least one pharmaceutical agent in a therapeutically desirable morphology and/or at least one active biological agent;

said method comprising the following steps:

discharging the at least one pharmaceutical agent and/or at least one active biological agent in dry powder form through a first orifice;

forming a supercritical or near supercritical fluid solution comprising at least one supercritical fluid solvent and at least one polymer and discharging said supercritical or near supercritical fluid solution through a second orifice under conditions sufficient to form solid particles of the polymer;

depositing the polymer and pharmaceutical agent and/or active biological agent particles onto said substrate, wherein an electrical potential is maintained between the substrate and the polymer and pharmaceutical agent and/or active biological agent particles, thereby forming said coating; and sintering said coating under conditions that do not substantially modify the morphology of said pharmaceutical agent and/or the activity of said biological agent.

A further aspect of the invention provides a method for depositing a coating onto a substrate, said coating comprising at least one polymer; and at least one pharmaceutical agent in a therapeutically desirable morphology in dry powder form and/or at least one active biological agent;

said method comprising the following steps:

discharging the at least one pharmaceutical agent and/or at least one active biological agent through a first orifice;

forming a first stream of a polymer solution comprising at least one solvent and at least one polymer;

forming a second stream of a supercritical or near supercritical fluid comprising at least one supercritical fluid;

contacting said first and second streams, whereby said supercritical or near critical fluid acts as a diluent of said solution under conditions sufficient to form particles of said polymer;

depositing the polymer and pharmaceutical agent and/or active biological agent particles onto said substrate, wherein an electrical potential is maintained between the substrate and the polymer and pharmaceutical agent and or active biological agent particles, thereby forming said coating; and sintering said coating under conditions that do not substantially modify the morphology of said pharmaceutical agent and/or the activity of said biological agent.

Yet another aspect of the invention provides a coated implantable medical device, comprising:

a substrate; and a coating having substantially uniform thickness disposed on said substrate, wherein said coating comprises at least one polymer and at least one pharmaceutical agent in a therapeutically desirable morphology and/or at least one active biological agent comprising an active secondary, tertiary or quaternary structure.

In one embodiment, the device is selected from the group consisting of stents, joints, screws, rods, pins, plates, staples, shunts, clamps, clips, sutures, suture anchors, electrodes, catheters, leads, grafts, dressings, pacemakers, pacemaker housings, cardioverters, cardioverter housings, defibrillators, defibrillator housings, prostheses, ear drainage tubes, ophthalmic implants, orthopedic devices, vertebral disks, bone substitutes, anastomotic devices, perivascular wraps, colostomy bag attachment devices, hemostatic barriers, vascular implants, vascular supports, tissue adhesives, tissue sealants, tissue scaffolds and intraluminal devices.

A further aspect of the invention provides a method for depositing a coating comprising a polymer and pharmaceutical agent on a substrate, wherein the method comprises the following steps:

forming a first supercritical or near critical fluid mixture that includes said at least one pharmaceutical agent;

forming a second supercritical or near critical fluid mixture that includes at least one polymer;

discharging the first supercritical or near critical fluid mixture through a first orifice under conditions sufficient to form solid particles of the pharmaceutical agent;

discharging the second supercritical or near critical fluid mixture through said first orifice or through a second orifice under conditions sufficient to form solid particles of the polymer;

depositing the solid pharmaceutical particles and/or polymer particles onto said substrate, wherein an electrical potential is maintained between the substrate and the pharmaceutical and or polymer particles, thereby forming said coating; and sintering said coating under conditions that do not substantially modify the morphology of said solid pharmaceutical particles.

Another aspect provides a method for depositing a coating comprising a polymer and a pharmaceutical agent on a substrate, comprising the following steps;

forming a first stream of a polymer solution comprising a first solvent and at least one polymer;

forming a second stream of a supercritical or near critical fluid mixture, contacting said first and second streams, whereby said supercritical or near critical fluid acts as a diluent of said first solvent under conditions sufficient to form particles of the polymer;

forming a third stream of a solution comprising a second solvent and at least one pharmaceutical agent;

forming a fourth stream of a supercritical or near critical fluid mixture, contacting said third and fourth streams, whereby said supercritical or near critical fluid acts as a diluent of said second solvent under conditions sufficient to form particles of the pharmaceutical agent;

depositing the polymer and/or pharmaceutical particles onto said substrate, wherein an electrical potential is maintained between the substrate and the pharmaceutical and/or polymer particles, thereby forming said coating; and sintering said coating under conditions that do not substantially modify the morphology of said solid pharmaceutical particles.

Yet another aspect of the invention provides a method for depositing a coating comprising a polymer and a pharmaceutical agent on a substrate, wherein the substrate is pre-coated with one or more polymers, the method comprising the following steps;

forming a first stream of a solution comprising a solvent and at least one pharmaceutical agent;

forming a second stream of a supercritical or near critical fluid mixture, contacting said first and second streams, whereby said supercritical or near critical fluid acts as a diluent of said solvent under conditions sufficient to form particles of the pharmaceutical agent;

depositing the pharmaceutical particles onto said substrate, wherein an electrical potential is maintained between the substrate and the pharmaceutical particles, thereby forming said coating; and sintering said coating under conditions that do not substantially modify the morphology of said solid pharmaceutical particles.

A further aspect provides a method for depositing a coating comprising a polymer and a pharmaceutical agent on a substrate, wherein the substrate is pre-coated with one or more pharmaceutical agents, the method comprising the following steps;

forming a first stream of a solution comprising a solvent and at least one polymer;

forming a second stream of a supercritical or near critical fluid mixture, contacting said first and second streams, whereby said supercritical or near critical fluid acts as a diluent of said solvent under conditions sufficient to form particles of the polymer;

depositing the polymer particles onto said substrate, wherein an electrical potential is maintained between the substrate and the pharmaceutical particles, thereby forming said coating; and sintering said coating under conditions that do not substantially modify the morphology of said solid pharmaceutical particles.

Yet another aspect of the invention provides a method for depositing a coating comprising a polymer and pharmaceutical agent on a substrate, wherein the method comprises the following steps:

co-introducing into a coaxial cylindrical spray tube an anti-solvent fluid mixture which is a supercritical or a near-critical fluid mixture and a solution or suspension of at least one pharmaceutical agent in a vehicle which is soluble or substantially soluble in the anti-solvent fluid mixture; contacting the anti-solvent fluid with said solution or suspension of at least one pharmaceutical agent to form a combined stream containing the supercritical or a near-critical fluid mixture, the vehicle and the pharmaceutical agent;

spraying the combined stream through an orifice of said tube into a vessel, wherein said vehicle is extracted from the solution or suspension and particles of the pharmaceutical agent substantially free of the vehicle are formed prior to deposition of said pharmaceutical particles on said substrate;

depositing the pharmaceutical particles onto a substrate pre-coated with particles of at least one polymer disposed into said vessel wherein an electrical potential is maintained between the substrate and the polymer particles, thereby forming said coating; and sintering said coating under conditions that do not substantially modify the morphology of said solid pharmaceutical particles.

Still further aspect of the invention provides a method for depositing a coating comprising a polymer and pharmaceutical agent on a substrate, wherein the method comprises the following steps:

co-introducing into a coaxial cylindrical spray tube an anti-solvent fluid mixture which is a supercritical or a near-critical fluid mixture and a solution or suspension of at least one polymer in a vehicle which is soluble or substantially soluble in the anti-solvent fluid mixture; contacting the anti-solvent fluid with said solution or suspension of at least one polymer to form a combined stream containing the supercritical or a near-critical fluid mixture, the vehicle and the polymer;

spraying the combined stream through an orifice of said tube into a vessel, wherein said vehicle is extracted from the solution or suspension and particles of the polymer substantially free of the vehicle are formed prior to deposition of said polymer particles on said substrate;

depositing the polymer particles onto a substrate pre-coated with particles of at least one pharmaceutical agent disposed into said vessel wherein an electrical potential is maintained between the substrate and the polymer particles, thereby forming said coating; and sintering said coating under conditions that do not substantially modify the morphology of said solid pharmaceutical particles.

A further aspect provides a method for depositing a coating comprising a polymer and a biological agent on a substrate, comprising the following steps;

forming a first stream of a polymer solution comprising a first solvent and at least one polymer;

forming a second stream of a supercritical or near critical fluid mixture, contacting said first and second streams, whereby said supercritical or near critical fluid acts as a diluent of said first solvent under conditions sufficient to form particles of the polymer;

forming a third stream of a solution comprising a second solvent and at least one biological agent;

forming a fourth stream of a supercritical or near critical fluid mixture, contacting said third and fourth streams, whereby said supercritical or near critical fluid acts as a diluent of said second solvent under conditions sufficient to form particles of the pharmaceutical agent;

depositing the polymer and/or biological agent particles onto said substrate, wherein an electrical potential is maintained between the substrate and the biological agent and/or polymer particles, thereby forming said coating; and sintering said coating under conditions that do not substantially modify the structure of said biological agent particles.

Yet another aspect provides a method for depositing a coating comprising a polymer and a pharmaceutical agent on a substrate, comprising the following steps;

forming a first stream of a solution comprising a solvent and at least one pharmaceutical agent;

discharging said stream in a vessel containing said substrate and a supercritical or near critical fluid mixture, whereby said supercritical or near critical fluid acts as a diluent of said solvent under conditions sufficient to form particles of the pharmaceutical agent;

forming a second stream of a solution comprising a solvent and at least one polymer;

discharging said second stream in said vessel, whereby said supercritical or near critical fluid acts as a diluent of said solvent under conditions sufficient to form particles of the polymer depositing the pharmaceutical and/or polymer particles onto said substrate, wherein an electrical potential is maintained between the substrate and the pharmaceutical and/or polymer particles, thereby forming said coating; and sintering said coating under conditions that do not substantially modify the morphology of said solid pharmaceutical particles.

A further aspect provides a method for depositing a coating comprising a polymer and a pharmaceutical agent on a substrate, comprising the following steps;

providing a substrate pre-coated with at least one polymer;

forming a stream of a solution comprising a solvent and at least one pharmaceutical agent;

discharging said stream in a vessel containing said substrate and a supercritical or near critical fluid mixture, whereby said supercritical or near critical fluid acts as a diluent of said solvent under conditions sufficient to form particles of the pharmaceutical agent;

depositing the pharmaceutical particles onto said substrate, wherein an electrical potential is maintained between the substrate and the pharmaceutical particles, thereby forming said coating; and sintering said coating under conditions that do not substantially modify the morphology of said solid pharmaceutical particles.

Another aspect provides a method for depositing a coating comprising a polymer and a pharmaceutical agent on a substrate, comprising the following steps;

providing a substrate pre-coated with solid particles of at least one pharmaceutical agent;

forming a stream of a solution comprising a solvent and at least one polymer;

discharging said stream in a vessel containing said substrate and a supercritical or near critical fluid mixture, whereby said supercritical or near critical fluid acts as a diluent of said solvent under conditions sufficient to form particles of the polymer;

depositing the polymer particles onto said substrate, wherein an electrical potential is maintained between the substrate and the polymer particles, thereby forming said coating; and sintering said coating under conditions that do not substantially modify the morphology of said solid pharmaceutical particles.

Yet another aspect provides a method for depositing a coating comprising a polymer and pharmaceutical agent on a substrate, wherein the method comprises the following steps:

contacting an anti-solvent fluid mixture which is a supercritical or a near-critical fluid mixture and a solution or suspension of at least one pharmaceutical agent in a vehicle which is soluble or substantially soluble in the anti-solvent fluid mixture to form a combined stream containing the supercritical or a near-critical fluid mixture, the vehicle and the pharmaceutical agent;

spraying the combined stream into a vessel, wherein said vehicle is extracted from the solution or suspension and particles of the pharmaceutical agent substantially free of the vehicle are formed prior to deposition of said pharmaceutical particles on a substrate pre-coated with particles of at least one polymer;

depositing the pharmaceutical particles onto said substrate disposed into said vessel wherein an electrical potential is maintained between the substrate and the pharmaceutical particles, thereby forming said coating; and sintering said coating under conditions that do not substantially modify the morphology of said solid pharmaceutical particles.

A further aspect of the invention provides a method for depositing a coating comprising a polymer and pharmaceutical agent on a substrate, wherein the method comprises the following steps:

contacting an anti-solvent fluid mixture which is a supercritical or a near-critical fluid mixture and a solution or suspension of at least one pharmaceutical agent in a vehicle which is soluble or substantially soluble in the anti-solvent fluid mixture to form a combined stream containing the supercritical or a near-critical fluid mixture, the vehicle and the pharmaceutical agent:

spraying the combined stream into a vessel, wherein said vehicle is extracted from the solution or suspension and particles of the pharmaceutical agent substantially free of the vehicle are formed prior to deposition of said pharmaceutical particles on a substrate pre-coated with particles of at least one polymer; wherein said anti-solvent mixture and said solution or suspension of at least one pharmaceutical agent are supplied by first and second tubes, respectively, wherein said first and second tubes are disposed at an angle;

depositing the pharmaceutical particles onto said substrate disposed into said vessel wherein an electrical potential is maintained between the substrate and the polymer particles, thereby forming said coating; and sintering said coating under conditions that do not substantially modify the morphology of said solid pharmaceutical particles A further aspect of the invention provides a method for depositing a coating comprising a polymer and at least two pharmaceutical agents on a substrate, wherein the method comprises the following steps:

contacting an anti-solvent fluid mixture which is a supercritical or a near-critical fluid mixture, a solution or suspension of a first pharmaceutical agent in a first vehicle which is soluble or substantially soluble in the anti-solvent fluid mixture, and a solution or suspension of a second pharmaceutical agent in a second vehicle which is the same as the first vehicle or another vehicle soluble or substantially soluble in the anti-solvent fluid mixture to form a combined stream containing the supercritical or a near-critical fluid mixture, the vehicle or vehicles and the first and second pharmaceutical agents;

spraying the combined stream into a vessel, wherein said vehicle is extracted from the solution or suspension and particles of the first and second pharmaceutical agents substantially free of the vehicle or vehicles are formed prior to deposition of said pharmaceutical particles on a substrate pre-coated with particles of at least one polymer; wherein said anti-solvent mixture, said solution or suspension of said first pharmaceutical agent, and said solution or suspension of said second pharmaceutical agent are supplied by first, second and third tubes, respectively, wherein said second and third tubes are each disposed at an angle from said first tube;

depositing the pharmaceutical particles onto said substrate disposed into said vessel wherein an electrical potential is maintained between the substrate and the polymer particles, thereby forming said coating; and sintering said coating wider conditions that do not substantially modify the morphology of said solid pharmaceutical particles Yet another aspect provides a coated implantable medical device, comprising:

a substrate; and a pharmaceutical agent-polymer coating having substantially uniform thickness disposed on the substrate, wherein the coating comprises at least one pharmaceutical agent all of the pharmaceutical agent or agents in the coating are substantially uniformly dispersed within the polymer coating.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 7. Crystalline spray-coated rapamycin using a process of the present invention.

FIG. 10. Further apparatus of the invention.

DETAILED DESCRIPTION OF THE INVENTION

Figure 1:
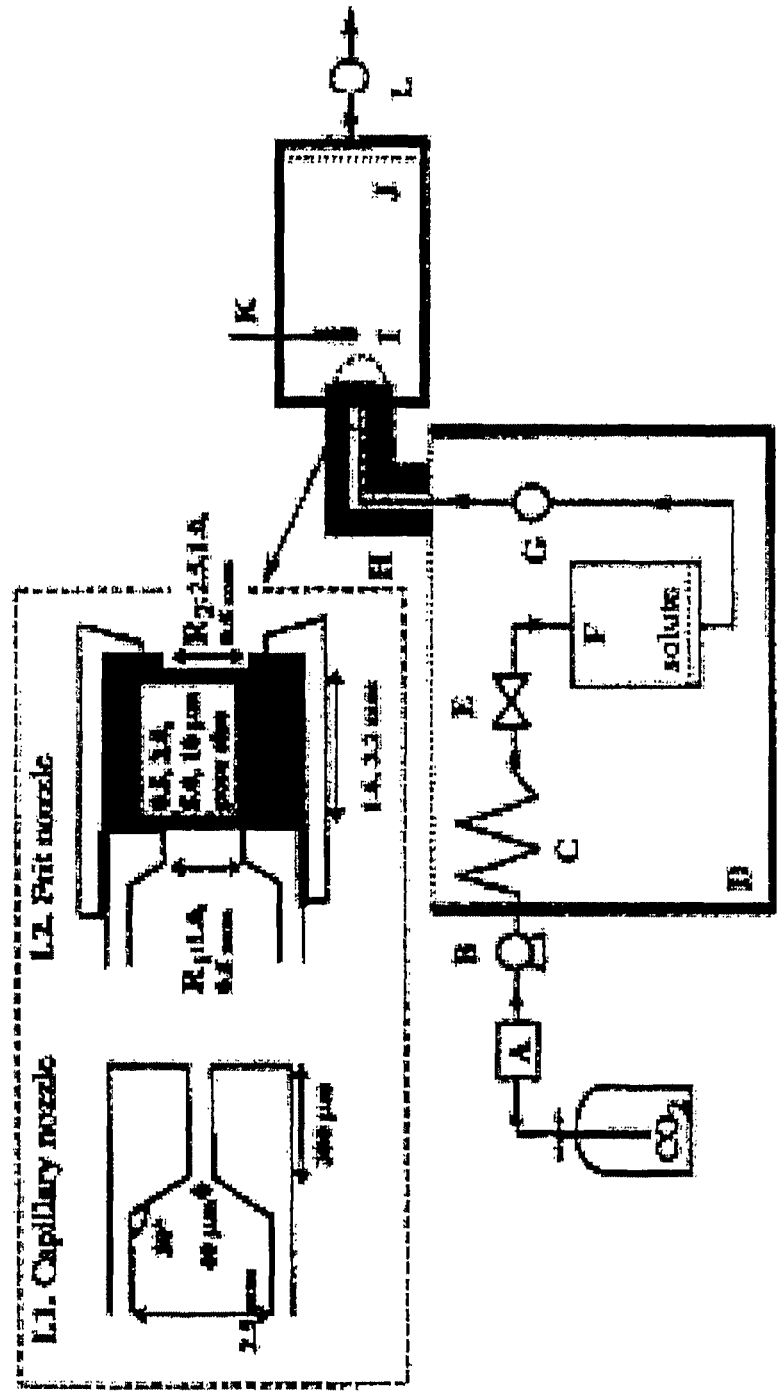
FIG. 1. Rapid Expansion of Supercritical Solutions (RESS) process equipment. See C. Domingo et al, Journal of Supercritical Fluids 10, 39-55 (1997)

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations and variations thereof.

Applicants specifically intend that all United States patent references cited herein be incorporated herein by reference in their entirety.

The present invention provides a cost-effective, efficient method for depositing a combination of an inert polymer or polymers and a pharmaceutical or biological agent or agents, onto parts or all surfaces of a substrate, to form a coating that is of a pre-determined, desired thickness, conformal, substantially defect-free, and uniform and the composition of the coating can be regulated. In particular, the present invention addresses the problem of existing coating processes, which do not allow for structural and morphological preservation of the agents deposited during the coating process.

One aspect of the invention entails the deposition of the pharmaceutical or biological agents as dry powders, using electrostatic capture to attract the powder particles to the substrate. Dry powder spraying is well known in the art, and dry powder spraying coupled with electrostatic capture has been described, for example in U.S. Pat. Nos. 5,470,603 6,319,541 or 6,372,246. The deposition of the polymer can be performed in any number of standard procedures, as the morphology of the polymer, so long as it provides coatings possessing the desired properties (e.g. thickness, conformity, defect-free, uniformity etc), is of less importance. The function of the polymer is primarily one of inert carrier matrix for the active components of the coating.

In one aspect, the coating process involves taking the substrates that have been coated with pharmaceutical or biological agents and polymers and subjecting them to a sintering process that takes place under benign conditions, which do not significantly affect the structural and morphological integrity of the pharmaceutical and biological agents. The sintering process as used in the current invention refers to the process by which parts of the matrix or the entire polymer matrix becomes continuous (e.g., formation of a continuous polymer film). As discussed below, the sintering process is controlled to produce a fully conformal continuous matrix (complete sintering) or to produce regions or domains of continuous coating while producing voids (discontinuities) in the matrix. As well, the sintering process is controlled such that some phase separation is obtained between polymer different polymers (e.g., polymers A and B) and/or to produce phase separation between discrete polymer particles. The sintering process also improves the adhesion of the polymer coating. The sintering process involves treatment of the coated substrate with a compressed gas, compressed liquid, or supercritical fluid at conditions (e.g. temperature and pressure) such that it is a poor solvent or in some instances a non-solvent for the polymers, the pharmaceutical agents and the biological agents, but induces the formation of a continuous coating of polymer. The sintering process takes place under conditions (e.g. mild temperatures), and using benign fluids (e.g. a compressed gas, or supercritical fluid, the gas or fluid may comprise carbon dioxide, isobutylene or a mixture thereof for example) which will not significantly affect the structural and morphological integrity of the pharmaceutical and/or biological agents. It is noted that while under some situations better sintering results may be obtained by using supercritical or near critical fluids, in manly embodiments according to the invention, treatment with compressed gas will provide the desired sintered polymer coating. Those of skill in the art will have no difficulty selecting a supercritical fluid, a near critical fluid or compressed gas in practicing the present invention. Sintering conditions may be adjusted such that the sintering process is not fully completed. That is, the sintering does not result in the formation of a fully continuous polymer matrix. When incomplete sintering is practiced according to the invention, some domains in the polymer matrix may be continuous, while other domains will define voids, cavities, pores, channels or interstices where the drug can be encapsulated or sequestered within the polymer matrix. Such a polymer matrix would be at a density less than the bulk density of the polymer; caused by micro or macroscopic voids in the polymer matrix. Alternatively, such a polymer matrix could retain phase separation of the polymer domains or in the case where multiple polymers are used, phase separation between the different polymer species. In most embodiments, whether the sintering process is complete or incomplete, the sintering conditions are selected to produce good adhesion of the coating to the substrate. For stents, adequate adhesion properties will generally reduce or prevent flaking or detachment of the coating from the stent during manipulation in use.

One aspect of the invention is the combination of two or more of the dry powder, RESS and SEDS spraying techniques.

Another aspect of the invention involves the dry powder spraying of a pharmaceutical agent, in a preferred particle size and morphology, into the same capture vessel as a polymer that is also dry powder sprayed, whereby the spraying of the agent and the polymer is sequential or simultaneous.

Another specific aspect of the invention involves the dry powder spraying of an active biological agent, in a preferred particle size and possessing a particular activity, into the same capture vessel as a polymer that is also dry powder sprayed, whereby the spraying of the agent and the polymer is sequential or simultaneous.

Yet another aspect of the invention involves the dry powder spraying of a pharmaceutical agent, in a preferred particle size and morphology, into the same capture vessel as a polisher that is sequentially or simultaneously sprayed by the RESS spray process.

Yet another aspect of the invention involves the dry powder spraying of an active biological agent, in a preferred particle size and possessing a particular activity, into the same capture vessel as a polymer that is sequentially or simultaneously sprayed by the RESS spray process.

Yet another aspect of the invention involves the dry powder spraying of a pharmaceutical agent, in a preferred particle size and morphology, into the same capture vessel as a polymer that is sequentially or simultaneously sprayed by the SEDS spray process.

Yet another aspect of the invention involves the dry powder spraying of an active biological agent, in a preferred particle size and possessing a particular activity, into the same capture vessel as a polymer that is sequentially or simultaneously sprayed by the SEDS spray process.

Any combination of the above six processes is contemplated by this aspect of the invention.

In further aspects of the invention the substrates that have been coated with pharmaceutical or biological agents and polymers, as described in the above embodiments are then subjected to a sintering process. The sintering process takes place under benign conditions, which do not affect the structural and morphological integrity of the pharmaceutical and biological agents, and refers to a process by which the co-deposited pharmaceutical agent or biological agent-polymer matrix, becomes continuous and adherent to the substrate. This is achieved by treating the coated substrate with a compressed gas, compressed liquid or supercritical fluid at conditions such that it is a poor solvent of the polymers, a weak solvent of the polymers or a non-solvent for the polymers, the pharmaceutical agents and the biological agents, but an agent suitable for the treatment of polymer particles to form continuous polymer coatings. The sintering process takes place under conditions (e.g. mild temperatures), and using benign fluids (e.g. supercritical carbon dioxide) which will not affect the structural and morphological integrity of the pharmaceutical and biological agents. Other sintering processes, which do not affect the structural and morphological integrity of the pharmaceutical mid biological agents may also be contemplated by the present invention.

In further aspects of the invention, it is desirable to create coatings such that release of an active substance occurs with a predetermined elution profile when placed in the desired elution media. Coating properties can be modified in a variety of different ways in order to provide desirable elution profiles.

The chemical composition of the polymers can be varied, to provide greater or lesser amounts of polymers that will allow or restrict the elution of active substance. For example, if the intended elution media contain water, a higher content of polymers that swell in water, will allow for a faster elution of active substance. Conversely, a higher content of polymers that do not swell in aqueous media will result in a slower elution rate.

The coating properties can also be controlled by alternating polymer layers. Layers of polymers of different properties are deposited on the substrate in a sequential manner. By modifying the nature of the polymer deposited in each layer (e.g., depositing layers of different polymers) the elution profile of the coating is altered. The number of layers and the sequence in their deposition provide additional avenues for the design of coatings having controlled elution profiles.

The coating properties can also be modified by control of the macro and or micro-structure of the polymer coating (diffusion pathways). This may be achieved by varying the coating process(es) or by using different sintering conditions.

The present invention provides several approaches for controlling the elution of a drug or several drugs. For example, in one embodiment, controlled elution is achieved by the segregation of different polymers (e.g. PEVA/PBMA). In another embodiment, control of elution is achieved by controlling the conditions during the sintering process such that controlled incomplete sintering of the polymer matrix is obtained, whereby the coating would retain some of the particle-like structure of the polymer particles as deposited. Incomplete sintering would provide pores/voids in the coating and allow a additional pathways for elution of the drug, including drug elution around the polymer(s) instead of or in addition to elution through the polymer(s). The size of the pores or voids obtained through incomplete sintering of the polymer matrix may be obtained through several methods. For example, the rate of depressurization of a vessel in which the sintering process is carried out provides one avenue for controlling pore size. The size of the cavities or pores in the coating can be controlled by employing a porogen as an excipient and subsequent removal of at least a portion of the porogen, for example by treatment with a solvent of the porogen. Preferably, the porogen solvent comprises a densified gas (e.g.; carbon). In some embodiments the porogen is an SOA or other such hydrophobically derivatized carbohydrate. Removal of at least a portion of the porogen is preferably carried out during the sintering process.

In some aspects of the invention, the active substance elution profile is controllable by altering the polymer particle size. The method by which the polymer particles are deposited onto the substrate is thus varied to provide the desired elution rate. For example, for polymers released simultaneously through the same nozzle, RESS release from a supercritical solution would typically result in small polymer particles; RESS-like release from a mixture in a compressed gas usually generates larger polymer particles. Using the SEDS process can result in variable polymer particle size, depending on the particular SEDS conditions employed.

In further aspects of the invention, the active substance elution profile is controllable by altering the polymer particle shape. One way to achieve variation in polymer particle shape is to alter the initial concentration of the polymers. At lower initial concentrations, polymers are deposited as small particles. At increased concentrations, larger particles are formed. At higher concentrations, the formed particles become elongated, until at high concentrations the elongated features become fiber-like and eventually become continuous fibers.

In yet other aspects of the invention, the active substance elution profile is controllable by creating discrete domains of chemically different polymers. As described above, chemically different polymers will allow or restrict the elution of active substance in different elution media. By changing the position of such polymers in discrete macroscopic domains within the coating, the elution profiles will be adjustable. For example during a process whereby two different polymers are released sequentially through the same nozzle, particles of either polymer could be deposited to position them, for example, closer to the outside, the inside or the middle of the coating on the substrate. In another embodiment, the two polymers may be released simultaneously through two different nozzles at differing and/or alternating deposition rates, resulting in a similar effect. In a further embodiment, the deposition of eluting and non-eluting polymers is alternated to result in a fluctuating type of release. In yet other embodiments, the polymers are deposited to provide for a pulsatile release of active substance. Separation of the polymer(s) providing different domains for drug diffusion is achieved, for example, by subsequent spray of the polymers through same nozzle or by using multiple nozzles. Also, as described above, controlling the elution of the active substance may be achieved by layering of different polymers across the depth of the coating. A combination of domain separation and cross-depth layering is also contemplated for the design of coatings having controlled elution properties.

The deposition of active substance during any of these processes may be constant to provide even distribution throughout the coating, or the spraying of the active substance may be varied to result in differing amounts of active substance in the differing polymeric domains within the coating.

In further aspects of the invention, the active substance elution profile is controllable by varying the coating sintering conditions. For example, incomplete sintering will create open spaces, or pores in the interstitial spaces between the polymer particles, which will enable faster eluting of active substance from the coating. Another way to utilize the sintering conditions for elution control would be to deliberately create irregular coatings by foaming during the sintering process. Rapid pressure release of a $CO_2$— or isobutylene-impregnated polymer film induces formation of foamed polymers which would create a coating with increased porosity and be very 'open' to diffusion/elution. Thus the elution profile would be controllable by manipulating the foaming conditions, which in turn controls the pore density and size.

Definitions

As used in the present specification, the following words and phrases are generally intended to halve the meanings as set forth below, except to the extent that the context in which they are used indicates otherwise.

"Substrate" as used herein, refers to any surface upon which it is desirable to deposit a coating comprising a polymer and a pharmaceutical or biological agent, wherein the coating process does not substantially modify the morphology of the pharmaceutical agent or the activity of the biological agent. Biomedical implants are of particular interest for the present invention; however the present invention is not intended to be restricted to this class of substrates. Those of skill in the art will appreciate alternate substrates that could benefit from the coating process described herein, such as pharmaceutical tablet cores, as part of an assay apparatus or as components in a diagnostic kit (e.g. a test strip).

"Biomedical implant" as used herein refers to any implant for insertion into the body of a human or animal subject, including but not limited to stents (e.g., vascular stents), electrodes, catheters, leads, implantable pacemaker, cardioverter or defibrillator housings, joints, screws, rods, ophthalmic implants, femoral pins, bone plates, grafts, anastomotic devices, perivascular wraps, sutures, staples, shunts for hydrocephalus, dialysis grafts, colostomy bag attachment devices, ear drainage tubes, leads for pace makers and implantable cardioverters and defibrillators, vertebral disks, bone pins, suture anchors, hemostatic barriers, clamps, screws, plates, clips, vascular implants, tissue adhesives and sealants, tissue scaffolds, various types of dressings (e.g., wound dressings), bone substitutes, intraluminal devices, vascular supports, etc.

The implants may be formed from any suitable material, including but not limited to organic polymers (including stable or inert polymers and biodegradable polymers), metals, inorganic materials such as silicon, and composites thereof, including layered structures with a core of one material and one or more coatings of a different material. Substrates made of a conducting material facilitate electrostatic capture. However, the invention contemplates the use of electrostatic capture in conjunction with substrate having low conductivity or which non-conductive. To enhance electrostatic capture when a non-conductive substrate is employed, the substrate is processed while maintaining a strong electrical field in the vicinity of the substrate.

Subjects into which biomedical implants of the invention may be applied or inserted include both human subjects (including male and female subjects and infant, juvenile, adolescent, adult and geriatric subjects) as well as animal subjects (including but not limited to dog, cat, horse, monkey, etc.) for veterinary purposes.

In a preferred embodiment the biomedical implant is an expandable intraluminal vascular graft or stent (e.g., comprising a wire mesh tube) that can be expanded within a blood vessel by an angioplasty balloon associated with a catheter to dilate and expand the lumen of a blood vessel, such as described in U.S. Pat. No. 4,733,665 to Palmaz Shaz.

"Pharmaceutical agent" as used herein refers to any of a variety of drugs or pharmaceutical compounds that can be used as active agents to prevent or treat a disease (meaning any treatment of a disease in a mammal, including preventing the disease, i.e. causing the clinical symptoms of the disease not to develop; inhibiting the disease, i.e. arresting the development of clinical symptoms; and/or relieving the disease, i.e. causing the regression of clinical symptoms). It is possible that the pharmaceutical agents of the invention may also comprise two or more drugs or pharmaceutical compounds. Pharmaceutical agents, include but are not limited to antirestenotic agents, antidiabetics, analgesics, antiinflammatory agents, antirheumatics, antihypotensive agents, antihypertensive agents, psychoactive drugs, tranquilizers, antiemetics, muscle relaxants, glucocorticoids, agents for treating ulcerative colitis or Crohn's disease, antiallergics, antibiotics, antiepileptics, anticoagulants, antimycotics, antitussives, arteriosclerosis remedies, diuretics, proteins, peptides, enzymes, enzyme inhibitors, gout remedies, hormones and inhibitors thereof, cardiac glycosides, immunotherapeutic agents and cytokines, laxatives, lipid-lowering agents, migraine remedies, mineral products, otologicals, anti parkinson agents, thyroid therapeutic agents, spasmolytics, platelet aggregation inhibitors, vitamins, cytostatics and metastasis inhibitors, phytopharmaceuticals, chemotherapeutic agents and amino acids. Examples of suitable active ingredients are acarbose, antigens, beta-receptor blockers, non-steroidal antiinflammatory drugs {NSAIDS}, cardiac glycosides, acetylsalicylic acid, virustatics, aclarubicin, acyclovir, cisplatin, actinomycin, alpha- and beta-sympatomimetics, (dmeprazole, allopurinol, alprostadil, prostaglandins, amantadine, ambroxol, amlodipine, methotrexate, S-aminosalicylic acid, amitriptyline, amoxicillin, anastrozole, atenolol, azathioprine, balsalazide, beclomethasone, betahistine, bezafibrate, bicalutamide, diazepam and diazepam derivatives, budesonide, bufexamac, buprenorphine methadone, calcium salts, potassium salts, magnesium salts, candesartan, carbamazepine, captopril, cefalosporins, cetirizine, chenodeoxycholic acid, ursodeoxycholic acid, theophylline and theophylline derivatives, trypsins, cimetidine, clarithromycin, clavulanic acid, clindamycin, clobutinol, clonidine, cotrimoxazole, codeine, caffeine, vitamin D and derivatives of vitamin D, colestyramine, cromoglicic acid, coumarin and coumarin derivatives, cysteine, cytarabine, cyclophosphamide, ciclosporin, cyproterone, cytabarine, dapiprazole, desogestrel, desonide, dihydralazine, diltiazem, ergot alkaloids, dimenhydrinate, dimethyl sulphoxide, dimeticone, domperidone and domperidan derivatives, dopamine, doxazosin, doxorubizin, doxylamine, dapiprazole, benzodiazepines, diclofenac, glycoside antibiotics, desipramine, econazole, ACE inhibitors, enalapril, ephedrine, epinephrine, epoetin and epoetin derivatives, morphinans, calcium antagonists, irinotecan, modafinil, orlistat, peptide antibiotics, phenyloin, riluzoles, risedronate, sildenafil, topiramate, macrolide antibiotics, oestrogen and oestrogen derivatives, progestogen and progestogen derivatives, testosterone and testosterone derivatives, androgen and androgen derivatives, ethenzamide, etofenamate, etofibrate, fenofibrate, etofylline, etoposide, famciclovir, famotidine, felodipine, fenofibrate, fentanyl, fenticonazole, gyrase inhibitors, fluconazole, fludarabine, fluarizine, fluorouracil, fluoxetine, flurbiprofen, ibuprofen, flutamide, fluvastatin, follitropin, formoterol, fosfomicin, furosemide, fusidic acid, gallopamil, ganciclovir, gemfibrozil, gentamicin, ginkgo, Saint John's wort, glibenclamide, urea derivatives as oral antidiabetics, glucagon, glucosamine and glucosamine derivatives, glutathione, glycerol and glycerol derivatives, hypothalamus hormones, goserelin, gyrase inhibitors, guanethidine, halofantrine, haloperidol, heparin and heparin derivatives, hyaluronic acid, hydralazine, hydrochlorothiazide and hydrochlorothiazide derivatives, salicylates, hydroxyzine, idarubicin, ifosfamide, imipramine, indometacin, indoramine, insulin, interferons, iodine and iodine derivatives, isoconazole, isoprenaline, glucitol and glucitol derivatives, itraconazole, ketoconazole, ketoprofen, ketotifen, lacidipine, lansoprazole, levodopa, levomnethadone, thyroid hormones, lipoic acid and lipoic acid derivatives, lisinopril, lisuride, lofepramine, lomustine, loperamide, loratadine, maprotiline, mebendazole, mebeverine, meclozine, mefenamic acid, mefloquine, meloxicam, mepindolol, meprobamate, meropenem, mesalazine, mesuximide, metamizole, metformin, methotrexate, methylphenidate, methylprednisolone, metixene, metoclopramide, metoprolol, metronidazole, mianserin, miconazole, minocycline, minoxidil, misoprostol, mitomycin, mizolastine, moexipril, morphine and morphine derivatives, evening primrose, nalbuphine, naloxone, tilidine, naproxen, narcotine, natamycin, neostigmine, nicergoline, nicethamide, nifedipine, niflumic acid, nimodipine, nimorazole, nimustine, nisoldipine, adrenaline and adrenaline derivatives, norfloxacin, novamine sulfone, noscapine, nystatin, ofloxacin, olanzapine, olsalazine, omeprazole, omoconazole, ondansetron, oxaceprol, oxacillin, oxiconazole, oxymetazoline, pantoprazole, paracetamol, paroxetine, penciclovir, oral penicillins, pentazocine, pentifylline, pentoxifylline, perphenazine, pethidine, plant extracts, phenazone, pheniramine, barbituric acid derivatives, phenylbutazone, phenytoin, pimozide, pindolol, piperazine, piracetam, pirenzepine, piribedil, piroxicam, pramipexole, pravastatin, prazosin, procaine, promazine, propiverine, propranolol, propyphenazone, prostaglandins, protionamide, proxyphylline, quetiapine, quinapril, quinaprilat, ramipril, ranitidine, reproterol, reserpine, ribavirin, rifampicin, risperidone, ritonavir, ropinirole, roxatidine, roxithromycin, ruscogenin, rutoside and rutoside derivatives, sabadilla, salbutamol, salmeterol, scopolamine, selegiline, sertaconazole, sertindole, sertralion, silicates, sildenafil, simvastatin, sitosterol, sotalol, spaglumic acid, sparfloxacin, spectinomycin, spiramycin, spirapril, spironolactone, stavudine, streptomycin, sucralfate, sufentanil, sulbactam, sulphonamides, sulfasalazine, sulpiride, sultamicillin, sultiam, sumatriptan, suxamethonium chloride, tacrine, tacrolimus, taliolol, tamoxifen, taurolidine, tazarotene, temazepam, teniposide, tenoxicam, terazosin, terbinafine, terbutaline, terfenadine, terlipressin, tertatolol, tetracyclins, teryzoline, theobromine, theophylline, butizine, thiamazole, phenothiazines, thiotepa, tiagabine, tiapride, propionic acid derivatives, ticlopidine, timolol, tinidazole, tioconazole, tioguanine, tioxolone, tiropramide, tizanidine, tolazoline, tolbutamide, tolcapone, tolnaftate, tolperisone, topotecan, torasemide, antioestrogens, tramadol, tramazoline, trandolapril, tranylcypromine, trapidil, trazodone, triamcinolone and triamcinolone derivatives, triamterene, trifluperidol, trifluridine, trimethoprim, trimipramine, tripelennamine, triprolidine, trifosfamide, tromantadine, trometamol, tropalpin, troxerutine, tulobuterol, tyramine, tyrothricin, urapidil, ursodeoxycholic acid, chenodeoxycholic acid, valaciclovir, valproic acid, vancomycin, vecuronium chloride, Viagra, venlafaxine, verapamil, vidarabine, vigabatrin, viloazine, vinblastine, vincamine, vincristine, vindesine, vinorelbine, vinpocetine, viquidil, warfarin, xantinol nicotinate, xipamide, zafirlukast, zalcitabine, zidovudine, zolmitriptan, zolpidem, zoplicone, zotipine and the like. See, e.g., U.S. Pat. No. 6,897,205; see also U.S. Pat. Nos. 6,838,528; 6,497,729.

Examples of therapeutic agents employed in conjunction with the invention include, rapamycin, 40-O-(2-Hydroxy-ethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin, 40-O-(2-Hydroxy)ethoxycarbonylm-ethyl-rapamycin, 40-O-(3-Hydroxy)propyl-rapamycin, 40-O-(6-Hydroxy)hexyl-rapamycin, 40-O-[2-(2-Hydroxy)ethoxy]ethyl-rapamycin, 40-O-[(3S)-2,2-Dimethyldioxolan-3-yl]methyl-rapamycin, 40-O-[(2S)-2,3-Dihydroxyprop-1-yl]-rapamycin, 40-O-(2-Acetoxy)ethyl-rapamycin, 40-O-(2-Nicotinoyloxy)ethyl-rapamycin, 40-O-[2-(N-Morpholino)acetoxy]ethyl-rapamycin, 4O—O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 40-O-(2-Aminoethyl)-rapamycin, 40-O-(2-Acetamidoethyl)-rapamycin, 40-O-(2-Nicotinamidoethyl)-rapamycin, 40-O-(2-(N-ethyl-imidazo-2'-ylcarbethoxamido)ethyl)-rapamycin, 40-O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), and 42-[3-hydroxy-2'-(hydroxymethyl)-2-methylpropanoate]rapamycin (temsirolimus).

The active ingredients may, if desired, also be used in the form of their pharmaceutically acceptable salts or derivatives (meaning salts which retain the biological effectiveness and properties of the compounds of this invention and which are not biologically or otherwise undesirable), and in the case of chiral active ingredients it is possible to employ both optically active isomers and racemates or mixtures of diastereoisomers.

"Stability" as used herein in refers to the stability of the drug in a polymer coating deposited on a substrate in its final product form (e.g., stability of the drug in a coated stent). The term stability will define 5% or less degradation of the drug in the final product form.

"Active biological agent" as used herein refers to a substance, originally produced by living organisms, that can be used to prevent or treat a disease (meaning any treatment of a disease in a mammal, including preventing the disease, i.e. causing the clinical symptoms of the disease not to develop; inhibiting the disease, i.e. arresting the development of clinical symptoms; and/or relieving the disease, i.e. causing the regression of clinical symptoms). It is possible that the active biological agents of the invention may also comprise two or more active biological agents or an active biological agent combined with a pharmaceutical agent, a stabilizing agent or chemical or biological entity. Although the active biological agent may have been originally produced by living organisms, those of the present invention may also have been synthetically prepared, or by methods combining biological isolation and synthetic modification. By way of a non-limiting example, a nucleic acid could be isolated form from a biological source, or prepared by traditional techniques, known to those skilled in the art of nucleic acid synthesis. Furthermore, the nucleic acid may be further modified to contain non-naturally occurring moieties. Non-limiting examples of active biological agents include peptides, proteins, enzymes, glycoproteins, nucleic acids (including deoxyribonucleotide or ribonucleotide polymers in either single or double stranded form, and unless otherwise limited, encompasses known analogues of natural nucleotides that hybridize to nucleic acids in a manner similar to naturally occurring nucleotides), antisense nucleic acids, fatty acids, antimicrobials, vitamins, hormones, steroids, lipids, polysaccharides, carbohydrates and the like. They further include, but are not limited to, antirestenotic agents, antidiabetics, analgesics, antiinflammatory agents, antirheumatics, antihypotensive agents, antihypertensive agents, psychoactive drugs, tranquilizers, antiemetics, muscle relaxants, glucocorticoids, agents for treating ulcerative colitis or Crohn's disease, antiallergics, antibiotics, antiepileptics, anticoagulants, antimycotics, antitussives, arteriosclerosis remedies, diuretics, proteins, peptides, enzymes, enzyme inhibitors, gout remedies, hormones and inhibitors thereof, cardiac glycosides, immunotherapeutic agents and cytokines, laxatives, lipid-lowering agents, migraine remedies, mineral products, otologicals, anti Parkinson agents, thyroid therapeutic agents, spasmolytics, platelet aggregation inhibitors, vitamins, cytostatics and metastasis inhibitors, phytopharmaceuticals and chemotherapeutic agents. Preferably, the active biological agent is a peptide, protein or enzyme, including derivatives and analogs of natural peptides, proteins and enzymes.

"Activity" as used herein refers to the ability of a pharmaceutical or active biological agent to prevent or treat a disease (meaning any treatment of a disease in a mammal, including preventing the disease, i.e. causing the clinical symptoms of the disease not to develop; inhibiting the disease, i.e. arresting the development of clinical symptoms; and/or relieving the disease, i.e. causing the regression of clinical symptoms). Thus the activity of a pharmaceutical or active biological agent should be of therapeutic or prophylactic value.

"Secondary, tertiary and quaternary structure" as used herein are defined as follows. The active biological agents of the present invention will typically possess some degree of secondary, tertiary and/or quaternary structure, upon which the activity of the agent depends. As an illustrative, non-limiting example, proteins possess secondary, tertiary and quaternary structure. Secondary structure refers to the spatial arrangement of amino acid residues that are near one another in the linear sequence. The α-helix and the β-strand are elements of secondary structure. Tertiary structure refers to the spatial arrangement of amino acid residues that are far apart in the linear sequence and to the pattern of disulfide bonds. Proteins containing more than one polypeptide chain exhibit an additional level of structural organization. Each polypeptide chain in such a protein is called a subunit. Quaternary structure refers to the spatial arrangement of subunits and the nature of their contacts. For example hemoglobin consists of two α and to β chains. It is well known that protein function arises from its conformation or three dimensional arrangement of atoms (a stretched out polypeptide chain is devoid of activity). Thus one aspect of the present invention is to manipulate active biological agents, while being careful to maintain their conformation, so as not to lose their therapeutic activity.

"Polymer" as used herein, refers to a series of repeating monomeric units that have been cross-linked or polymerized. Any suitable polymer can be used to carry out the present invention. It is possible that the polymers of the invention may also comprise two, three, four or more different polymers. In some embodiments, of the invention only one polymer is used. In some preferred embodiments a combination of two polymers are used. Combinations of polymers can be in varying ratios, to provide coatings with differing properties. Those of skill in the art of polymer chemistry will be familiar with the different properties of polymeric compounds. Examples of polymers that may be used in the present invention include, but are not limited to polycarboxylic acids, cellulosic polymers, proteins, polypeptides, polyvinylpyrrolidone, maleic anhydride polymers, polyamides, polyvinyl alcohols, polyethylene oxides, glycosaminoglycans, polysaccharides, polyesters, polyurethanes, polystyrenes, copolymers, silicones, polyorthoesters, polyanhydrides, copolymers of vinyl monomers, polycarbonates, polyethylenes, polypropylenes, polylactic acids, polyglycolic acids, polycaprolactones, polyhydroxybutyrate valerates, polyacrylamides, polyethers, polyurethane dispersions, polyacrylates, acrylic latex dispersions, polyacrylic acid, mixtures and copolymers thereof. The polymers of the present invention may be natural or synthetic in origin, including gelatin, chitosan, dextrin, cyclodextrin, Poly(urethanes), Poly(siloxanes) or silicones, Poly(acrylates) such as poly(methyl methacrylate), poly(butyl methacrylate), and Poly(2-hydroxy ethyl methacrylate), Poly(vinyl alcohol) Poly(olefins) such as poly(ethylene), poly(isoprene), halogenated polymers such as Poly(tetrafluoroethylene)—and derivatives and copolymers such as those commonly sold as Teflon® products, Poly(vinylidine fluoride), Poly(vinyl acetate), Poly(vinyl pyrrolidone), Poly(acrylic acid), Polyacrylamide, Poly(ethylene-co-vinyl acetate), Poly(ethylene glycol), Poly(propylene glycol), Poly(methacrylic acid); etc. Suitable polymers also include absorbable and/or resorbable polymers including the following, combinations, copolymers and derivatives of the following: Polylactides (PLA), Polyglycolides (PGA), Poly(lactide-co-glycolides) (PLGA), Polyanhydrides, Poly-orthoesters, Poly(N-(2-hydroxypropyl)methacrylamide), Poly(1-aspartamide), etc.

"Therapeutically desirable morphology" as used herein refers to the gross form and structure of the pharmaceutical agent, once deposited on the substrate, so as to provide for optimal conditions of ex vivo storage, in vivo preservation and/or in vivo release. Such optimal conditions may include, but are not limited to increased shelf life, increased in vivo stability, good biocompatibility, good bioavailability or modified release rates. Typically, for the present invention, the desired morphology of a pharmaceutical agent would be crystalline or semi-crystalline or amorphous, although this may vary widely depending on many factors including, but not limited to, the nature of the pharmaceutical agent, the disease to be treated/prevented, the intended storage conditions for the substrate prior to use or the location within the body of any biomedical implant. Preferably at least 10%, 20%, 30%, 40%, 50%, 60%, 70%, 80%, 90% or 100% of the pharmaceutical agent is in crystalline or semi-crystalline form.

"Stabilizing agent" as used herein refers to any substance that maintains or enhances the stability of the biological agent. Ideally these stabilizing agents are classified as Generally Regarded As Safe (GRAS) materials by the US Food and Drug Administration (FDA). Examples of stabilizing agents include, but are not limited to carrier proteins, such as albumin, gelatin, metals or inorganic salts. Pharmaceutically acceptable excipient that may be present can further be found in the relevant literature, for example in the Handbook of Pharmaceutical Additives: An International Guide to More Than 6000 Products by Trade Name, Chemical, Function, and Manufacturer; Michael and Irene Ash (Eds.); Gower Publishing Ltd.; Aldershot, Hampshire, England, 1995.

"Compressed fluid" as used herein refers to a fluid of appreciable density (e.g., >0.2 g/cc) that is a gas at standard temperature and pressure. "Supercritical fluid", "near-critical fluid", "near-supercritical fluid", "critical fluid", "densified fluid" or "densified gas" as used herein refers to a compressed fluid under conditions wherein the temperature is at least 80% of the critical temperature of the fluid and the pressure is at least 50% of the critical pressure of the fluid.

Examples of substances that demonstrate supercritical or near critical behavior suitable for the present invention include, but are not limited to carbon dioxide, isobutylene, ammonia, water, methanol, ethanol, ethane, propane, butane, pentane, dimethyl ether, xenon, sulfur hexafluoride, halogenated and partially halogenated materials such as chlorofluorocarbons, hydrochlorofluorocarbons, hydrofluorocarbons, perfluorocarbons (such as perfluoromethane and perfluoropropane, chloroform, trichloro-fluoromethane, dichloro-difluoromethane, dichloro-tetrafluoroethane) and mixtures thereof.

"Sintering" as used herein refers to the process by which parts of the matrix or the entire polymer matrix becomes continuous (e.g., formation of a continuous polymer film). As discussed below, the sintering process is controlled to produce a fully conformal continuous matrix (complete sintering) or to produce regions or domains of continuous coating while producing voids (discontinuities) in the matrix. As well, the sintering process is controlled such that some phase separation is obtained between polymer different polymers (e.g., polymers A and B) and/or to produce phase separation between discrete polymer particles. Through the sintering process, the adhesions properties of the coating are improved to reduce flaking of detachment of the coating from the substrate during manipulation in use. As described below, in some embodiments, the sintering process is controlled to provide incomplete sintering of the polymer matrix. In embodiments involving incomplete sintering, a polymer matrix is formed with continuous domains, and voids, gaps, cavities, pores, channels or, interstices that provide space for sequestering a therapeutic agent which is released under controlled conditions. Depending on the nature of the polymer, the size of polymer particles and/or other polymer properties, a compressed gas, a densified gas, a near critical fluid or a super-critical fluid may be employed. In one example, carbon dioxide is used to treat a substrate that has been coated with a polymer and a drug, using dry powder and RESS electrostatic coating processes. In another example, isobutylene is employed in the sintering process. In other examples a mixture of carbon dioxide and isobutylene is employed.

When an amorphous material is heated to a temperature above its glass transition temperature, or when a crystalline material is heated to a temperature above a phase transition temperature, the molecules comprising the material are more mobile, which in turn means that they are more active and thus more prone to reactions such as oxidation. However, when an amorphous material is maintained at a temperature below its glass transition temperature, its molecules are substantially immobilized and thus less prone to reactions. Likewise, when a crystalline material is maintained at a temperature below its phase transition temperature, its molecules are substantially immobilized and thus less prone to reactions. Accordingly, processing drug components at mild conditions, such as the deposition and sintering conditions described herein, minimizes cross-reactions and degradation of the drug component. One type of reaction that is minimized by the processes of the invention relates to the ability to avoid conventional solvents which in turn minimizes autoxidation of drug, whether in amorphous, semi-crystalline, or crystalline form, by reducing exposure thereof to free radicals, residual solvents and autoxidation initiators.

"Rapid Expansion of Supercritical Solutions" or "RESS" as used herein involves the dissolution of a polymer into a compressed fluid, typically a supercritical fluid, followed by rapid expansion into a chamber at lower pressure, typically near atmospheric conditions. The rapid expansion of the supercritical fluid solution through a small opening, with its accompanying decrease in density, reduces the dissolution capacity of the fluid and results in the nucleation and growth of polymer particles. The atmosphere of the chamber is maintained in an electrically neutral state by maintaining an isolating "cloud" of gas in the chamber. Carbon dioxide or other appropriate gas is employed to prevent electrical charge is transferred from the substrate to the surrounding environment.

"Bulk properties" properties of a coating including a pharmaceutical or a biological agent that can be enhanced through the methods of the invention include for example: adhesion, smoothness, conformality, thickness, and compositional mixing.

"Solution Enhanced Dispersion of Supercritical Solutions" or "SEDS" as used herein involves a spray process for the generation of polymer particles, which are formed when a compressed fluid (e.g. supercritical fluid, preferably super-critical $CO_2$) is used as a diluent to a vehicle in which a polymer dissolved, (one that can dissolve both the polymer and the compressed gas). The mixing of the compressed fluid diluent with the polymer-containing solution may be achieved by encounter of a first stream containing the polymer solution and a second stream containing the diluent compressed fluid, for example, within one co-axial spray nozzle or by the use of multiple spray nozzles or by the use of multiple fluid streams co-entering into a mixing zone. The solvent in the polymer solution may be one compound or a mixture of two or more ingredients and may be or comprise an alcohol (including diols, triols, etc.), ether, amine, ketone, carbonate, or alkanes, or hydrocarbon (aliphatic or aromatic) or may be a mixture of compounds, such as mixtures of alkanes, or mixtures of one or more alkanes in combination with additional compounds such as one or more alcohols. (e.g., from 0 or 0.1 to 5% of a $C_1$ to $C_{15}$ alcohol, including diols, triols, etc.). See for example U.S. Pat. No. 6,669,785. The solvent may optionally contain a surfactant, as also described in (for example) U.S. Pat. No. 6,669,785.

In one embodiment of the SEDS process, a first stream of fluid comprising a polymer dissolved in a common solvent is co-sprayed with a second stream of compressed fluid. Polymer particles are produced as the second stream acts as a diluent that weakens the solvent in the polymer solution of the first stream. The now combined streams of fluid, along with the polymer particles, flow into a collection vessel. In another embodiment of the SEDS process, a first stream of fluid comprising a drug dissolved in a common solvent is co-sprayed with a second stream of compressed fluid. Drug particles are produced as the second stream acts as a diluent that weakens the solvent in the drug solution of the first stream. The now combined streams of fluid, along with the drug particles, flow out into a collection vessel. Control of particle size, particle size distribution, and morphology is achieved by tailoring the following process variables: temperature, pressure, solvent composition of the first stream, flow-rate of the first stream, flow-rate of the second stream, composition of the second stream (where soluble additives may be added to the compressed gas), and conditions of the capture vessel. Typically the capture vessel contains a fluid phase that is at least five to ten times (5-10×) atmospheric pressure.

"Electrostatically charged" or "electrical potential" or "electrostatic capture" as used herein refers to the collection of the spray-produced particles upon a substrate that has a different electrostatic potential than the sprayed particles. Thus, the substrate is at an attractive electronic potential with respect to the particles exiting, which results in the capture of the particles upon the substrate. i.e. the substrate and particles are oppositely charged, and the particles transport through the fluid medium of the capture vessel onto the surface of the substrate is enhanced via electrostatic attraction. This may be achieved by charging the particles and grounding the substrate or conversely charging the substrate and grounding the particles, or by some other process, which would be easily envisaged by one of skill in the art of electrostatic capture.

"Open vessel" as used herein refers to a vessel open to the outside atmosphere, and thus at substantially the same temperature and pressure as the outside atmosphere.

"Closed vessel" as used herein refers to a vessel sealed from the outside atmosphere, and thus may be at significantly different temperatures and pressures to the outside atmosphere.

EXAMPLES

The following examples are given to enable those skilled in the art to more clearly understand and to practice the present invention. They should not be considered as limiting the scope of the invention, but merely as being illustrative and representative thereof.

Example 1

Process Equipment

Figure 2:
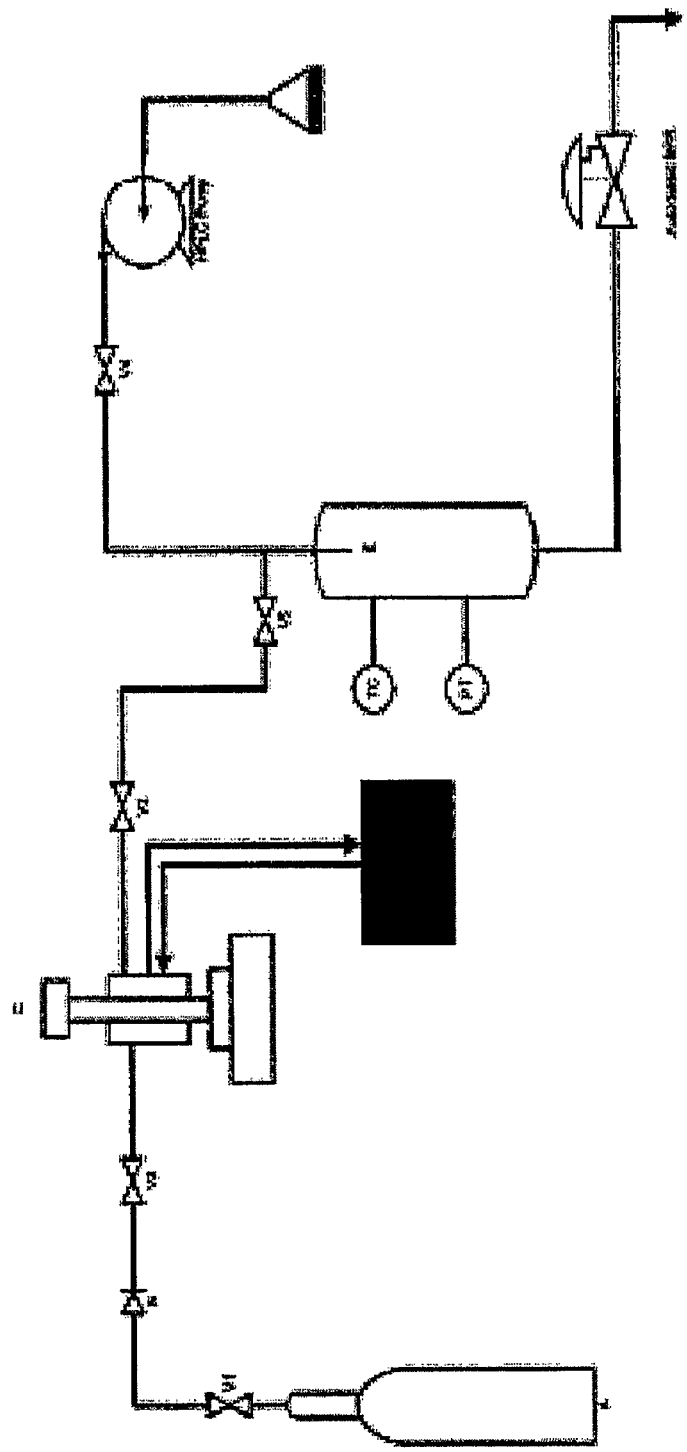
FIG. 2. Solution Enhanced Dispersion of Supercritical solutions (SEDS) process equipment.
Figure 3:
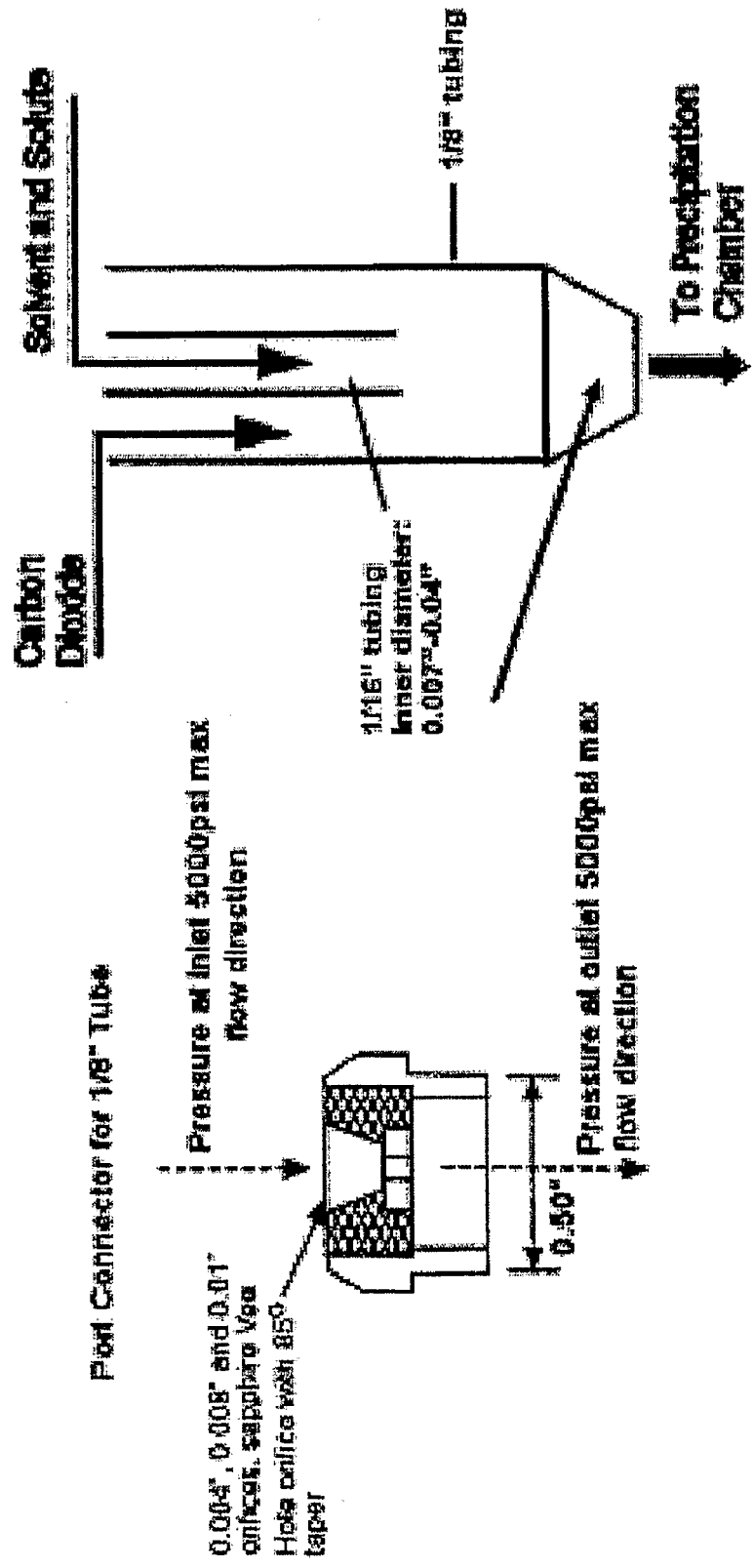
FIG. 3. SEDS nozzle design.
Figure 4:
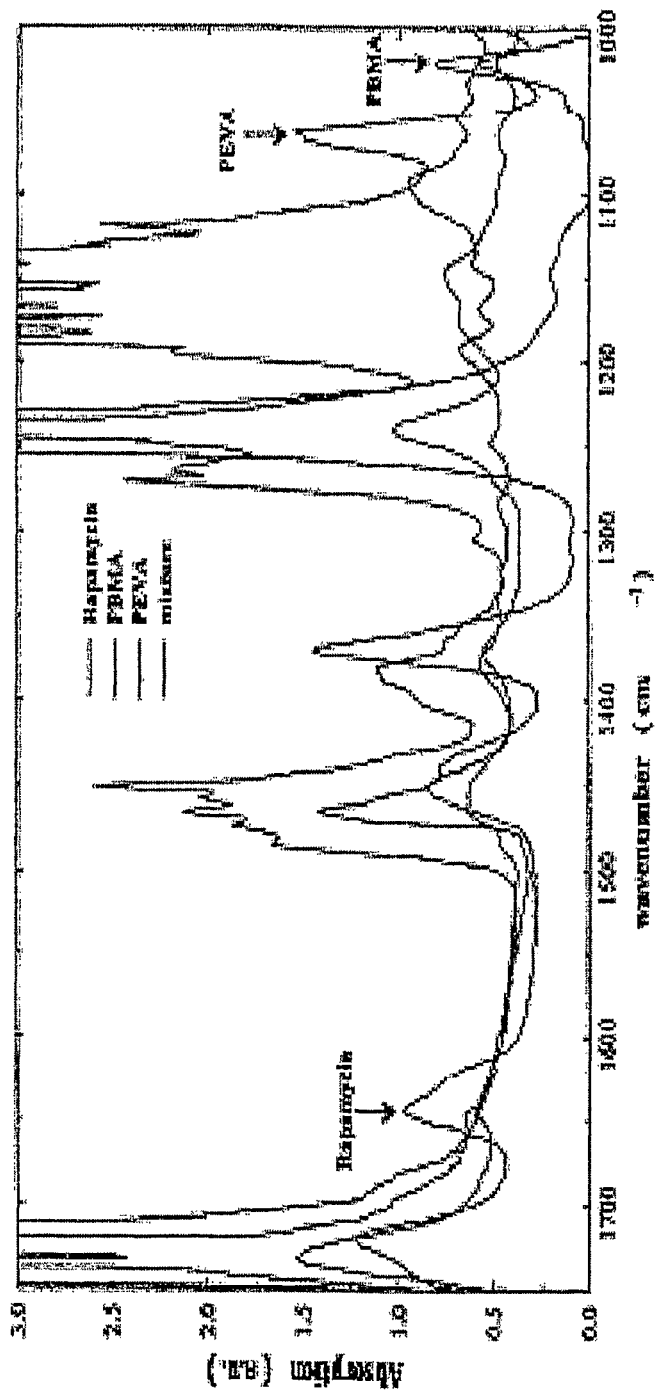
FIG. 4. FTIR spectra of each individual component and the spray coating mixture. Individual peaks for each component are labeled.
Figure 5:
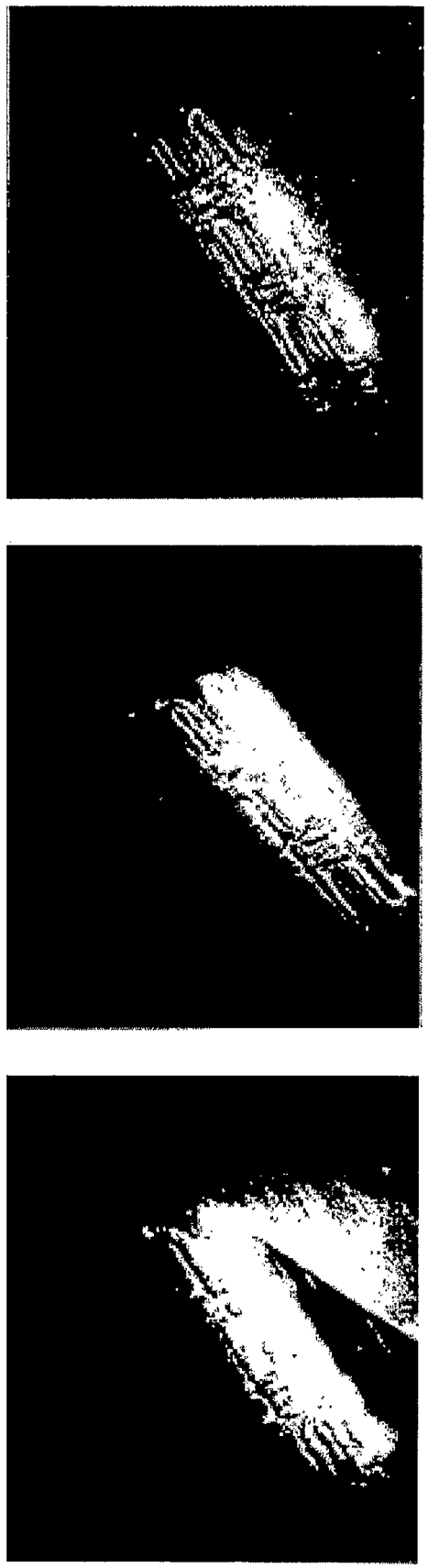
FIG. 5. Stents coated (a), (b) and sintered under different conditions (c), (d) with rapamycin, PEVA and PBMA (approximately 1:1:1). All stent surfaces are coated.
Figure 6:
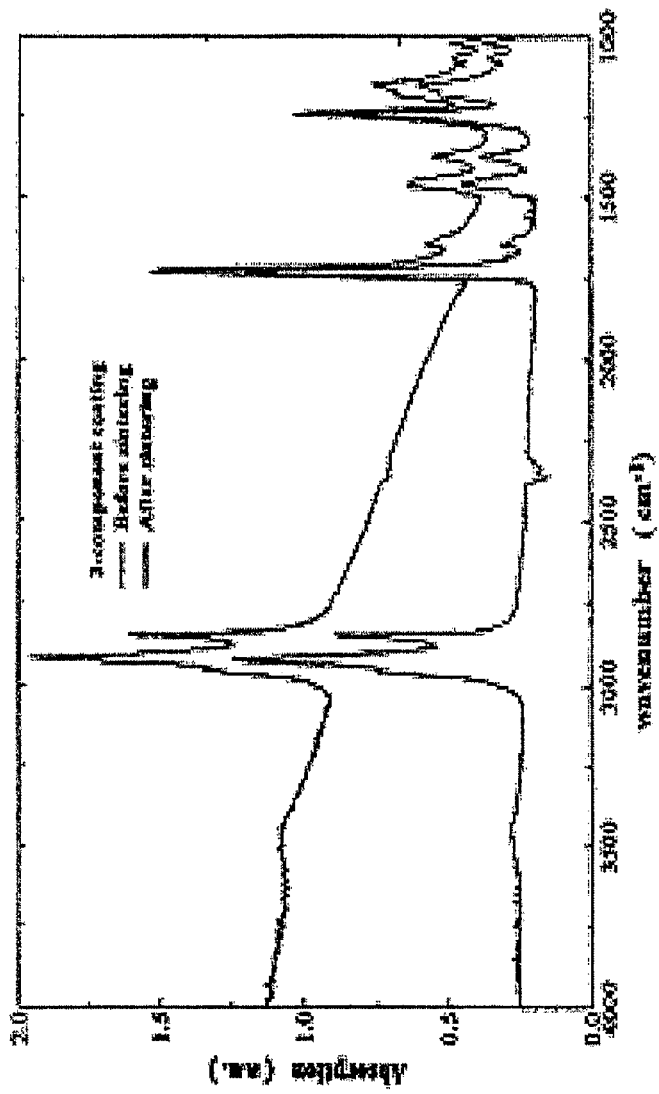
FIG. 6. IR spectra of Si wafer chips coated with Rapamycin, PEVA and PBMA before and after sintering. No differences are observable between the two spectra. The baseline shift at larger wavenumber in the as deposited spectrum is due to light scattering caused by the large particle size.
Figure 7:
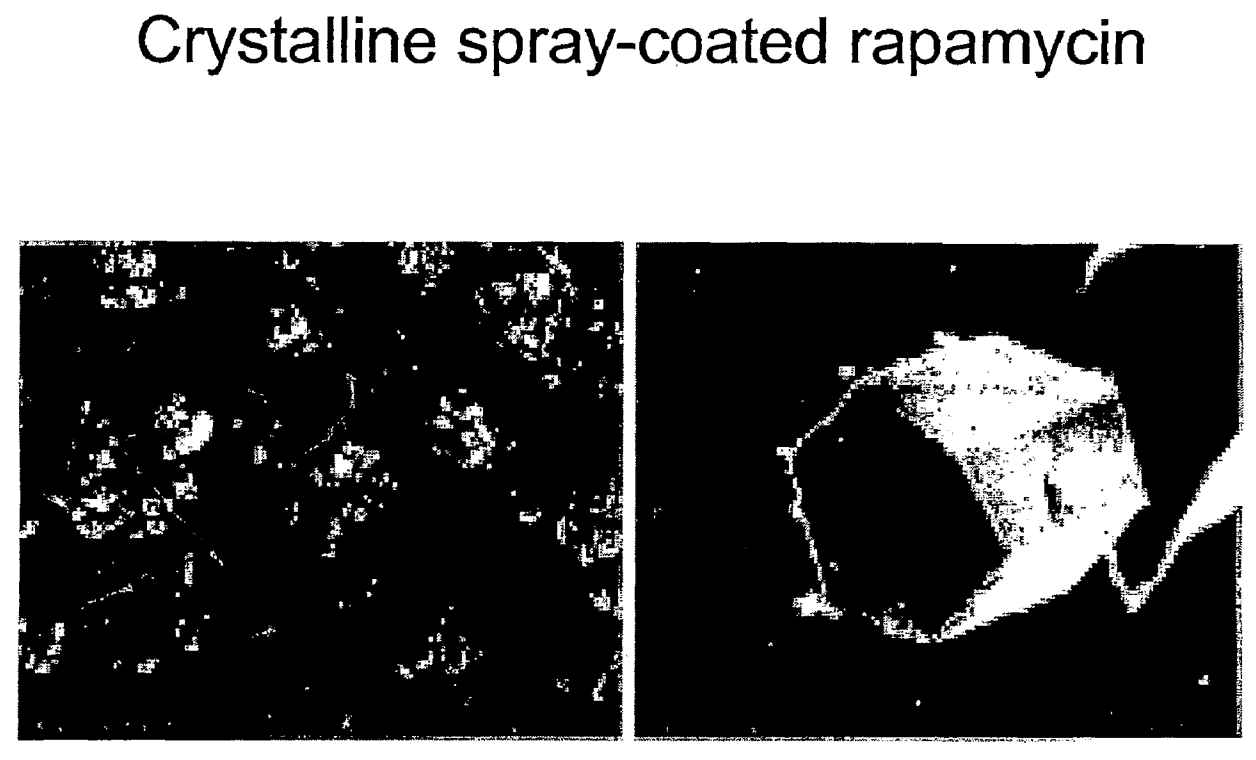
Figure 8:
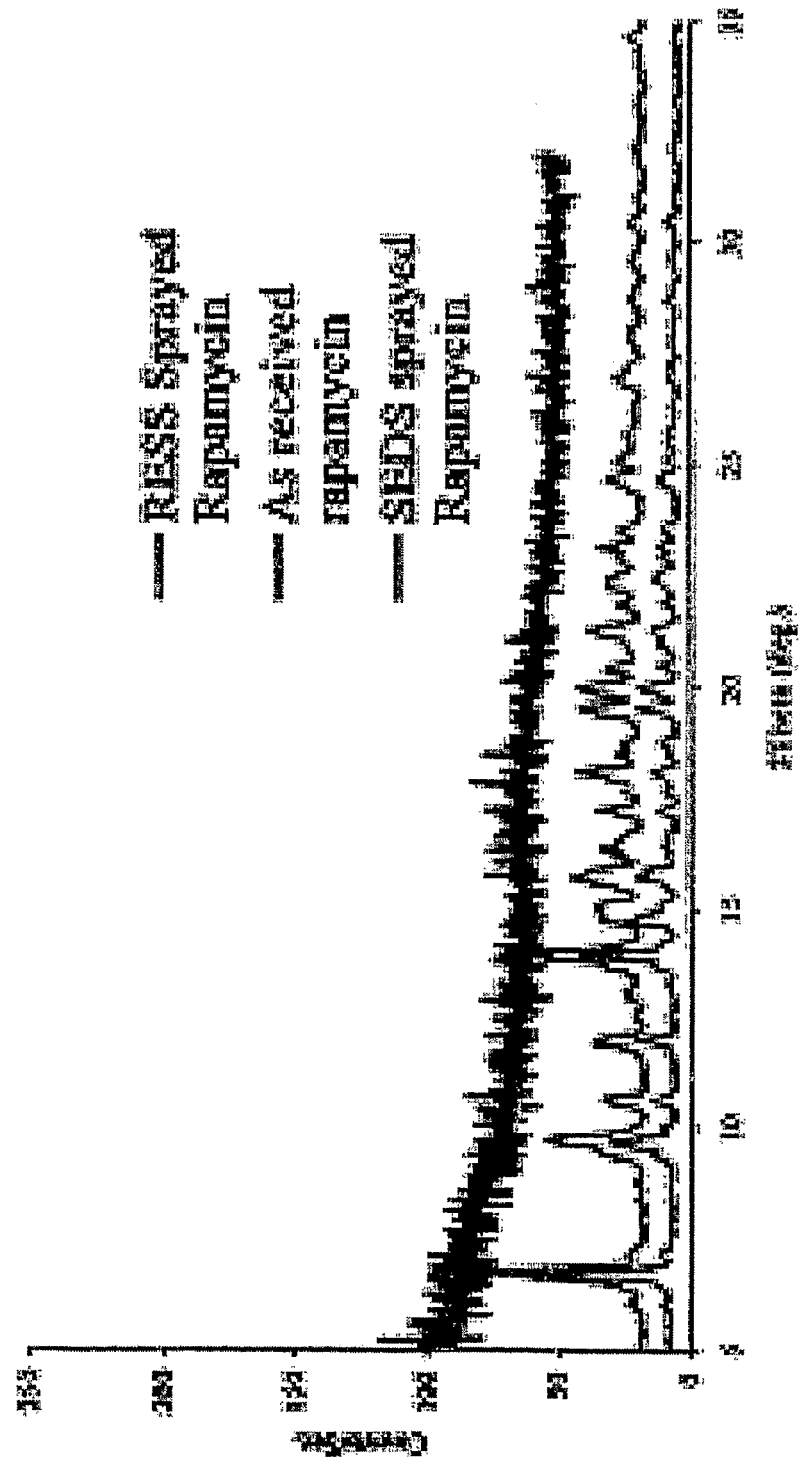
FIG. 8. XRD spectra of rapamycin sprayed in two morphologies compared to an authentic sample.
Figure 9:
FIG. 9. Particle size control.
Figure 10:
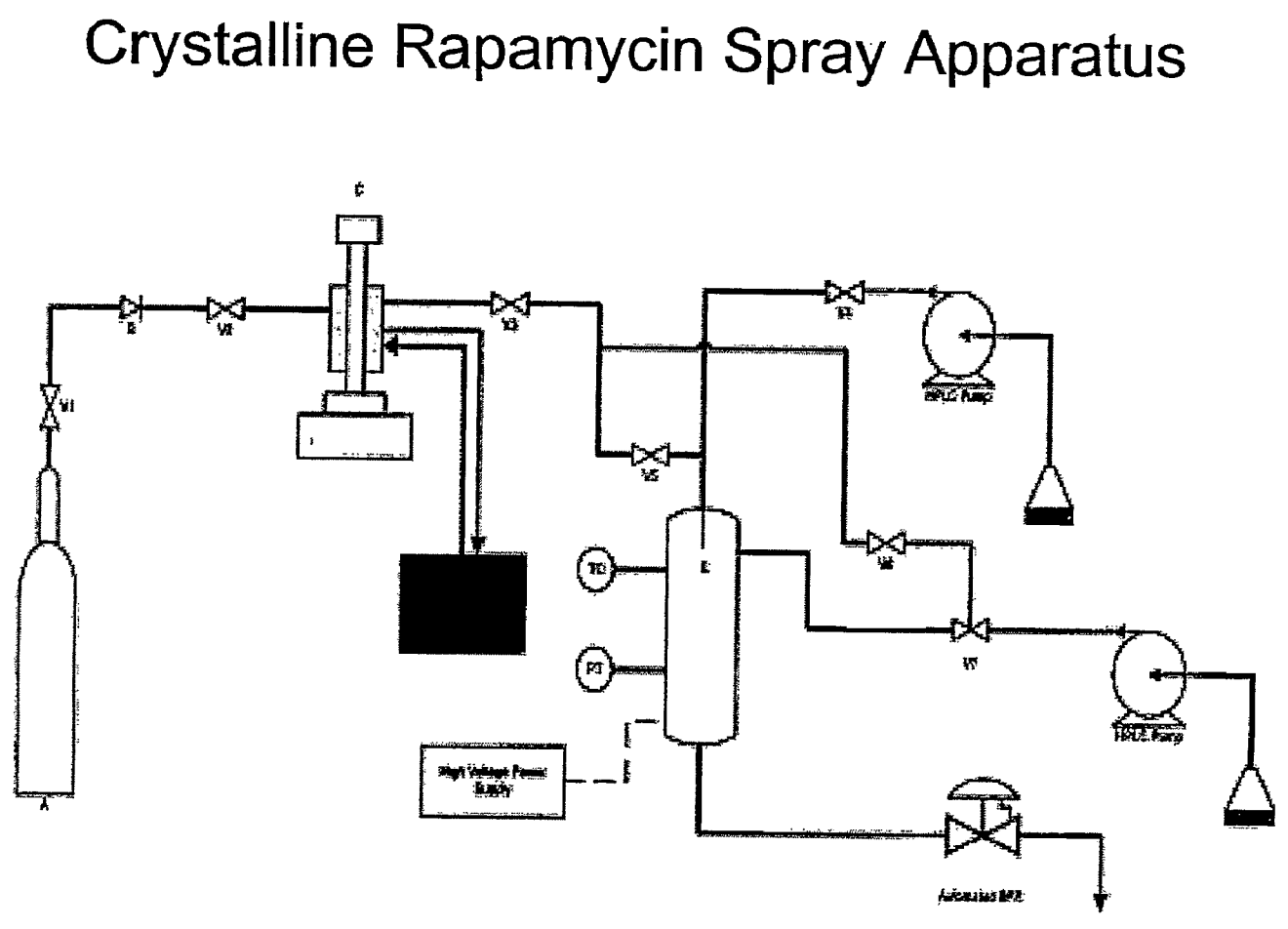
Figure 11:
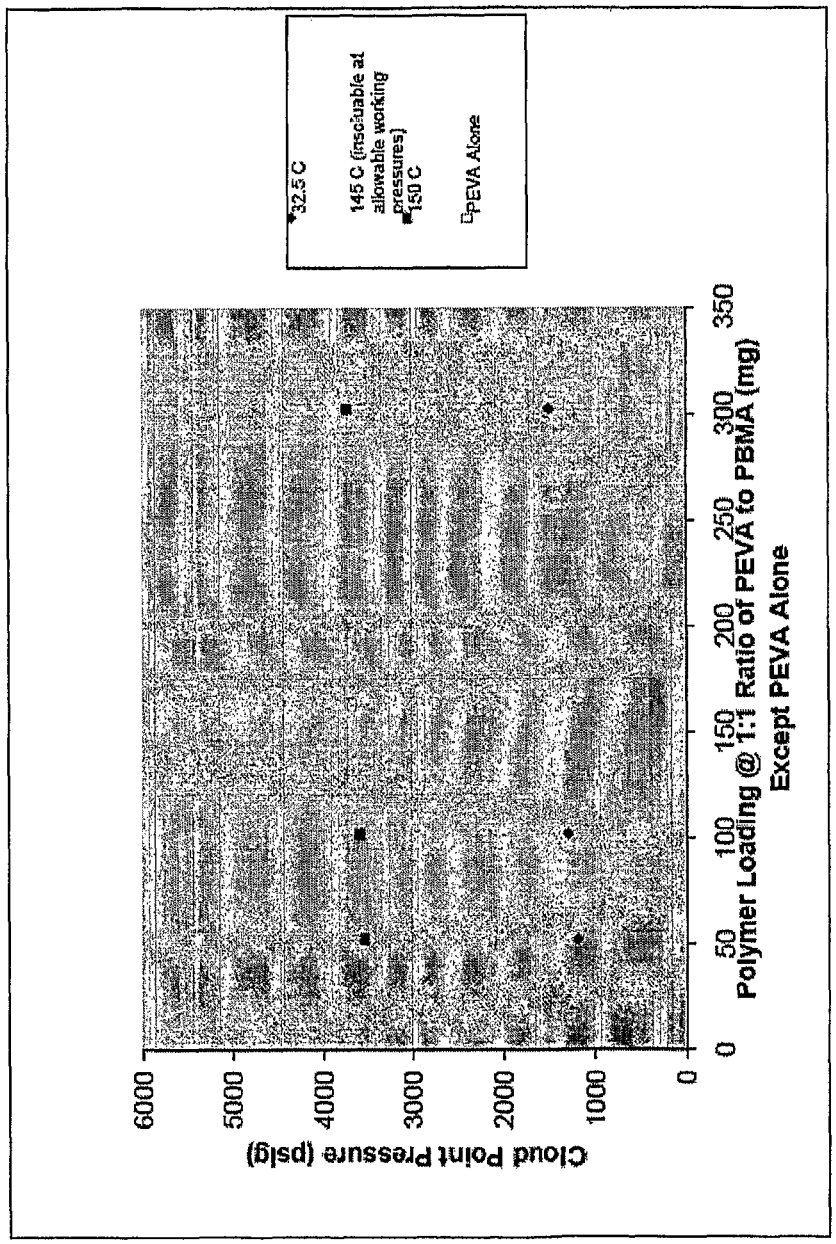
FIG. 11. Cloud point isotherms for polyethylene-co-vinyl acetate (PEVA) and poly(butyl methacrylate) (PMBA) combined as discussed in examples 9, 10, 11 and 12.

The RESS process equipment used in the present studies is depicted in FIG. 1. This is a common design for a RESS apparatus see C. Domingo et al, Journal of Supercritical Fluids 10, 39-55 (1997). The SEDS equipment used in the present studies is depicted in FIGS. 2 and 10. FIG. 2 shows a common SEDS apparatus and FIG. 10 shows a SEDS apparatus using a two-nozzle design with electrostatic capture of the sprayed particles. The nozzle orifice size can be used to control the particle size. FIG. 3 depicts the nozzle design for the SEDS equipment shown in FIGS. 2 and 10. FIG. 4 shows the FTIR spectra of a representative small molecule medically therapeutic agent, two polymers and the mixture of the components. IR stretches specific to each molecule are identified and labeled. FIG. 5 shows implantable medical devices coated with pharmaceutical agent and polymer under various sintering conditions. FIG. 6 shows the infrared spectra of the 3-component coating before and after sintering. The spectra demonstrate that the sintering process does not adversely impact the coating since no new stretches appear in the after sintering spectrum. FIG. 7 shows a wide (left panel) and narrow (right panel) field view of sprayed rapamycin. Both crystalline and amorphous rapamycin are visible in the images. FIG. 8 shows XRD data taken for an authentic rapamycin sample, RESS sprayed rapamycin and SEDS sprayed rapamycin. The RESS sprayed rapamycin lacks any crystallinity indicated by the absence of diffraction peaks in the XRD. SEDS sprayed rapamycin has diffraction peaks that are identical to the authentic sample indicating that the two materials are the same. FIG. 9 demonstrates particle size control using the SEDS process. In the upper left is an optical photograph of a view cell containing a substrate (horizontal line in bottom portion of the window) held at 2500 psi. An SEM micrograph is in the lower left image showing aggregated particles averaging approximately 35 nm in size. The upper right panel in FIG. 9 shows an optical photograph of a view cell pressurized at 1200 psi. The particles are sufficiently large to scatter light as evidenced by the cloud of particles above the substrate in the image. The lower right panel in FIG. 9 shows that the particle size is approximately 20 microns. FIG. 10 shows the SEDS spraying apparatus with a two-nozzle design and novel high voltage power supply used for the electrostatic collection of the SEDS sprayed particles. By operating at voltages below the component with the lowest ionization potential, electrostatic collection of the SEDS sprayed particles can be achieved.

Example 2

General Spray Coating 1

A solution containing a therapeutic chemical compound that is saturated in a solvent or supersaturated in a solvent is sprayed at a flow rate sufficient to achieve flow into a chamber of known volume pressurized above ambient pressure and containing a medical device substrate. The system temperature is held constant or allowed to vary so that any number of points in the phase diagrams of the solution or mixture or any of its individual components can be mapped in pressure-temperature, volume-pressure or pressure-volume space constituting liquid, gas or supercritical $CO_2$ conditions. $CO_2$ in any single phase or combination of phases flows through the chamber at a mass flow rate of 5 gm/min to some multiple of this flow rate. After a period of time ranging from seconds to minutes or hours have elapsed, the solute and solvent flow that is a solution of the therapeutic compound and suitable solvent for the chosen solute or solutes cease but $CO_2$ flow continues for an additional period of time maintaining constant pressure during this period. After this time period, the pressure is dropped to atmospheric pressure. During the spray coating process the particles are attracted to the medical substrate by charging the substrate oppositely to that of the sprayed particle charge by applying a voltage that is greater than 5000 V but less than the ionization potential of the most easily ionized component of the mixture. The particles may also traverse an electromagnetic field such that the field is used to guide the particle to a target.

Example 3

Spray Coating 2

A solution of equal parts of one solvent and another miscible solvent containing therapeutic chemical compound is prepared so that compound is not saturated. This solution is sprayed at a known flow rate ranging from 1 mL/min to 100 mL/min into a chamber of known volume and pressurized above ambient pressure. The system temperature is maintained at a constant level or allowed to vary so that any number of points in the phase diagrams of the solution or mixture or any of its individual components can be mapped in pressure-temperature, volume-pressure or pressure-volume space. $CO_2$ flows through the chamber at a known flow rate. Spraying is stopped after a period of time, but $CO_2$ flow continues for an additional period of time sufficient to ensure that the chamber volume has been turned over or replaced a sufficient number of times to remove any residual solvent or co-solvent from the chamber after which the pressure is reduced to atmospheric pressure. As in the above example, the particles generated in the spray process are collected on the medical substrate electrostatically as they are generated.

Example 4

Spray Coating 3

A therapeutic compound in a crystalline dry powder state is sprayed through a nozzle using dry powder coating process directed toward a stent. From a separate nozzle a $CO_2$ solution containing the polymer and a co-solvent or a polymer solution prepared in a suitable solvent such as dimethyl ether is sprayed toward the stent. The $CO_2$ flow rate is variable. The temperature of the stent and therapeutic chemical compound remain at room temperature or no below room temperature in order to prevent degradation of thermally sensitive therapeutic compounds but the polymer solution temperature is maintained above the solvent critical temperature and pressure so that a supercritical solution or near supercritical solution exists. The particles are electrostatically captured during their generation or as they exit the dry powder spray nozzle as described in the previous examples.

Example 5

Uniform Surface Coating

The ability to uniformly coat arterial stents with controlled composition and thickness using electrostatic capture in a rapid expansion of supercritical solution (RESS) experimental series has been demonstrated. This technique involves spraying an equal part mixture of the therapeutic compound such as rapamycin and polymers such as PBMA and PEVA using a spray coating and collection technique described herein. To determine coating composition, infrared spectroscopy was used to collect the spectrum of a silicon wafer chip coated simultaneously with an arterial stent (FIG. 4). Unique absorption bands were identified for each mixture component and band area was used as a metric to determine incorporation of each compound in the coating.

The individual bands used for compositional analysis were determined by spray coating Si wafer chips with each component separately. The coating thickness was determined gravimetrically and calculated from the density of the materials. It was assumed that the layer is fully dense. The thickness can be controlled by valving the spray time.

In the as sprayed state, the coating lacks strong adhesion to the substrate. Sintering the coated substrate (see FIG. 5) dramatically improves coating adhesion while leaving the components unaltered as the infrared spectra shown in FIG. 6 confirm. The coating is sintered in a supercritical carbon dioxide environment allowing mild sintering conditions to be used with temperature below 80° C.

Example 6

Spray Coating of Crystalline Rapamycin

Several carbon dioxide based spray-coating methods were attempted to spray deposit rapamycin in crystalline form including RESS without successfully controlling rapamycin morphology. One SEDS coating method was successful in spray coating crystalline rapamycin as shown in FIGS. 7 and 8. A solution of 10 parts hexane and 9 parts THF saturated with Rapamycin is sprayed at a flow rate of 0.5 mL/min into a 25 mL chamber pressurized at 82 bar with carbon dioxide. The system temperature is held constant at 25° C. constituting liquid $CO_2$ conditions. $CO_2$ flows through the pressurized chamber at a mass flow rate of 5 gm/min. After 5 minutes have elapsed, the drug and polymer spray cease but $CO_2$ flow continues for an additional 20 minutes maintaining constant pressure during this period. After this time period, the pressure is dropped to atmospheric pressure. The particles are attracted to the substrate by charging the substrate oppositely to the particle charge by applying a voltage that is greater than 5000 V but less than the ionization potential of the most easily ionized component of the mixture.

As the SEM images show in FIG. 7, crystalline rapamycin was deposited on the substrate and the crystal size is approximately 2 microns (right panel in the figure) along its major axis with large crystalline aggregates distributed across the substrate surface (left panel).

The diffraction peaks in the XRD shown in FIG. 8 confirm the identity of the crystals as rapamycin since the sprayed rapamycin (lowest spectrum) matches the as received rapamycin (middle spectrum) peak for peak. XRD results for other failed attempts (upper spectrum) to spray crystalline rapamycin are included for comparative purposes. The amorphous diffraction pattern displayed in the top trace of FIG. 8 was obtained from a RESS sprayed sample and is also representative of failed attempts to spray crystalline rapamycin using SEDS based approaches using only polar or non-polar solvents. The goal of this experimental series was to demonstrate a carbon dioxide technique that could spray rapamycin in crystalline form. No attempt was made to control crystal size, coverage uniformity, or aggregation.

Example 7

Particle Size Control

FIG. 9 shows optical and electron microscope comparison of the SEDS spraying process under different pressure conditions. FIG. 9(a) shows an optical photograph taken of the view cell with $CO_2$ present at 1200 psi and 25° C. The nozzle appears as an angled line at approximately 11 o'clock originating from the left of the view cell. The substrate appears as a horizontal line in the bottom of the view cell. FIG. 9(c) is a scanning electron micrograph of the particles deposited on the substrate that was removed from the view cell in 9(a). The scale of the scanning electron micrograph demonstrates the particle size.

FIG. 9(b) shows an optical photograph taken of the view cell with $CO_2$ present at 2500 psi and 25° C. The nozzle appears as an angled line at approximately 11 o'clock originating from the left of the view cell. The substrate appears as a horizontal line in the bottom of the view cell. FIG. 9(d) is a scanning electron micrograph of the particles deposited on the substrate that was removed from the view cell in 9(b). The scale of the scanning electron micrograph demonstrates the particle size. These images demonstrate an ability to control particle size and morphology. Both these features are important as elution rates can be affected by both parameters.

Example 8

Further Process Equipment

Further equipment is shown in FIG. 10. This apparatus is used to spray rapamycin in crystalline form using a SEDS process with electrostatic capture. The unique features of this apparatus are the dual nozzle design and high voltage pass through permitting electrostatic capture of the sprayed particles. In other respects the design is similar to other SEDS equipment.

The dual nozzle separates polymer and drug spraying from each other which is important as it has been shown that polymers co-sprayed with another component can influence the ability of non polymer component to form particulate in the desired morphology. However, both the components are sprayed into the same chamber allowing the particles to be collected at a single point.

The high voltage pass through permits electrostatic capture of the sprayed components onto the desired substrate.

Example 9

Preparation of Supercritical Solution Comprising, Polyethylene-co-Vinyl Acetate (PEVA) and Polybutyl Methacrylate (PBMA) in Isobutylene 75 mg of PEVA and 75 mg of PBMA are placed in a 25 mL view cell. The view cell is heated to 150° C.

Isobutylene is added to a pressure of 3000 psig. Under these conditions, a clear solution is produced.

Example 10

Preparation of Supercritical Solution Comprising Polyethylene-co-Vinyl Acetate (PEVA) and Polybutyl Methacrylate (PBMA) in Isobutylene 150 mg of PEVA and 150 mg of PBMA are placed in a 25 mL view cell. The view cell is heated to 150° C.

Isobutylene is added to a pressure of 4000 psig. Under these conditions, a clear solution is produced.

Example 11

Preparation of Supercritical Solution Comprising Polyethylene-co-Vinyl Acetate (PEVA) and Polybutyl Methacrylate (PBMA) in Isobutylene and $CO_2$ 75 mg of PEVA and 75 mg of PBMA are placed in a 25 mL view cell and the cell is heated to 150° C.

Isobutylene is added to a pressure of 4000 psig, to produce a clear solution.

10 (v/v %) $CO_2$ is added. The addition of $CO_2$ at this volume percent does not precipitate the dissolved polymer.

Example 12

Preparation of Supercritical Solution Comprising Polyethylene-co-Vinyl Acetate (PEVA) and Polybutyl Methacrylate (PBMA) in Isobutylene and $CO_2$ 150 mg of PEVA and 150 mg of PBMA are placed in a 25 mL view cell and the cell is heated to 150° C.

Isobutylene is added to a pressure of 4000 psig, to produce a clear solution.

10 (v/v %) $CO_2$ is added. The addition of $CO_2$ at this volume percent does not precipitate the dissolved polymer; however addition of $CO_2$ at higher volume fraction leads to polymer precipitation, under these conditions.

Example 13

Dry Powder Rapamycin Coating on an Electrically Charged 316 Stainless Steel Coupon A 1 cm×2 cm stainless steel metal coupon serving as a target substrate for rapamycin coating was placed in a vessel and attached to a high voltage electrode. The vessel (V), of approximately 1500 $cm^3$ volume, was equipped with two separate nozzles through which rapamycin or polymers could be selectively introduced into the vessel. Both nozzles were grounded. Additionally, the vessel (V) was equipped with a separate port was available for purging the vessel. Upstream of one nozzle (D) was a small pressure vessel (PV) approximately 5 $cm^3$ in volume with three ports to be used as inlets and outlets. Each port was equipped with a valve which could be actuated opened or closed. One port, port (1) used as an inlet, was an addition port for the dry powdered rapamycin. Port (2), also an inlet was used to feed pressurized gas, liquid, or supercritical fluid into PV. Port (3), used as an outlet, was used to connect the pressure vessel (PV) with nozzle (D) contained in the primary vessel (V) with the target coupon. Dry powdered Rapamycin obtained from LC Laboratories in a predominantly crystalline solid state, 50 mg milled to an average particle size of approximately 3 microns, was loaded into (PV) through port (1) then port (1) was actuated to the closed position. Gaseous carbon dioxide was then added to (PV) to a pressure of 400 to 600 psig at 20° C. through port (2), then port (2) was closed to the source gas. The metal coupon was then charged to 40 kV using a Glassman Series EL high-voltage power source. Port (3) was then actuated open allowing for the expansion of the pressurized carbon dioxide and rapamycin powder into the vessel (V) while the coupon remained charged. After approximately 60-seconds the voltage was eliminated and the coupon was isolated. Upon visual inspection of the coupon using an optical microscope it was determined that the entire surface area of the coupon, other than a small portion masked by the voltage lead, was covered in a relatively even distribution of powdered material. X-ray diffraction (XRD) confirmed that the powdered material was largely crystalline in nature as deposited on the metal coupon. UV-Vis and FTIR spectroscopy confirmed that the material deposited on the coupon was rapamycin.

Example 14

Dry Powder Rapamycin Coating on a 316-Stainless Steel Coupon with no Electrical Charge A coupon was coated in an identical fashion to what was described in Example 13. However, no voltage was applied to the coupon throughout the dry powder-coating run. After expansion of the carbon dioxide and the powdered rapamycin into vessel (V), and a period of roughly 60 seconds, the coupon was isolated and evaluated. The coupon was analyzed using an optical microscope and showed some dry powder material on much of the surface of the coupon. However, the coverage of drug on the surface was much lower than in example 1 and there was notably more variability in coverage at different locations on the coupon surface. The total powder coating was estimated to be about ⅓rd the amount determined to be crystalline rapamycin in example 1.

Example 15

Polymer Coating on an Electrically Charged 316-Stainless Steel Coupon Using Rapid Expansion from a Liquefied Gas A coating apparatus as described in example 13 above was used in the foregoing example. In this example the second nozzle, nozzle (P), was used to feed precipitated polymer particles into vessel (V) to coat a 316-stainless steel coupon. Nozzle (P) was equipped with a heater and controller to minimize heat loss due to the expansion of liquefied gases. Upstream of nozzle (P) was a pressure vessel, (Pv2), with approximately 25-cm3 internal volume. The pressure vessel (PV2) was equipped with multiple ports to be used for inlets, outlets, thermocouples, and pressure transducers. Additionally, (PV2) was equipped with a heater and a temperature controller. Each port was connected to the appropriate valves, metering valves, pressure regulators, or plugs to ensure adequate control of material into and out of the pressure vessel (PV2). One outlet from (PV2) was connected to a metering valve through pressure rated tubing which was then connected to nozzle (P) located in vessel (V). In the experiment, 75 mg of polyethylene-co-vinyl acetate (PEVA) obtained from Aldrich Chemical Company with approximately 33-weight percent vinyl acetate and 75 mg of poly (butyl methacrylate) (PBMA) also obtained from Aldrich Chemical Company were added to pressure vessel (PV2). Dichlorofluoromethane, 20.0 grams, was added to the pressure vessel (PV2) through a valve and inlet. Pressure vessel (PV2) was then heated to 40° C. bringing the pressure inside the isolated vessel to approximately 40 psig. Nozzle (P) was heated to 120° C. After sufficient time to dissolve the two polymers in the liquefied gas inside (PV2), the vessel (PV2) was over-pressurized with helium to approximately 200 psig using a source helium tank and a dual stage pressure regulator. See U.S. Pat. No. 6,905,555 for a description of Helium displacement art. A 1-cm×2-cm 316-stainless steel coupon was placed into vessel (V) and attached to an electrical lead. Nozzle (P) was attached to ground. The coupon was charged to 40 kV using a Glassman high-voltage power source at which point the metering valve was opened between (PV2) and nozzle (P) in pressure vessel (PV). Polymer dissolved in liquefied gas and over-pressurized with helium to 200 psig was fed at a constant pressure of 200 psig into vessel (V) maintained at atmospheric pressure through nozzle (P) at an approximate rate of 3.0 cm$^3$/min. After approximately 5 seconds, the metering valve was closed discontinuing the polymer-solvent feed. Vessel (V) was purged with gaseous $CO_2$ for 30 seconds to displace chlorofluorcarbon. After approximately 30 seconds, the metering valve was again opened for a period of approximately 5 seconds and then closed. This cycle was repeated about 4 times. After an additional 1-minute the applied voltage to the coupon was discontinued and the coupon was removed from pressure vessel (V). Upon inspection by optical microscope, a polymer coating was evident as evenly distributed on all non-masked surfaces of the coupon. Dissolution of the polymer mixture from the surface of the coupon followed by quantification using standardized quantitative FT-IR methods determined a composition of approximately 1:1 PEVA to PBMA on the coupon.

Example 16

Dual Coating of a Metal Coupon with Crystalline Rapamycin, and 1:1 Mixture of Polyethylene-co-Vinyl Acetate (PEVA) and Poly(Butyl Methacrylate) (PBMA)

An apparatus described in example 13 and further described in example 15 was used in the foregoing example. In preparation for the coating experiment, 25 mg of crystalline powdered rapamycin with an average particle size of 3-microns was added to (PV) through port (1), then port (1) was closed. Then, (PV) was pressurized to 400-600 psig with gaseous carbon dioxide at 20° C. through port (2), prior to closing port (2). Next, 75 mg of polyethylene-co-vinyl acetate (PEVA) with approximately 33-weight percent vinyl acetate and 75 mg of poly(butyl methacrylate) (PBMA) were added to pressure vessel (PV2). Dichlorofluoromethane, 20.0 grams, was added to the pressure vessel (PV2) through a valve and inlet. Pressure vessel (PV2) was then heated to 40° C. bringing the pressure inside the isolated vessel (PV2) to approximately 40 psig. Nozzle (P) was heated to 120° C. After sufficient time to dissolve the two polymers in the liquefied gas, the vessel was over-pressurized with helium to approximately 200 psig using a source helium tank and a dual stage pressure regulator. A 1-cm×2-cm 316-stainless steel coupon was added to vessel (V) and connected to a high-voltage power lead. Both nozzles (D) and (P) were grounded. To begin, the coupon was charged to 40 kV after which port (3) connecting (PV) containing rapamycin to nozzle (D) was opened allowing expansion of carbon dioxide and ejection of rapamycin into vessel (V) maintained at ambient pressure. After closing port (3) and approximately 60-seconds, the metering valve connecting (PV2) with nozzle (P) inside vessel (V) was opened allowing for expansion of liquefied gas to a gas phase and introduction of precipitated polymer particles into vessel (V) while maintaining vessel (V) at ambient pressure. After approximately 5-seconds at a feed rate of approximately 3 cm$^3$/min., the metering valve was closed while the coupon remained charged. Port (1) was then opened and an additional 25-mg of powdered crystalline rapamycin was added to (PV), and then port (1) was closed. Pressure vessel (PV) was then pressurized with liquid carbon dioxide to 400-600 psig through port (2), after which port (2) was again closed. Maintaining the coupon at an applied voltage of 40 kV, port (3) was again opened to nozzle (D) allowing for the expansion of carbon dioxide to a gas and the ejection of the powdered crystalline drug into the vessel (V). After and additional 60-seconds, the metering valve between (PV2) and nozzle (P) was again opened allowing for the expansion of the liquefied solvent to a gas into vessel (V) and the precipitation of polymer particles also in vessel (V). The sequential addition of drug followed by polymer or polymer followed by drug as described above was repeated for a total of four (4) cycles after which the applied potential was removed from the coupon and the coupon was removed from the vessel. The coupon was then examined using an optical microscope. A consistent coating was visible on all surfaces of the coupon except where the coupon was masked by the electrical lead. The coating appeared conformal but opaque and somewhat granular at high magnification.

Example 17

Dual Coating of a Metal Coupon with Crystalline Rapamycin, and 1:1 Mixture of Polyethylene-co-Vinyl Acetate (PEVA) and Poly(Butyl Methacrylate) (PBMA) Followed by Supercritical Carbon Dioxide Annealing or Gaseous Carbon Dioxide Annealing After inspection of the coupon created in example 16, the coated coupon was carefully placed in a pressure vessel that was pressurized with carbon dioxide to a pressure of 4500 psig and at a temperature of 60° C. This $CO_2$ sintering process was done to enhance the physical properties of the film on the coupon. The coupon remained in the vessel under these conditions for approximately 3 hours after which the supercritical $CO_2$ was slowly vented from the pressure vessel and then the coupon was removed and reexamined under an optical microscope. The coating was observed to be conformal, consistent, and semi-transparent as opposed to the opaque coating observed and reported in example 16 without dense carbon dioxide treatment. The coated coupon was then submitted for x-ray diffraction (XRD) analysis which confirmed the presence of crystalline rapamycin in the polarizer matrix.

Example 18

Dual Coating of a Metal Cardiovascular Stent with Crystalline Rapamycin, and 1:1 Mixture of Polyethylene-co-Vinyl Acetate (PEVA) and Poly(Butyl Methacrylate) (PBMA)

The apparatus described in examples 13, 15, and 16 above was used in the foregoing example. The metal stent used was a Tristar™ Coronary Stent of a nominal size of 3 mm by 13 mm. The stent was coated in an identical fashion to the coupon described in example 16 above. The stent was coated in an alternating fashion whereby the first coating layer of drug was followed by a thin layer of polymer. These two steps, called a drug/polymer cycle, were repeated 3-times so that the last applied coating layer was polymer. After completion of the coating step, the stent was removed from the vessel (V) and placed in a small pressure vessel where it was exposed to supercritical $CO_2$ as described above in example 16. After this low temperature annealing step, the stent was removed and examined using an optical microscope. The stent was then analyzed using a scanning electron microscope (SEM) equipped with a fast ion bombarding (FIB) device to provide cross-sectional analysis of the coated stent. The SEM micrograph at multiple locations on the stent indicated a completely conformal coating of between 6 and 15-microns in thickness. Evidence of rapamycin crystallites was also apparent in the micrographs.

Example 19

Layered Coating of a Cardiovascular Stent with an Anti-Restenosis Therapeutic and Polymer in Layers to Control Drug Elution Characteristics A cardiovascular stent is coated using the methods described in examples 17 and 18 above. The stent is coated in such as way that the drug and polymer are in alternating layers. The first application to the bare stent is a thin layer of a non-resorbing polymer, approximately 2-microns thick. The second layer is a therapeutic agent with anti-restenosis indication. Approximately 35 micrograms are added in this second layer. A third layer of polymer is added at approximately 2-microns thick, followed by a fourth drug layer which is composed of about 25 micrograms of the anti-restenosis agent. A fifth polymer layer, approximately 1-micron thick is added to stent, followed by the sixth layer that includes the therapeutic agent of approximately 15-micrograms. Finally, a last polymer layer is added to a thickness of about 2-microns. After the coating procedure, the stent is annealed using carbon dioxide as described in example 16 above. In this example a drug eluting stent (DES) is described with low initial drug "burst" properties by virtue of a "sequestered drug layering" process, not possible in conventional solvent-based coating processes. Additionally, by virtue of a higher concentration of drug at the stent 'inter-layer' the elution profile is expected to reach as sustained therapeutic release over a longer period of time.

Example 20

Layered Coating of a Cardiovascular Stent with an Anti-Restenosis Therapeutic and an Anti-Thrombotic Therapeutic in a Polymer Matrix A cardiovascular stent is coated as described in example 19 above. In this example, after a first polymer layer of approximately 2-microns thick, a drug with anti-thrombotic indication is added in a layer of less than 2-microns in thickness. A third layer consisting of the non-resorbing polymer is added to a thickness of about 4-microns. Next another drug layer is added, a different therapeutic, with an anti-restenosis indication. This layer contains approximately 100 micrograms of the anti-restenosis agent. Finally, a polymer layer approximately 2-microns in thickness is added to the stent. After coating the stent is treated as described in example 16 to anneal the coating using carbon dioxide.

Example 22

Coating of Stents with Rapamycin, Polyethylene-co-Vinyl Acetate (PEVA) and Polybutyl Methacrylate (PBMA)

Figure 12:
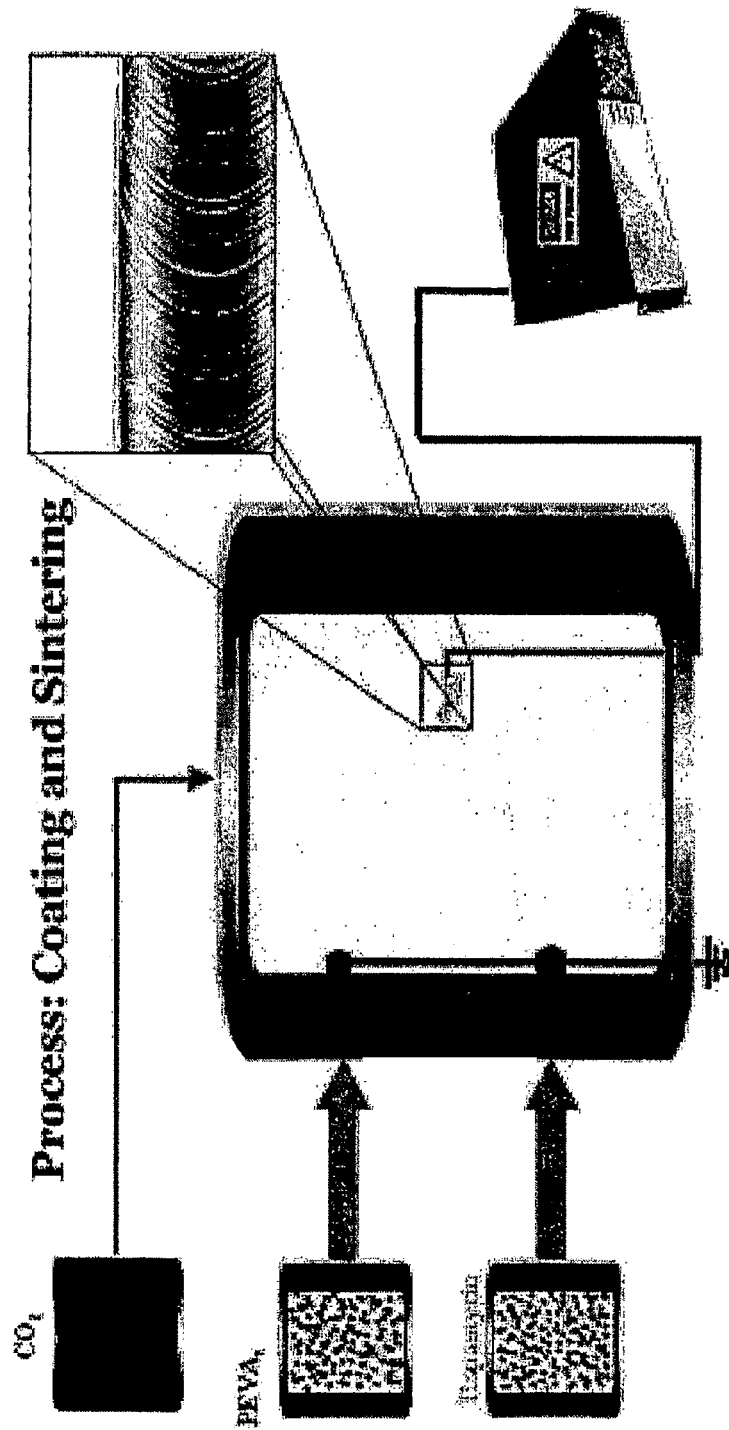
FIG. 12. Schematic Representation of the Coating and Sintering Process Apparatus, as discussed in example 9.

Micronized Rapamycin was purchased from LC Laboratories. PBMA (Mw=~237 k) and PEVA (33% vinyl acetate content) were purchased from Aldrich Chemicals. Two kinds of stents were used: 3 mm TriStar® from Guidant and 6 cell×8-mm, BX Velocity® from Cordis. The stents were coated by dr electrostatic capture followed by supercritical fluid sintering, using 3 stents/coating run and 3 runs/data set. The coating apparatus is represented in FIG. 12. Analysis of the coated stents was performed by multiple techniques on both stents and coupons with relevant control experiments.

In this example a 1:1 ratio of PEVA and PBMA is dissolved in a Dichlorofluoromethane ($CCl_2FH$), which is a compressed gas solvent known to be in the class of "Freon" chemicals. The physical properties of this particular Freon are as follows:

BP=8.9 C
Tc=178.33 C
Pc=751.47 psig
Dc=0.526014 g/cc

A solution was formed by mixing 30 mg of the combined polymers per gram dichlorofluoromethane. The solution was then maintained at 60° C. at vapor pressure (approx 28 psig) until the solution was ready to spray. The solution was then pressurized by adding an immiscible gas to the top of the vessel—typically Helium. Adding Helium compressed the Freon+polymer solution up to 700 (+/−50 psig), which resulted in a compressed fluid. The polymer-Freon solution was then pushed through a nozzle having an inner diameter of 0.005" by continuous addition of Helium into the vessel. The solvent (dichlorofluoromethane) is rapidly vaporized coming out of the nozzle (which is heated to 120° C.), as its boiling point is significantly below room temperature.

Figure 13:
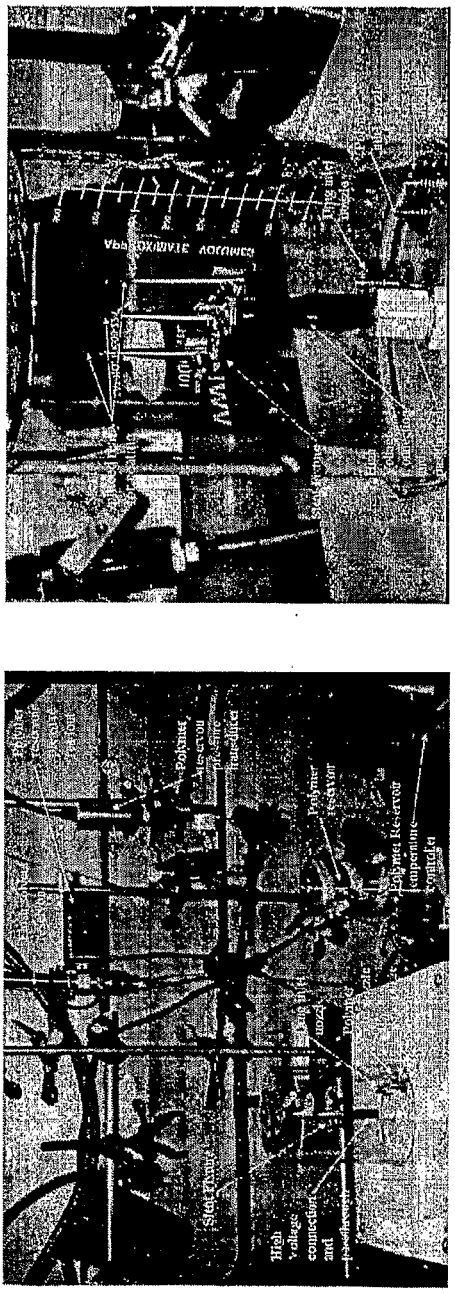
FIG. 13. Detailed images of the coating and sintering process apparatus, as discussed in example 9.
Figure 13:
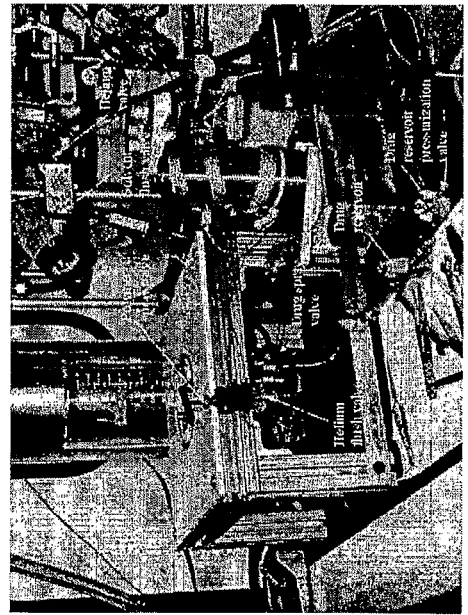

The Drug is deposited by dry powder spray coating. Between 10-30 mg of drug are charged into a small volume of tubing, which is then pressurized with gaseous $CO_2$ to 400 psig. The mixture flows through a nozzle having an inner diameter of 0.187" into the coating vessel where the stents are held. During electrostatic deposition, the stent is charged and the nozzles are grounded. FIGS. 12 and 13 show the apparatus used for the coating and sintering process.

Example 23

Optical Microscopy Analysis of Rapamycin PEVA/PBM Coated Stents

Figure 14:
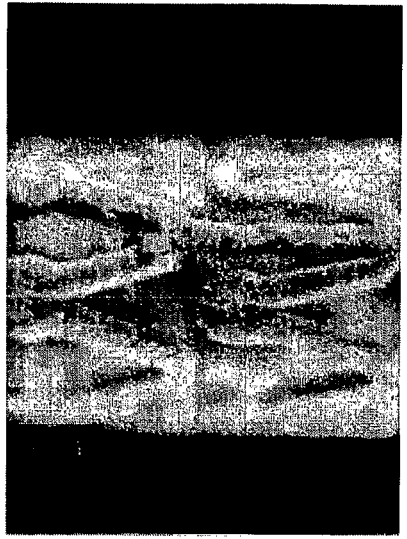
FIG. 14. Drug-Polymer coated coronary stent (a) immediately after deposition, (b) after annealing in a dense carbon dioxide environment at 40° C. The photographs correspond to the experiment discussed in example 10.
Figure 14:
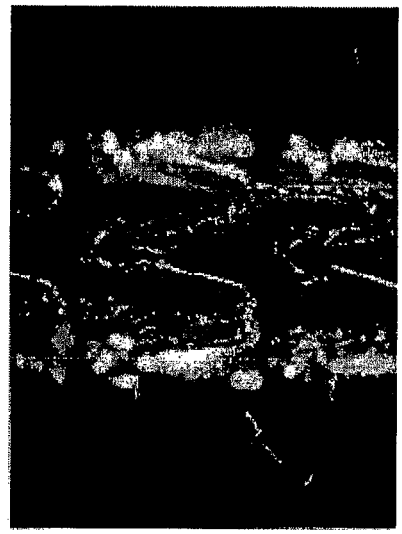
Figure 15:
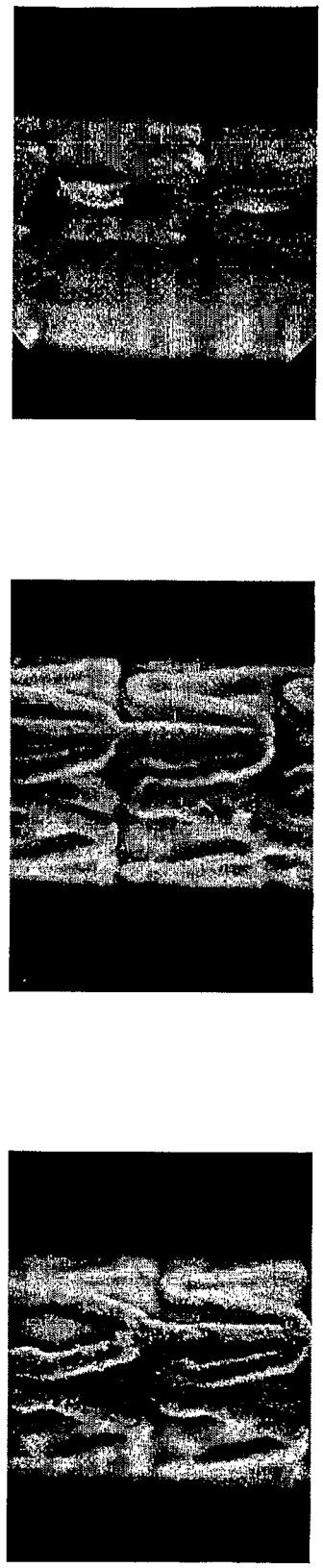
FIG. 15. 40× Magnified Images of Rapamycin/PEVA/PBMA Coated Stents, Obtained From an Optical Microscope with Back and Side Lighting, Showing the Outside, Edge and Inside Surfaces, (a) before and (b) after sintering, as discussed in example 10.
Figure 15:
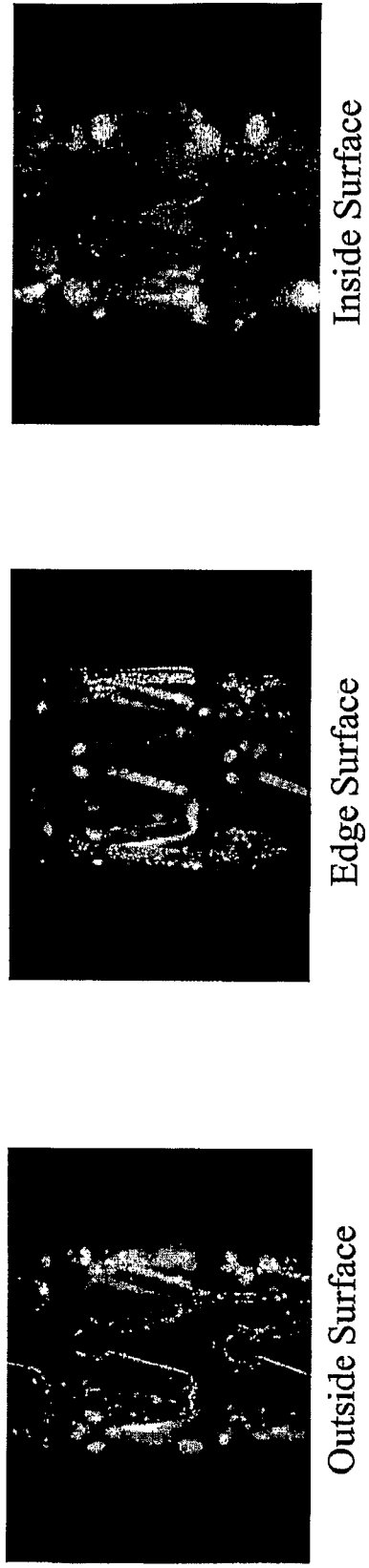
Figure 16:
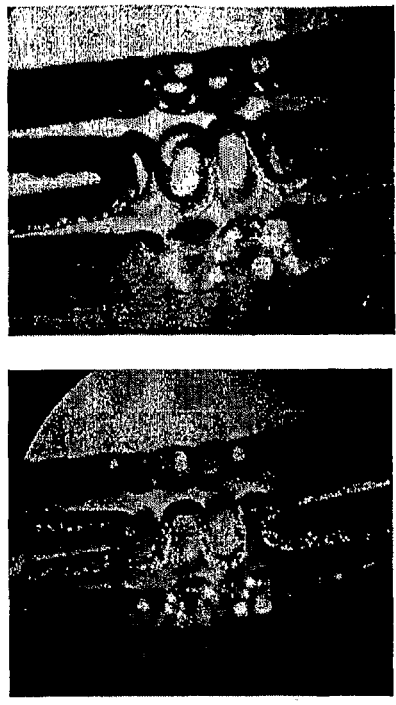
FIG. 16. 40× Magnified Images of Rapamycin/PEVA/PBMA Coated Stents, Obtained From an Optical Microscope with Back and Side Lighting, Showing the Outside and Inside Surfaces, (a) before and (b) after sintering, as discussed in example 10.
Figure 16:
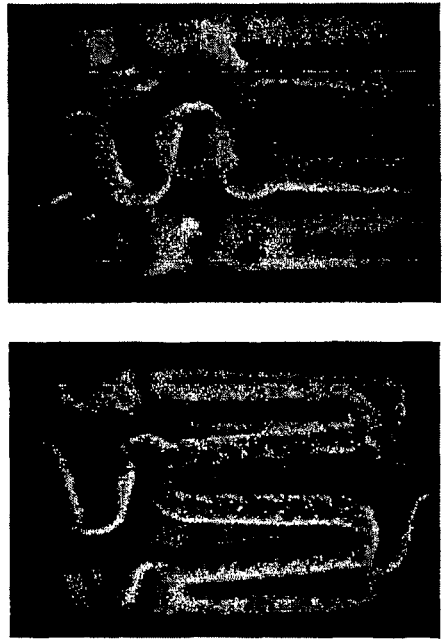
Figure 17:
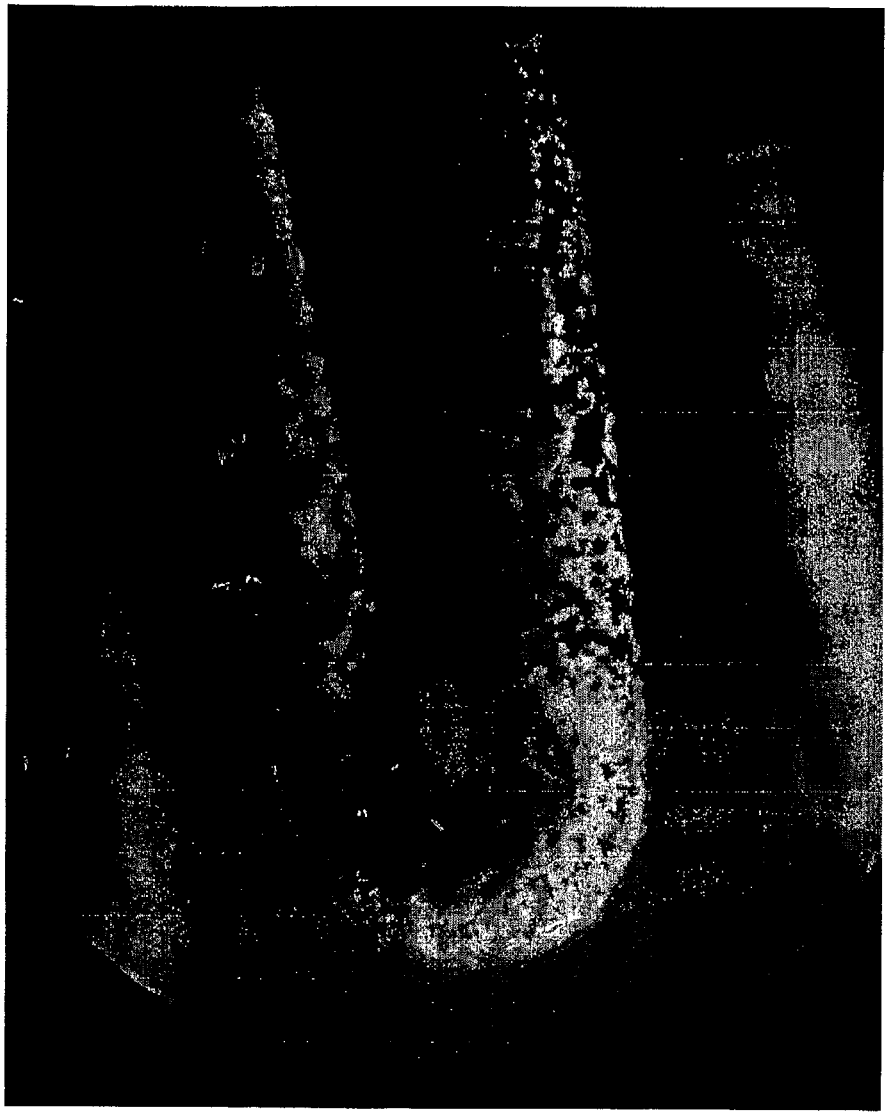
FIG. 17. 100× Magnified Image of a Rapamycin/PEVA/PBMA Coated Stent, Obtained From an Optical Microscope. Crystalline drug is clearly visible embedded within a highly uniform polymer coating, as discussed in example 10.

The stents produced in example 22 were examined by optical microscopy, at 40× magnification with back and side lighting. This method was used to provide a coarse qualitative representation of coating uniformity and to generally demonstrate the utility of the low-temperature $CO_2$ annealing step. The resulting photos shown in FIG. 14, demonstrate the differences in appearance (a) before and (b) after annealing in dense carbon dioxide at 40° C. Photos of the outside, edge and inside surfaces are presented in FIG. 15(a), prior to sintering, which clearly shows nanoparticle deposition equally on all surfaces of the stent, and 15(b) after sintering, with the film showing a smooth and optically transparent polymer. FIG. 16 shows additional 40× magnified images of Rapamycin/PEVA/PBMA coated stents, showing the outside and inside surfaces, (a) before sintering, further demonstrating the nanoparticle deposition equally on all surfaces of the stent and (b) after sintering, showing a smooth and optically transparent polymer film. FIG. 17 shows a 100× magnified mages of Rapamycin/PEVA/PBMA Coated Stents. Crystalline drug is clearly visible embedded within a highly uniform polymer coating.

Example 24

Scanning Electron Microscopy Analysis of Rapamycin/PEVA/PBM Coated Stents

Figure 18:
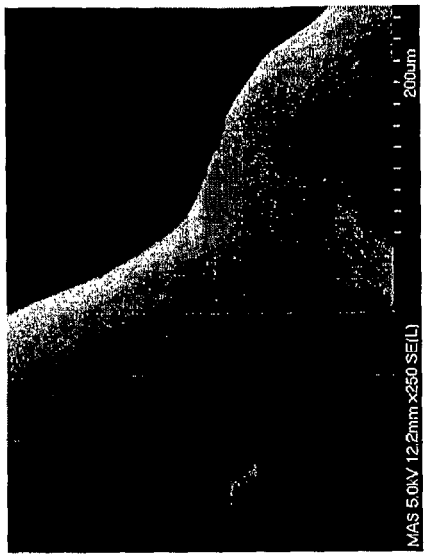
FIG. 18. Scanning Electron Microscope Images of Rapamycin/PEVA/PBMA Coated Stents, at (a) ×30 magnification, (b) ×250 magnification, (c) ×1000 magnification and (d) ×3000 magnification, as discussed in example 11.
Figure 18:
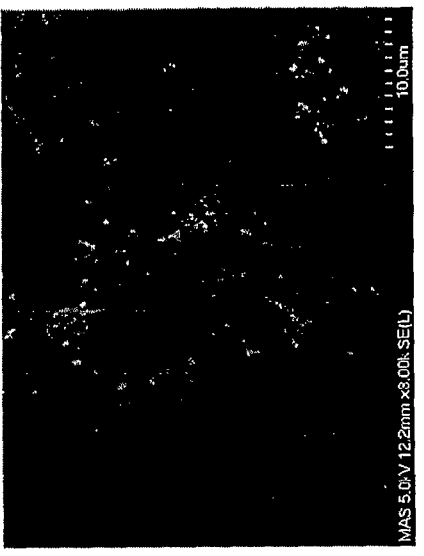
Figure 18:
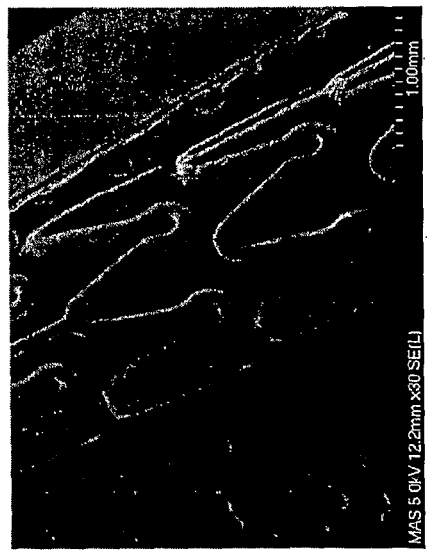
Figure 18:
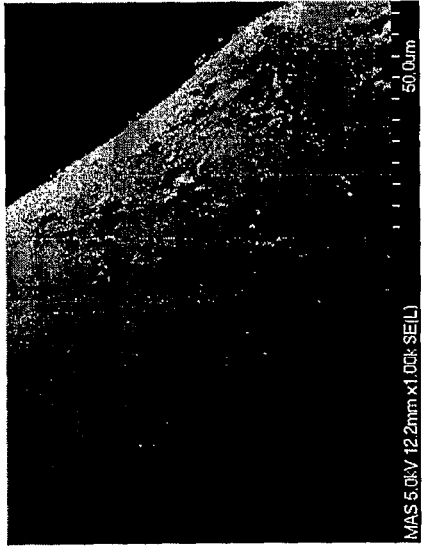

The stents produced in example 21 were examined by scanning electron microscopy, and the resulting images presented in FIG. 18 at (a) ×30 magnification, (b) ×250 magnification, (c) ×1000 magnification and (d) ×3000 magnification. Clearly the nanoparticles have been sintered to an even and conformal film, with a surface topology of less than 5 microns, and demonstrate clear evidence of embedded crystalline rapamycin.

Figure 19:
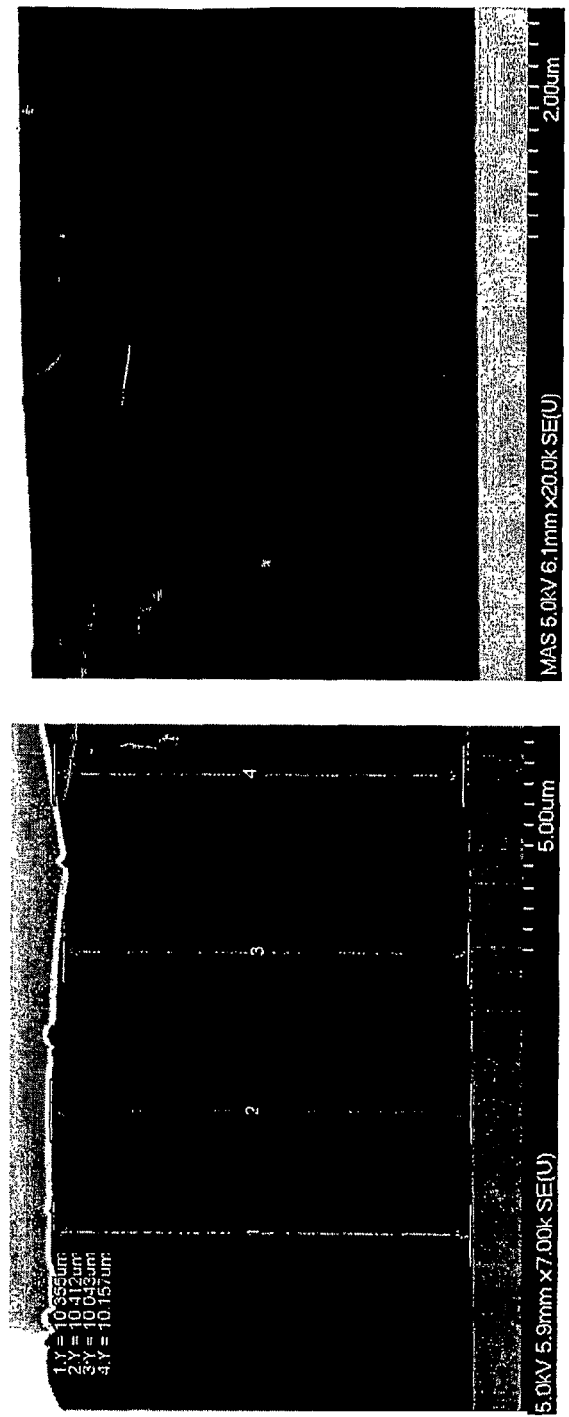
FIG. 19. Cross-sectional Scanning Electron Microscope Images of Rapamycin/PEVA/PBMA Coated Stents at (a) ×7000 magnification and (b) ×20000 magnification. Four cross-sectional thicknesses measured: (1) 10.355 μM; (2) 10.412 μM; (3) 10.043 μM and (4) 10.157 μM, providing a calculated average thickness of 10.242 μM±2%, also discussed in example 11.

Cross-sectional (FIB) images were also acquired and are shown in FIG. 19(a) at 7000× and (b) 20000× magnification. An even coating of consistent thickness is visible. Four cross-sectional thicknesses were measured: (1) 10.355 μM, (2) 10.412 μM, (3) 10.043 μM and (4) 10.157 μM, to give an average thickness of 10.242 μM, with only 2% (±0.2 μM) variation.

Example 25

Differential Scanning Calorimetry (DSC) of Rapamycin/PEVA/PBM Coated Stents

Figure 20:
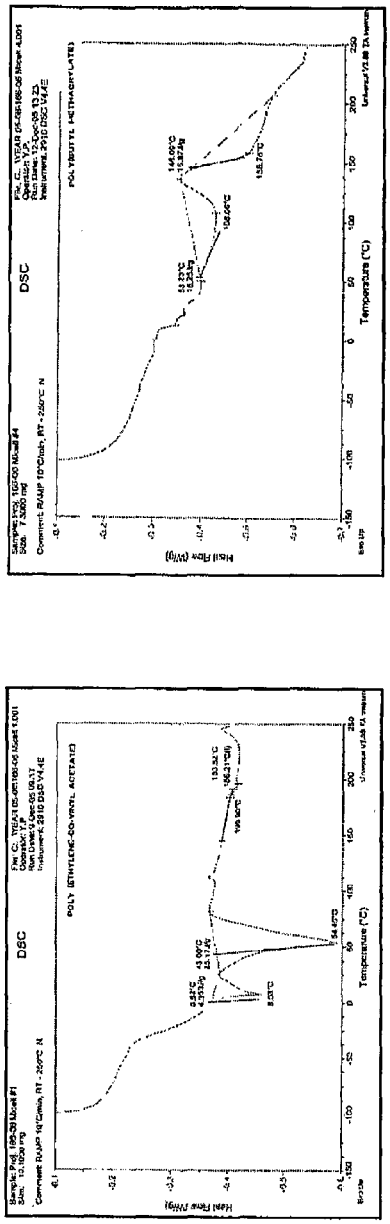
FIG. 20. Differential Scanning Calorimetry (DSC) of (a) PEVA Control, (b) PBMA Control, (c) Rapamycin Control and (d) Coated Rapamycin, PEVA, PBMA Mixture. The Rapamycin crystalline melt at 185-200° C. is indicated in (c) and (d), as discussed in example 12.
Figure 20:
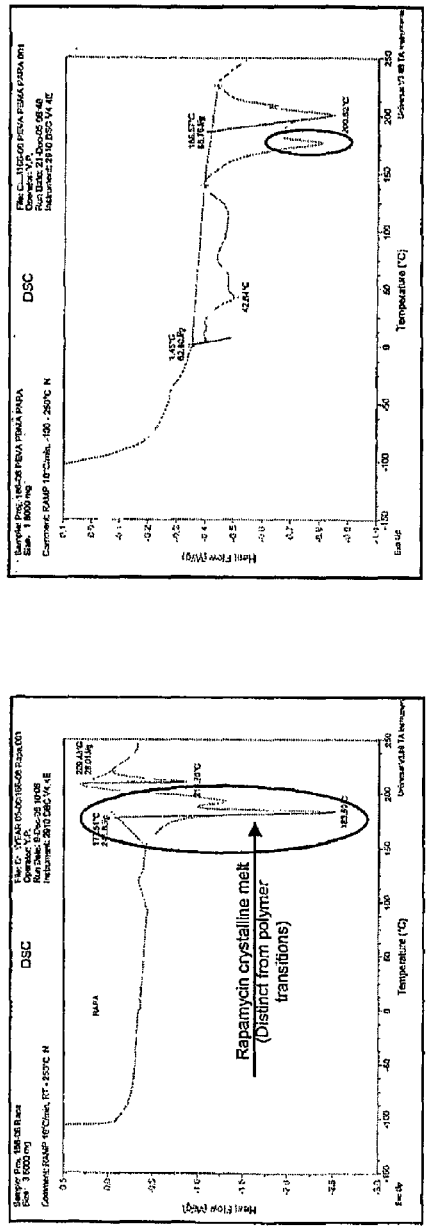

The stents produced in example 21 were examined by Differential Scanning Calorimetry (DSC). Control analyses of PEVA only, PBMA only and Rapamycin only are shown in FIG. 20(a), (b) and (c) respectively. The DSC of the Rapamycin, PEVA and PBMA coated stent is shown in FIG. 20(d). The rapamycin crystalline melt is clearly visible at 185-200° C. and distinct from those of the polymers.

Example 26

X-Ray Diffraction (XRD) of Rapamycin/PEVA/PBM Coated Stents

Figure 21:
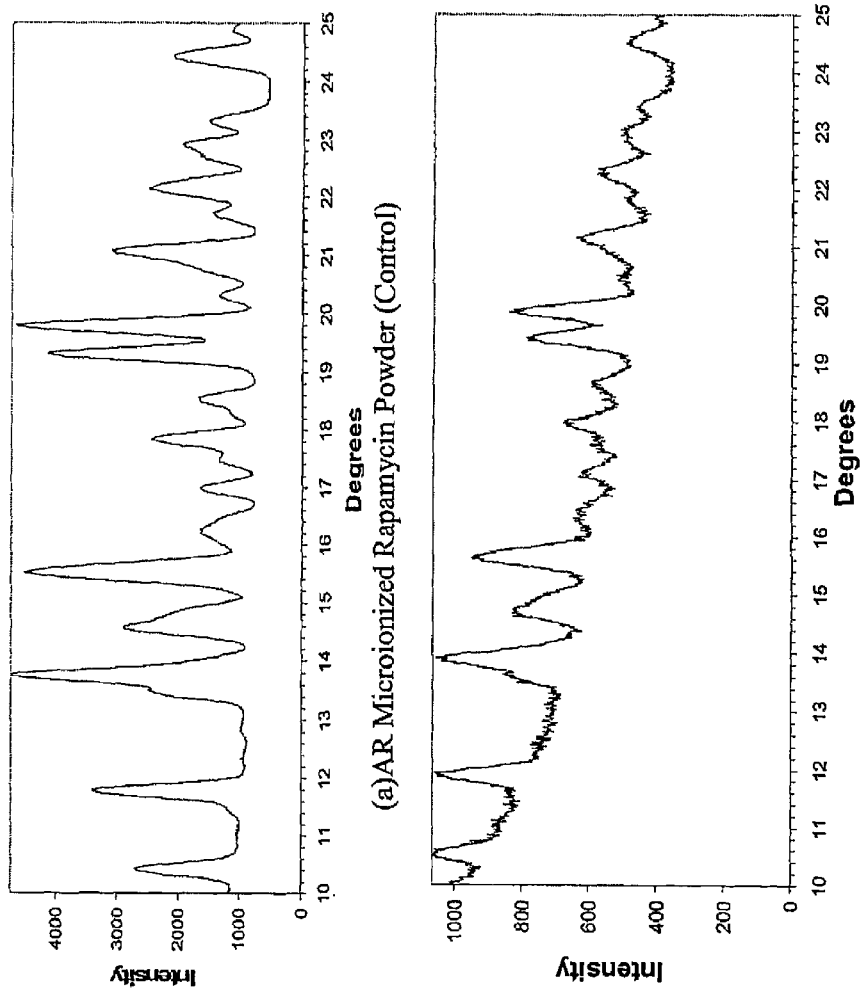
FIG. 21. X-Ray Diffraction of (a) Microionized Rapamycin Powder (Control) and (b) Coated Sintered Rapamycin/PEVA/PBMA Stents, as discussed in example 13.

The stents produced in example 21 were examined by X-Ray Diffraction (XRD). The control spectrum of microionized Rapamycin powder is shower in FIG. 21(a). The XRD of the Rapamycin, PEVA and PBMA coated, sintered stent is shown in FIG. 21(b), showing that the Rapamycin remains crystalline (~64%) throughout the coating and sintering process.

Example 27

Confocal Raman Analysis of Rapamycin/PEVA/PBM Coated Stents

Figure 22:
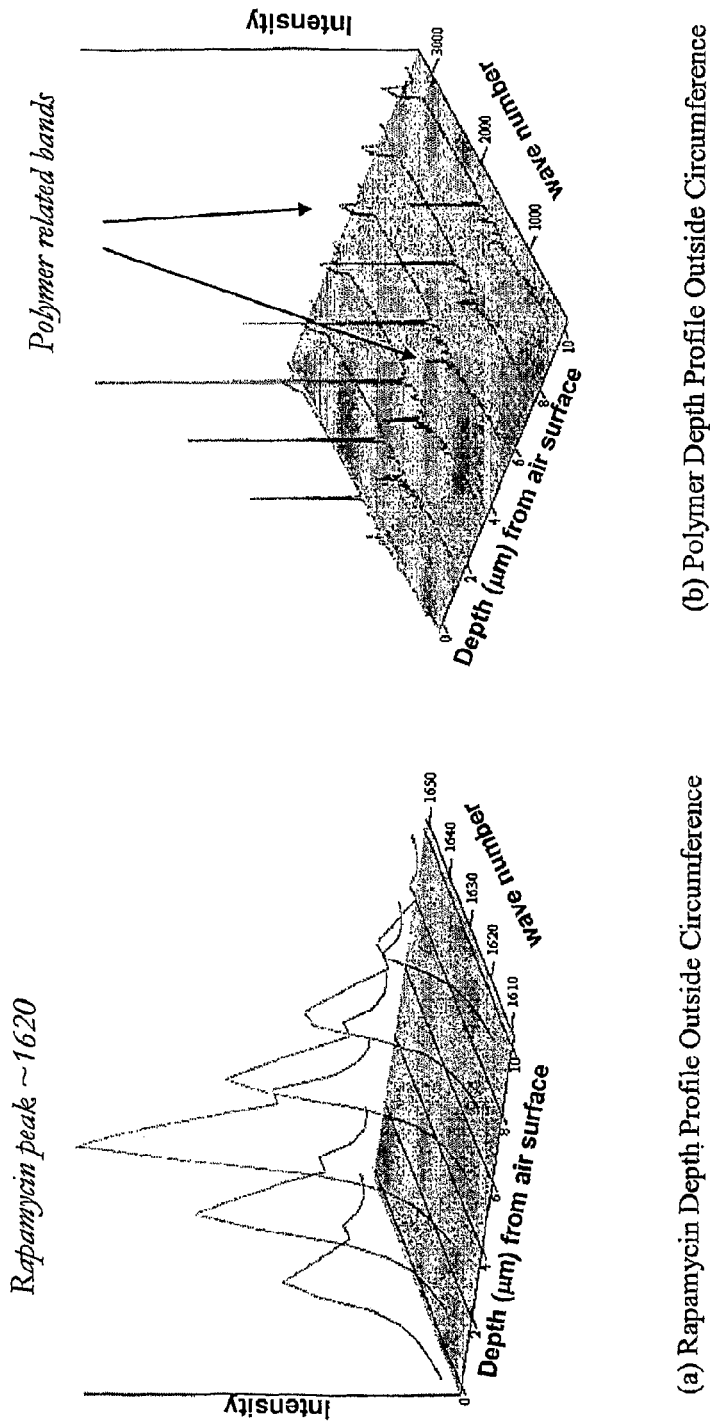
FIG. 22. Confocal Raman Analysis of Rapamycin/PEVA/PBMA Coated Stents (i.e. Depth Profiling from Coating Surface to Metal Stent), highlighting (a) Rapamycin Depth Profile Outside Circumference and (b) Polymer Depth Profile Outside Circumference, as discussed in example 14.

The stents produced in example 21 were examined by Confocal Raman Analysis, to provide depth profiling from the coating surface down to the metal stent. FIG. 22(a) shows the Rapamycin depth profile outside circumference (Rapamycin peak at ~1620) and 22(b) shows the polymer depth profile outside circumference, clearly demonstrating that the drug is distributed throughout polymer coated stents. The highest drug content appears in the center of the polymer coating (~4 μM from the air surface), which is controllable, via the coating and sintering conditions used. In certain embodiments of the invention, the drug would be close to the air surface of the coating. In other embodiments, the drug would be closer to the metal stent. In other embodiments, more than one drug would be deposited in the coating, wherein one drug would be closer to the air surface and another drug would be closer to the metal surface. In yet other embodiments, the drugs would be distributed together throughout the coating.

Example 28

Figure 23:
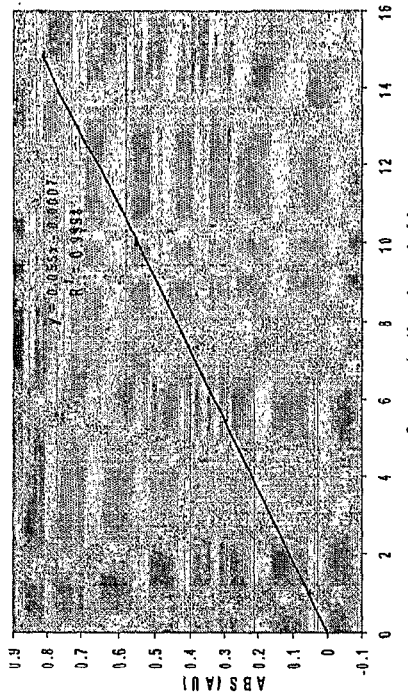
FIG. 23. (a) Rapamycin UV-Vis Spectrum and (b) Calibration Curve at 277 nm. (c) PEVA/PBMA FT-IR Spectrum, (d) PEVA Calibration Curve at 1050 nm and (e) PBMA Calibration Curve at 1285 nm.
Figure 23:
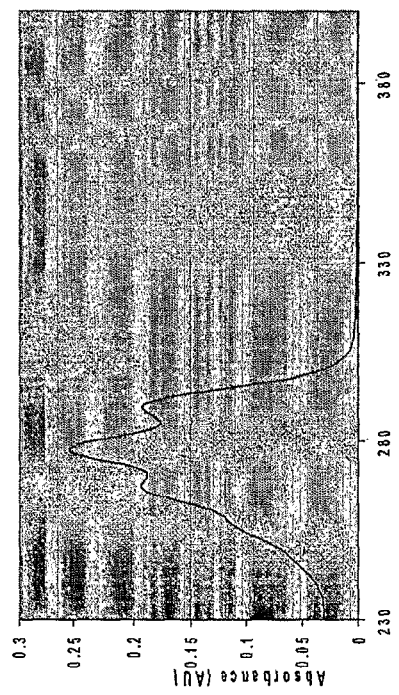
Figure 23:
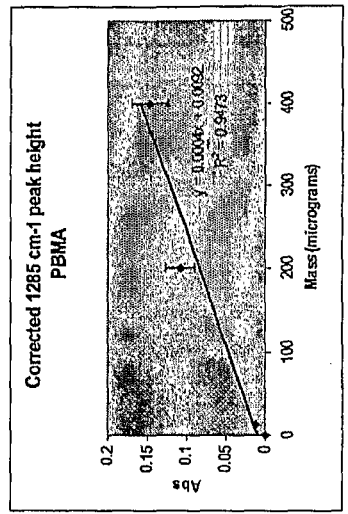
Figure 23:
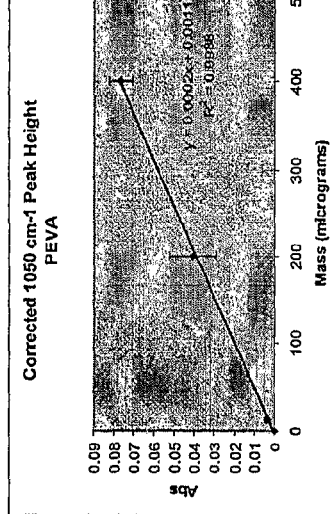
Figure 23:
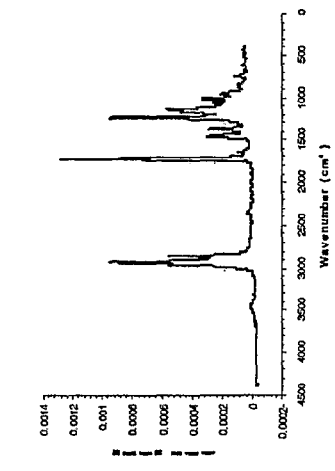
Figure 24:
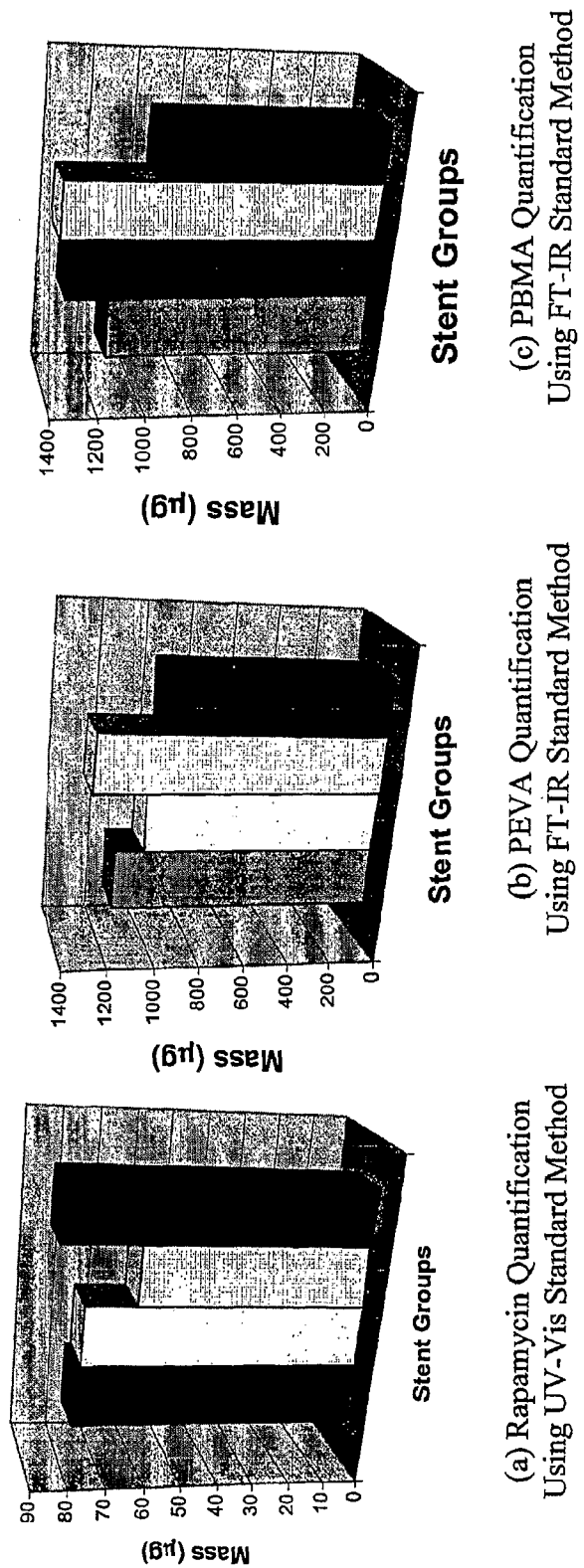
FIG. 24. Quantification of Coating Components, (mean concentrations (3 stents each); 4 cell by 8 mm parylene coated). (a) Rapamycin Quantification (74±11 μg) Using UV-Vis Method; (b) PEVA (1060±190 μg) and (c) PBMA (1110±198 μg) Quantification Using FT-IR Method, as discussed in example 15.

UV-Vis and FT-IR Analysis of Rapamycin/PEVA/PBM Coated Stents for Quantification of Coating Components A UV-VIS method was developed and used to quantitatively determine the mass of rapamycin coated onto the stents with poly(ethylene-co-vinyl acetate) (PEVA) and poly(butyl methacrylate) (PBMA). The UV-Vis spectrum of Rapamycin is shown in FIG. 23(a) and a Rapamycin calibration curve was obtained, λ@277 nm in ethanol, as shown in FIG. 23(b). Rapamycin was dissolved from the coated stent in ethanol, and the drug concentration and mass calculated. An average mass of 74±11 μg Rapamycin was loaded onto the stents. The results in FIG. 24 (a) show a consistent drug coating: (+/−) 15% stent-to-stent, (+/−) 12% run-to-run, (mean concentrations (3 stents each); 4 cell by 8 mm parylene coated).

An FT-IR method was developed and used to quantitatively determine the mass of PEVA and PBMA coated onto stents with rapamycin. The FT-IR spectra of PEVA and PBMA is shown in FIG. 23(c) and calibration curves were obtained using Beer's Law for PEVA λ@~1050 $cm^{-1}$ and PBMA λ@~1285 $cm^{-1}$, as shown in FIGS. 23(d) and (e), respectively. The polymers were dissolved from the coated stent in methylene chloride, and the polymer concentrations and the masses calculated accordingly. An average mass of 1060±190 μg PEVA and 1110±198 μg PBMA was loaded onto the stents. The results in FIGS. 24(b) and (c) show a consistent polymer coating: (+/−) 18% stent-to-stent, (+/−) 15% run-to-run, (mean concentrations (3 stents each); 4 cell by 8 mm parylene coated).

Example 29

Figure 25:
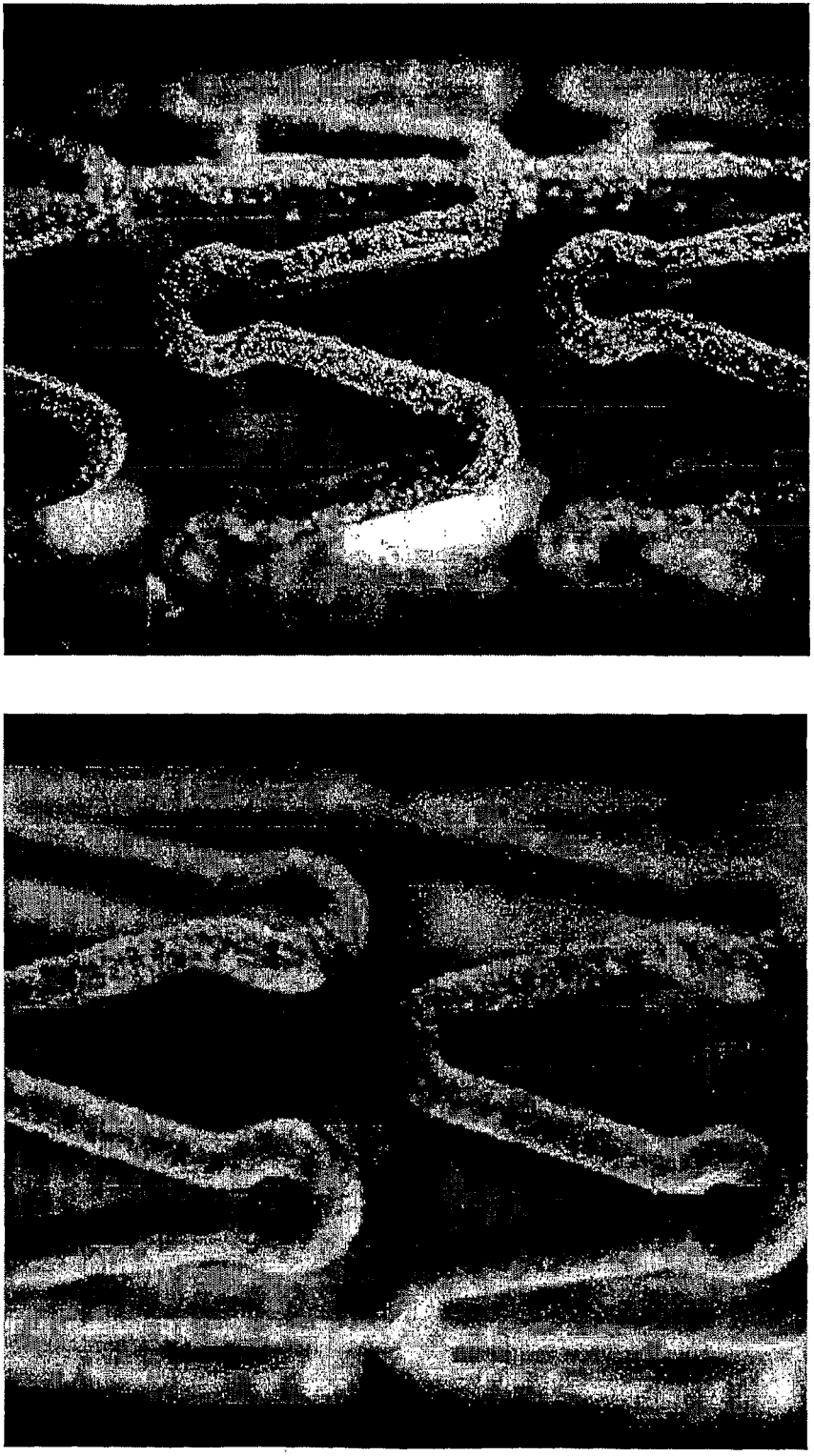
FIG. 25. Optical Microscopy Showing the Outside Surface of a 3 mm Guidant TriStar® Stent Coated with Paclitaxel-polymer composite, as discussed in example 16.
Figure 26:
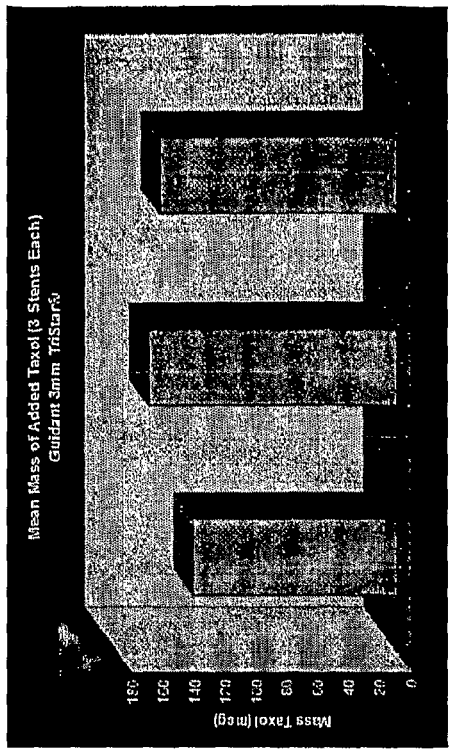
FIG. 26. Paclitaxel Quantification After Coating on a 3 mm Guidant TriStar® Stent with Paclitaxel/PEVA/PMBA composite, as discussed in example 16. (a) Calibration Curve at 228 nm in ethanol Using UV-Vis Standard Method and (b) Quantification (148±14 μg) Using UV-Vis Method.
Figure 26:
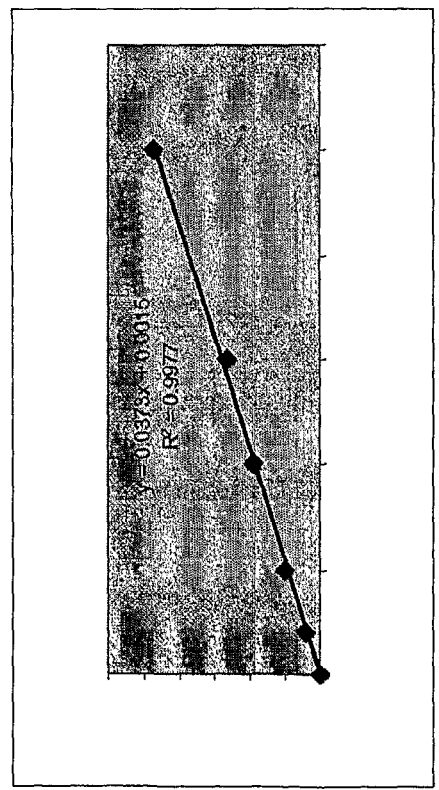

Coating of Stents with Paclitaxel/PEVA/PMBA 3 mm Guidant TriStar® Stents were coated with a Paclitaxel/PEVA/PMBA composite, by processes of the invention, as described herein. The coated stents were examined by optical microscopy, and photos of the outside surface of the stent (a) prior to sintering and (b) after sintering are shown in FIG. 25. FIG. 26(a) represents the UV-Vis calibration curve developed for Paclitaxel, λ@228 nm in ethanol, using the methods of example 28, as described above. Rapamycin was dissolved from the coated stent in ethanol, and the drug concentration and mass calculated, to give an average mass of 148±14 μg loaded Rapamycin, as shown in FIG. 26(b).

Example 30

Figure 27:
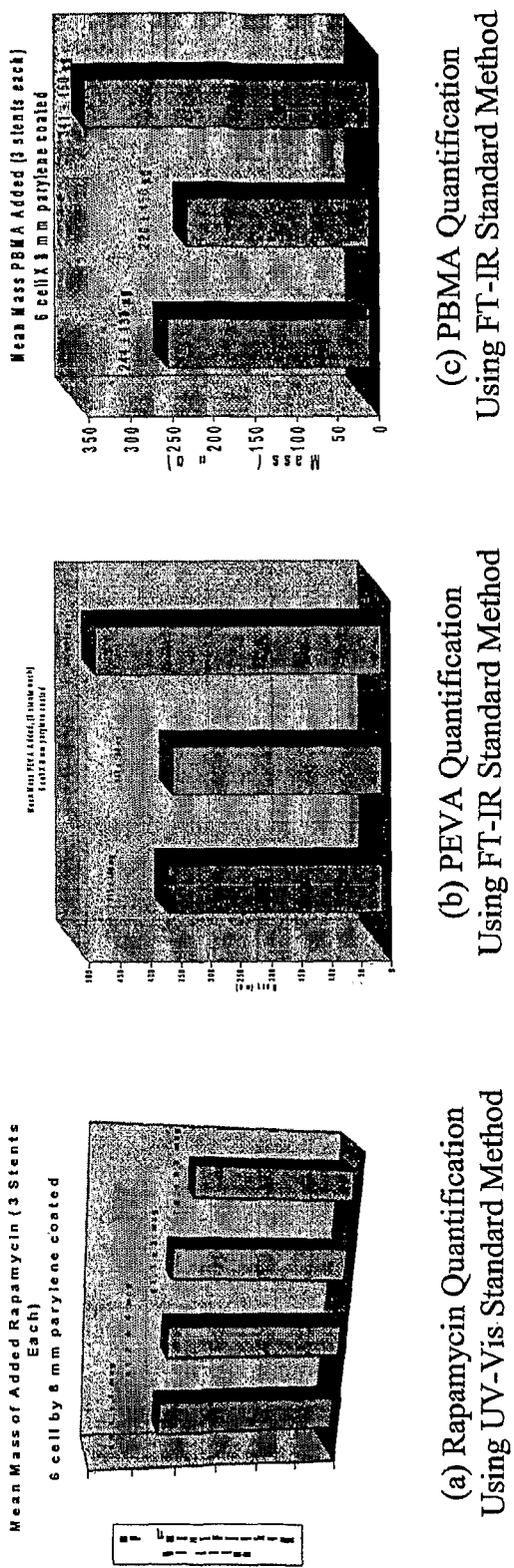
FIG. 27. Quantification of Coating Components, (mean concentrations (3 stents each); 6 cell by 8 mm parylene coated). (a) Rapamycin Quantification (81±3 μg) Using UV-Vis Method; (b) PEVA (391±69 μg) and (c) PBMA (26±64 μg) Quantification Using FT-IR Method, as discussed in example 17.
Figure 28:
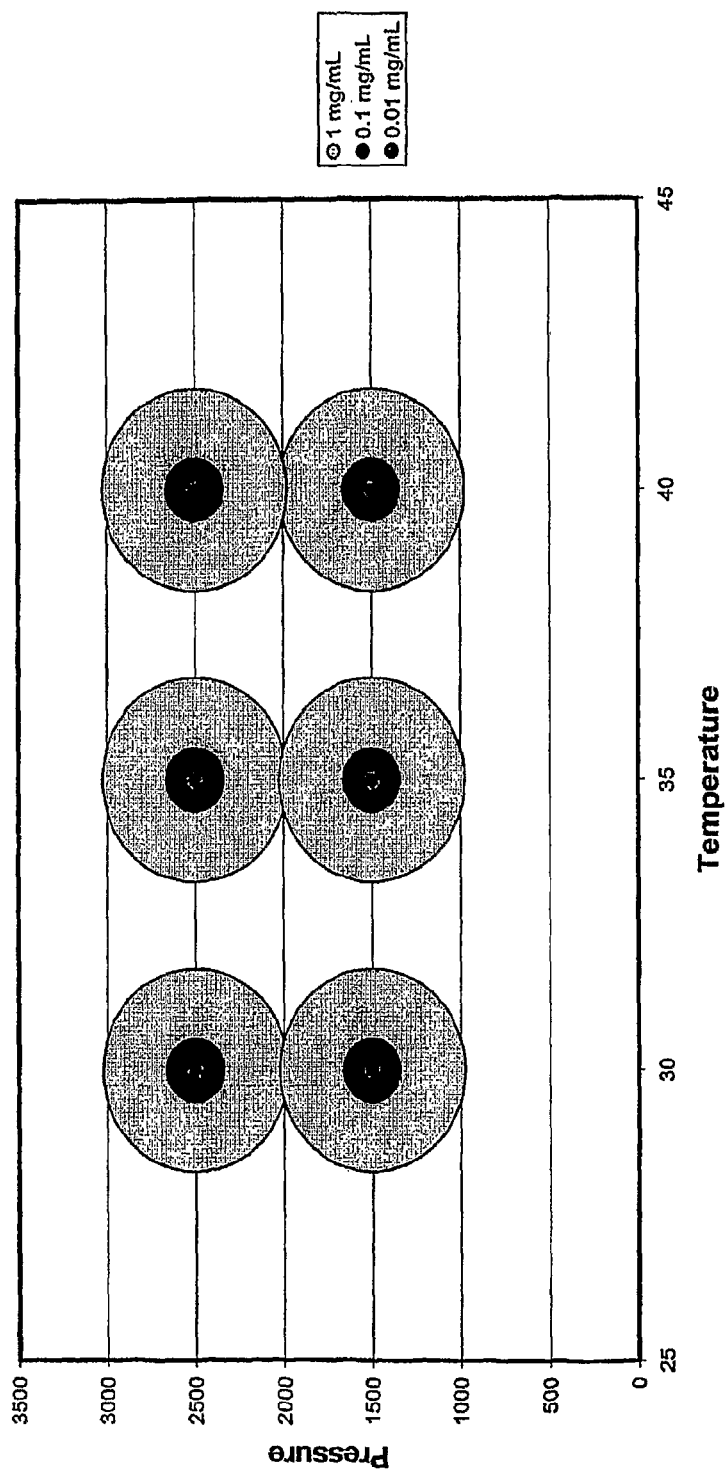
FIG. 28. Shows a graphical summary of conditions employed in sintering experiments according to embodiments of the invention.

UV-Vis and FT-IR Analysis of Rapamycin/PEVA/PBM Coated Stents for Quantification of Coating Components The UV-VIS and FT-IR methods, described in example 28, were used to determine the quantities of Rapamycin, PEVA and PBMA respectively, from stents coated with Rapamycin, PEVA and PBMA by processes of the invention, as described herein. The component quantifications are shown in FIG. 27 and calculated; (a) an average mass of 81±3 μg Rapamycin was loaded onto the stents, (b) an average mass of 391±69 μg PEVA and (c) 268±64 μg PBMA was loaded onto the stents.

Example 31

Coating of Stents with Rapamycin or Paclitaxel, Polyethylene-co-Vinyl Acetate (PEVA) and Polybutyl Methacrylate (PBMA)

A 25 mL stainless steel reservoir is charged with 150.0±0.1 mg of poly(ethylene co-vinyl acetate) (PEVA) and 150.0±0.1 mg of poly(butyl methacrylate) (PBMA) to which is transferred 20.0±0.3 grams of dichlorofluoromethane. The pressure rises in the reservoir to approximately 28 psig. The reservoir is heated to 60° C. after transferring dichlorofluoromethane to the reservoir. The reservoir is then pressurized with helium until the pressure reaches 700±30 psig. Helium acts as a piston to push out the dichlorofluoromethane-polymer solution. The reservoir is isolated from the system by appropriate valving. A second stainless steel reservoir with volume of 15±1 mL is charged with 13 mg of drug compound (rapamycin or Paclitaxel). This reservoir is pressurized to 400±5 psig with carbon dioxide gas. The temperature of the drug reservoir is room temperature. The reservoir is isolated from the system by appropriate valving. A third reservoir is charged with tetrahydrofuran or dichloromethane solvent so that the polymer nozzle can be flushed between polymer sprays. This reservoir is also pressurized with helium to 700 psig and isolated from the system by appropriate valving. The polymer spray nozzle is heated to 120±2° C. while the drug spray nozzle remains at room temperature. Stents are loaded into the stent fixture and attached to a high voltage source via an alligator clamp. The alligator clamp enters the coating chamber via an electrically insulated pass through. Carbon dioxide gas is admitted into the coating vessel at 8 psig for a period of 5 minutes through a third gas flush nozzle to remove air and moisture to eliminate arcing between the nozzles and components held at high potential. After flushing the coating chamber with carbon dioxide gas, a potential of 35 kV is applied to the stents via a high voltage generator. This potential is maintained during each coating step of polymer and drug. The potential is removed when the polymer spray nozzle is flushed with tetrahydrofuran or dichloromethane. Polymer solution is sprayed for 7 secs from the polymer solution reservoir into the coating chamber. The applied potential is turned off and the polymer nozzle is removed from the coating chamber and flushed with solvent for 2 minutes and then flushed with helium gas for approximately one minute until all solvent is removed from the nozzle. The coating chamber is flushed with carbon dioxide gas during the nozzle solvent flush to flush out dichlorofluoromethane gas. The polymer spray nozzle is placed back in the coating chamber and the carbon dioxide gas flush is stopped. A 35 kV potential is applied to the stents and the drug compound is rapidly sprayed into the coating chamber by opening appropriate valving. After one minute of rest time, polymer spray commences for another seven seconds. The process can be repeated with any number of cycles.

The various analytical methods developed to examine the coated stents and the results they generated are summarized in the table below:

| Analytical Method | To Provide | Result |
| --- | --- | --- |
| Optical microscope | Visible images of the stents. Empirical survey of coating uniformity | Nanoparticles deposited evenly on all surfaces of stent Sintering to conformal film (with visual evidence of crystalline drug) |
| SEM | Top-down and cross-sectional images (electron micrographs) at various magnifications. Gross estimates of coating uniformity and thickness | Very smooth and conformal films at high magnification 10.2 ± 0.3 µm well-sintered films via cross-sectional analysis |
| X-ray diffraction (XRD) | Quantitative indication of drug morphology in coated films on proxy substrates | +65% crystalline rapamycin on proxy samples |
| Differential Scanning Calorimetry (DSC) | Qualitative evidence of crystalline rapamycin from proxy substrates (crystalline melt) | Demonstrated rapamycin crystalline melt (185-200° C.) |
| Confocal Raman | Compositional data (drug, polymer A, Polymer B) at various depths in the film on the coated stents (i.e. surface, 2 µm deep, 4-µm deep, etc.) | Drug distributed throughout polymer coated stents |
| UV-Vis Spectroscopy | Quantitative compositional information for drug loading on 'sacrificial' coated stents, BL method | 74 ± 11 µg drug loaded onto stents, run-to-run control within 12% deviation |
| FT-IR spectroscopy | Quantitative compositional information for loading of both polymers on 'sacrificial' coated stents, BL method | 1060 ± 190 µg PEVA loaded onto stents 1110 ± 198 µg PBMA loaded onto stents |

Example 32

Figure 29:
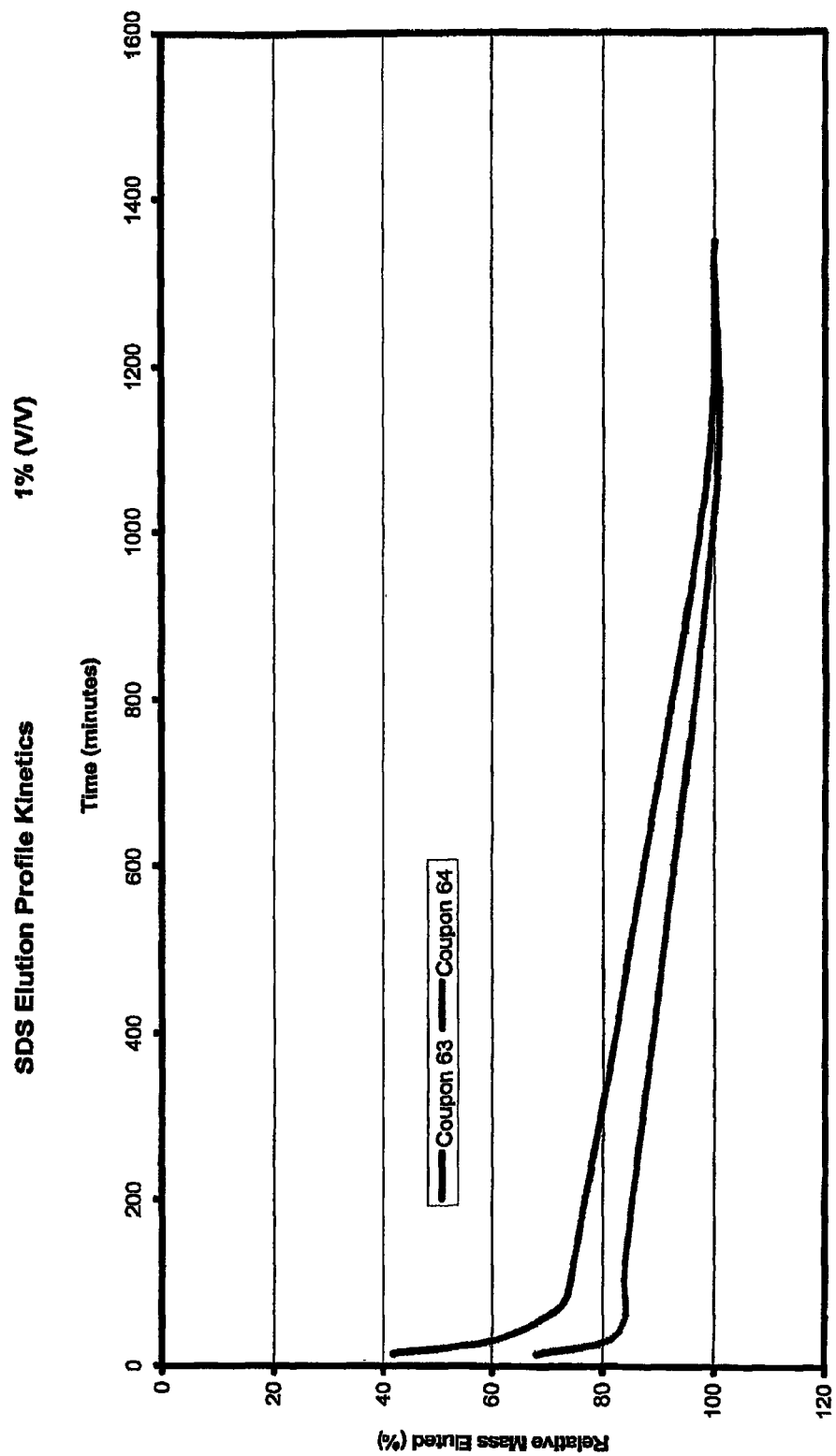
FIGS. 29 and 30 illustrate elution profiles for stents coated according to embodiments of the invention.
Figure 30:
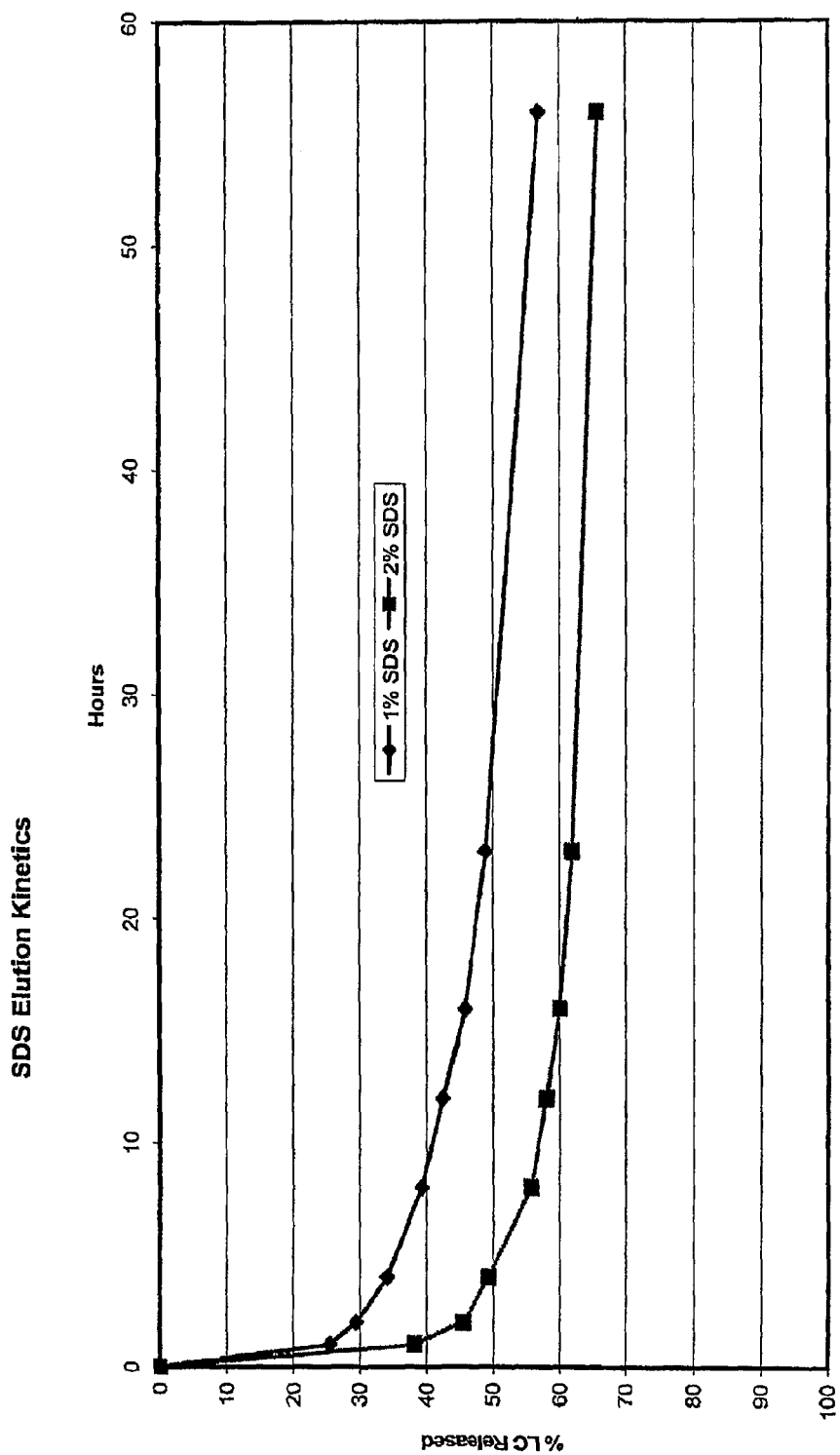

FIGS. 29 and 30

An elution medium was identified to produce elution profile under static conditions. SDS surfactant at 1% (v/v) in phosphate buffer at pH 7.0 was selected as the elution medium based upon comparison of the elution profiles generated with this medium to the desired elution profiles. The experiment showed that it was possible to generate an elution profile over a period of 30 hrs in a thermostatically controlled bath held at 37±1° C. over the time of the elution experiment (see FIG. 29). The samples used were sterilized at using an ethylene oxide process. Additional elution work was carried out to develop an elution method. The materials used were supplied by Aldrich (polymers) and LC Laboratories (Rapamycin). The elution profile is shown in FIG. 30. Another set of stents was analyzed. The set included 6 drug coated stents and two placebo stents. This set of stents showed no elution; however, the placebo stent was sintered simultaneously with the drug coated stent. Upon analysis, the placebo showed some rapamycin. These stents were subjected to stripping analysis to determine if any drug was present but simply did not elute. No drug was found.

Example 33

Figure 31:
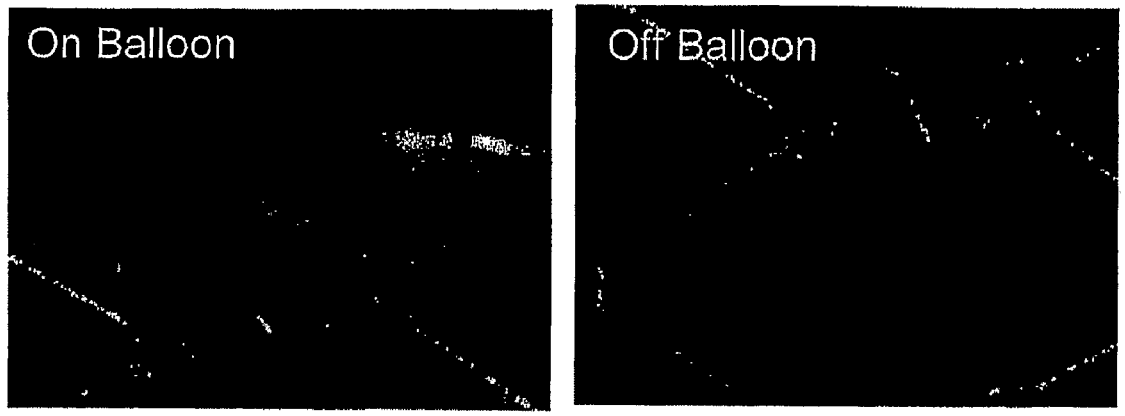
FIG. 31 illustrates mechanical stability of stents coated according to embodiments of the invention.

Mechanical Stability of Illustrative Coated Stents (FIG. 31)

Balloon Inflation: Stents were transferred onto a balloon dilation catheter vial an "over the wire" transfer.

A stylet was inserted into the lumen of the catheter; the stent was picked up via the sterile needle and transferred onto the stylet. The stent was manipulated on to the center of the balloon—and the entire assembly was placed under the microscope. Due to the lack of crimping equipment, the stent was adjusted in position by the use of a small vascular forceps placed on the balloon to preclude the stent from shooting off during inflation and balloon expansion.

Inflation/(Slow Inflation)

The balloon was inflated using an indeflator with an atmospheric pressure gauge—and expanded in the same fashion that one would inflate a balloon/stent during an intervention, (rapid expansion)—and the stents were observed at the completion of the "procedure". The balloon was taken up one atmosphere at a time—and the stent/balloon interface examined wider the microscope at each inflation. The balloon stent was placed on a clean microscope slide—to catch any particulate. During the entire inflation process—no particulate/no separation/nor flaking was evidenced on any of the stents. Materials on and around the abluminal area were seen to be deformed and flattened by the balloon inflation—and were seen to be in approximation to the stent struts. Any of the materials that were crossed or jumped from strut to strut were particularly examined towards the effect of the expansion on the materials. In these experiments, the crossed strutted materials would break off—rather they elongated during the expansion—and never separated from the main body.

Over Inflation

Each of the stents was inflated to its nominal expansion size for examination—and then the stent was further expanded until balloon rupture—achieving in many cases a 75% increase in size. Particular attention as paid to the inner and outer portions of the angled aspects of the stent strut that provides the ability to expand. Where the nominal expanded angle might be on the order of 20-25 degrees of deflection we were taking the stent to a point where these angles were 45 plus degrees. None of the hyper expansion caused any deformation or flaking or separation of the coating.

The materials showed good adhesion properties. The materials did not exhibit any lack of adhesion even with excessive expansion. In the major areas of stent flex/deformation during balloon inflation—no separation was seen. No particulate is evidenced in the shipping vials. While some degree of strut-to-strut "cross talk" was seen—it was primarily as a result of environmental contamination—which can be eliminated or reduce, for example, by using clean room and laminar flow hoods and/or filtered gases. The polymer and drug combination appears to have excellent elongation properties.

In summary, in certain embodiments, the present invention provides a method for coating drug-eluting stents. Polymer(s) and drug(s) are applied in a controlled, low-temperature, solvent-free process. In one embodiment Rapamycin, PBMA and PEVA are applied to provide a conformal, consistent coating at target Rapamycin loading, in a 1:1 mixture of PBMA:PEVA, at a thickness of ~10 μM, containing zero residual solvent. The Rapamycin is deposited in crystalline morphology (+50%). The Rapamycin/PEVA/PBMA film is applied using a method through which the stent is not exposed to solvents in the liquid state, wherein the drug and polymer content is highly controllable, and easily adaptable for different drugs, different (resorbable and permanent) polymers, multiple drugs on a single stent, and provides for a high degree of stent-to-stent precision. The absence of exposure of the stent to traditional liquid solvents during deposition enables control over drug content at variable film depths.

The foregoing is illustrative of the present invention, and is not to be construed as limiting thereof. Chile embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention is claimed is:

1. A method for coating a substrate, said coating comprising at least one polymer; and at least one pharmaceutical agent in a therapeutically desirable morphology; said method comprising the following steps:
   a) discharging the at least one pharmaceutical agent in dry powder form through a first orifice; discharging the at least one polymer in dry powder form through a second orifice; depositing polymer and pharmaceutical agent particles onto said substrate, wherein an electrical potential is maintained between the substrate and the polymer and pharmaceutical agent particles, thereby forming said coating; and then
   b) sintering said coating under conditions that do not substantially modify the morphology of said pharmaceutical agent, wherein said sintering comprises treating said coated substrate with a compressed gas, compressed liquid or supercritical fluid that is a non-solvent for both the polymer and the pharmaceutical agent, wherein the therapeutically desirable morphology of said pharmaceutical agent is crystalline or semi-crystalline.

2. A substrate comprising a coating formed by the method of claim 1.

3. A biomedical implant comprising a coating formed by the method of claim 1.

4. The method of claim 1, further comprising depositing a top layer on said coating.

5. The method of claim 4, wherein said top coating is a polymer film.

6. The method of claim 1, wherein said first and said second orifices are provided as one single orifice.

7. The method of claim 1, wherein the substrate is electrostatically charged.

8. The method of claim 1, wherein said substrate is a biomedical implant.

9. The method of claim 8, wherein said biomedical implant is selected from the group consisting of stents, joints, screws, rods, pins, plates, staples, shunts, clamps, clips, sutures, suture anchors, electrodes, catheters, leads, grafts, dressings, pacemakers, pacemaker housings, cardioverters, cardioverter housings, defibrillators, defibrillator housings, prostheses, ear drainage tubes, ophthalmic implants, orthopedic devices, vertebral disks, bone substitutes, anastomotic devices, perivascular wraps, colostomy bag attachment devices, hemostatic barriers, vascular implants, vascular supports, tissue adhesives, tissue sealants, tissue scaffolds and intraluminal devices.

10. The method of claim 1, wherein at least 50% of said pharmaceutical agent in powder form is crystalline or semi-crystalline.

11. The method of claim 1, wherein said pharmaceutical agent comprises at least one drug.

12. The method of claim 1, wherein said compressed gas, compressed liquid or supercritical fluid comprises carbon dioxide, isobutylene or a mixture thereof.

13. The method of claim 1, wherein the at least one polymer comprises two or more polymers, wherein the first polymer swells in aqueous media and the second polymer does not substantially swell in aqueous media.

14. The method of claim 13, wherein in aqueous media said pharmaceutical agent elutes from said first polymer, and substantially does not elute from second polymer.

15. The method of claim 13, wherein the first and/or second supercritical or near critical mixtures are discharged under RESS conditions.

16. The method of claim 1, wherein the substrate is a vascular stent.

17. The method of claim 1, wherein said at least one pharmaceutical agent is selected from: Paclitaxel, Sirolimus, Everolimus, Zotarolimus, Dexamethasone, Tacrolimus, Biolimus, and derivatives.

18. The method of claim 1 wherein the pharmaceutical agent comprises a macrolide immunosuppressive drug comprising one or more of rapamycin, 40-O-(2-Hydroxyethyl) rapamycin (everolimus), 40-O-Benzyl-rapamycin, 40-O-(4'-Hydroxymethyl)benzyl -rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin 40-O-(2-Hydroxy)ethoxycar-bonylmethyl-rapamycin, 40-O-(3-Hydroxy)propyl-rapamycin, 40-O-(6-Hydroxy)hexyl-rapamycin, 40-O-[2-(2-Hydroxy)ethoxy]ethyl-rapamycin, 40-O-[(3S)-2,2-Dimethyldioxolan-3-yl]methyl-rapamycin, 40-O-[(2S)-2,3-Dihydroxyprop-1-yl]-rapamycin, 40-O-(2-Acetoxy)ethyl-rapamycin 40-O-(2-Nicotinoyloxy)ethyl-rapamycin, 40-O-[2-(N-Morpholino)acetoxy]ethyl-rapamycin, 40-O-(2-N-Imidazolylacetoxy)ethyl-rapamycin, 40-O-[2-(N-Methyl-N'-piperazinyl)acetoxy]ethyl-rapamycin, 39-O-Desmethyl-39, 40-O,O-ethylene-rapamycin, (26R)-26-Dihydro-40-O-(2-hydroxy)ethyl-rapamycin, 28-O—;Methyl -rapamycin, 40-O-(2-Aminoethyl)-rapamycin, 40-O-(2-Acetaminoethyl)-rapamycin 40-O-(2-Nicotinamidoethyl)-rapamycin, 40-O-(2-(N-Methyl-imidazo-2'-ylcarbethoxamido)ethyl)-rapamycin, 40-O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi -(tetrazolyl)rapamycin (tacrolimus), and 42-[3-hydroxy-2-(hydroxymethyl)-2-methylpropanoate]rapamycin (temsirolimus).

* * * * *